(12) United States Patent
Kaula et al.

(10) Patent No.: US 7,522,953 B2
(45) Date of Patent: Apr. 21, 2009

(54) SYSTEM AND METHODS FOR PERFORMING SURGICAL PROCEDURES AND ASSESSMENTS

(75) Inventors: Norbert F. Kaula, Arvada, CO (US); Jeffrey J. Blewett, San Diego, CA (US); Goretti Medeiros, legal representative, Plantsville, CT (US); James Gharib, San Diego, CA (US); Allen Farquhar, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 558 days.

(21) Appl. No.: 10/809,280

(22) Filed: Mar. 25, 2004

(65) Prior Publication Data

US 2005/0075578 A1    Apr. 7, 2005

Related U.S. Application Data

(63) Continuation of application No. PCT/US02/30617, filed on Sep. 25, 2002.

(60) Provisional application No. 60/325,424, filed on Sep. 25, 2001.

(51) Int. Cl.
*A61B 5/05* (2006.01)
*A61B 5/04* (2006.01)

(52) U.S. Cl. ...................... 600/546; 600/554

(58) Field of Classification Search ................ 600/546, 600/547, 554; 607/2; 606/32, 41
See application file for complete search history.

(56) References Cited

U.S. PATENT DOCUMENTS

| 972,983 | A | 10/1910 | Arthur | |
|---|---|---|---|---|
| 1,328,624 | A | 1/1920 | Graham | |
| 1,548,184 | A | 8/1925 | Cameron | |
| 2,704,064 | A | 3/1955 | Fizzell et al. | 128/2.1 |
| 2,736,002 | A | 2/1956 | Oriel | |
| 2,808,826 | A | 10/1957 | Reiner et al. | |
| 3,364,929 | A | 1/1968 | Ide et al. | 128/172.1 |

(Continued)

FOREIGN PATENT DOCUMENTS

EP    0972538 A2    1/2000

(Continued)

OTHER PUBLICATIONS

"Electromyography System", *International Search Report*, International Application No. PCT/US00/32329,(Apr. 27, 2001), 9 pages.

(Continued)

*Primary Examiner*—Max Hindenburg
*Assistant Examiner*—Jonathan M Foreman
(74) *Attorney, Agent, or Firm*—Jonathan Spangler; Rory Schermerhorn

(57) ABSTRACT

The present invention involves systems and related methods for performing surgical procedures and assessments, including the use of neurophysiology-based monitoring to: (a) determine nerve proximity and nerve direction to surgical instruments employed in accessing a surgical target site; (b) assess the pathology (health or status) of a nerve or nerve root before, during, or after a surgical procedure; and/or (c) assess pedicle integrity before, during or after pedicle screw placement, all in an automated, easy to use, and easy to interpret fashion so as to provide a surgeon-driven system.

25 Claims, 35 Drawing Sheets

U.S. PATENT DOCUMENTS

| | | | |
|---|---|---|---|
| 3,664,329 A | 5/1972 | Naylor | 128/2.1 R |
| 3,682,162 A | 8/1972 | Colyer | 128/2.1 R |
| 3,785,368 A | 1/1974 | McCarthy et al. | 128/2.1 Z |
| 3,830,226 A | 8/1974 | Staub et al. | 128/2.1 R |
| 3,957,036 A | 5/1976 | Normann | 128/2.1 R |
| 4,099,519 A | 7/1978 | Warren | 128/2.1 R |
| 4,164,214 A | 8/1979 | Stark et al. | |
| 4,207,897 A | 6/1980 | Lloyd et al. | 128/303.1 |
| 4,224,949 A | 9/1980 | Scott et al. | 128/734 |
| 4,226,228 A | 10/1980 | Shin et al. | |
| 4,235,242 A | 11/1980 | Howson et al. | 128/695 |
| 4,285,347 A | 8/1981 | Hess | 128/785 |
| 4,291,705 A | 9/1981 | Severinghaus et al. | 600/546 |
| 4,461,300 A | 7/1984 | Christensen | |
| 4,515,168 A | 5/1985 | Chester et al. | 128/741 |
| 4,519,403 A | 5/1985 | Dickhudt | 128/785 |
| 4,545,374 A | 10/1985 | Jacobson | |
| 4,561,445 A | 12/1985 | Berke et al. | 128/642 |
| 4,562,832 A | 1/1986 | Wilder et al. | |
| 4,573,448 A | 3/1986 | Kambin | |
| 4,592,369 A | 6/1986 | Davis et al. | 128/733 |
| 4,595,018 A | 6/1986 | Rantala | 128/733 |
| 4,633,889 A | 1/1987 | Talalla et al. | 128/784 |
| 4,658,835 A | 4/1987 | Pohndorf | 128/785 |
| 4,744,371 A | 5/1988 | Harris | 607/117 |
| 4,759,377 A | 7/1988 | Dykstra | 128/733 |
| 4,784,150 A | 11/1988 | Voorhies et al. | |
| 4,807,642 A | 2/1989 | Brown | 128/733 |
| 4,892,105 A | 1/1990 | Prass | 128/741 |
| 4,926,865 A | 5/1990 | Oman | 128/421 |
| 4,962,766 A | 10/1990 | Herzon | 128/741 |
| 4,964,411 A | 10/1990 | Johnson et al. | 128/733 |
| 5,007,902 A | 4/1991 | Witt | 604/117 |
| 5,058,602 A | 10/1991 | Brody | 128/733 |
| 5,081,990 A | 1/1992 | Deletis | 128/642 |
| 5,092,344 A | 3/1992 | Lee | 128/741 |
| 5,127,403 A | 7/1992 | Brownlee | 128/419 P |
| 5,161,533 A | 11/1992 | Prass et al. | 128/639 |
| 5,196,015 A | 3/1993 | Neubardt | 606/61 |
| RE34,390 E | 9/1993 | Culver | 128/731 |
| 5,255,691 A | 10/1993 | Otten | 607/117 |
| 5,282,468 A | 2/1994 | Klepinski | 128/642 |
| 5,284,153 A | 2/1994 | Raymond et al. | 128/741 |
| 5,284,154 A | 2/1994 | Raymond et al. | 128/741 |
| 5,299,563 A | 4/1994 | Seton | |
| 5,312,417 A | 5/1994 | Wilk | 606/114 |
| 5,313,956 A | 5/1994 | Knutsson et al. | 128/741 |
| 5,327,902 A | 7/1994 | Lemmen | 128/734 |
| 5,333,618 A | 8/1994 | Lekhtman et al. | 128/734 |
| 5,375,067 A | 12/1994 | Berchin | 364/487 |
| 5,383,876 A | 1/1995 | Nardella | 606/49 |
| 5,474,558 A | 12/1995 | Neubardt | 606/79 |
| 5,480,440 A | 1/1996 | Kambin | |
| 5,482,038 A | 1/1996 | Ruff | 128/642 |
| 5,484,437 A | 1/1996 | Michelson | |
| 5,540,235 A | 7/1996 | Wilson | 128/741 |
| 5,549,656 A | 8/1996 | Reiss | 607/48 |
| 5,560,372 A | 10/1996 | Cory | 128/741 |
| 5,566,678 A | 10/1996 | Cadwell | 128/731 |
| 5,579,781 A | 12/1996 | Cooke | 128/733 |
| 5,593,429 A | 1/1997 | Ruff | 607/116 |
| 5,599,279 A | 2/1997 | Slotman et al. | |
| 5,630,813 A | 5/1997 | Kieturakis | 606/46 |
| 5,671,752 A | 9/1997 | Sinderby et al. | 128/733 |
| 5,707,359 A | 1/1998 | Bufalini | 604/104 |
| 5,711,307 A | 1/1998 | Smits | 128/733 |
| 5,728,046 A | 3/1998 | Mayer et al. | |
| 5,741,253 A | 4/1998 | Michelson | |
| 5,759,159 A | 6/1998 | Masreliez | |
| 5,772,661 A | 6/1998 | Michelson | |
| 5,775,331 A | 7/1998 | Raymond et al. | 128/741 |
| 5,776,144 A | 7/1998 | Leysieffer et al. | |
| 5,779,642 A | 7/1998 | Nightengale | 600/461 |
| 5,785,658 A | 7/1998 | Benaron et al. | |
| 5,797,854 A | 8/1998 | Hedgecock | 600/554 |
| 5,814,073 A | 9/1998 | Bonutti | 606/232 |
| 5,830,151 A | 11/1998 | Hadzic et al. | 600/554 |
| 5,851,191 A | 12/1998 | Gozani | 600/554 |
| 5,853,373 A | 12/1998 | Griffith et al. | 600/554 |
| 5,860,973 A | 1/1999 | Michelson | |
| 5,862,314 A | 1/1999 | Jeddeloh | |
| 5,872,314 A | 2/1999 | Clinton | |
| 5,885,219 A | 3/1999 | Nightengale | 600/461 |
| 5,888,196 A | 3/1999 | Bonutti | 600/204 |
| 5,902,231 A | 5/1999 | Foley et al. | |
| 5,928,139 A | 7/1999 | Koros | |
| 5,928,158 A | 7/1999 | Aristides | 600/547 |
| 5,976,094 A | 11/1999 | Gozani et al. | 600/483 |
| 6,004,262 A | 12/1999 | Putz et al. | 600/114 |
| 6,027,456 A | 2/2000 | Feler et al. | 600/554 |
| 6,038,469 A | 3/2000 | Karlsson et al. | |
| 6,038,477 A | 3/2000 | Kayyali | 607/72 |
| 6,050,992 A | 4/2000 | Nichols | 606/41 |
| 6,074,343 A | 6/2000 | Nathanson et al. | |
| 6,104,957 A | 8/2000 | Alo et al. | 607/46 |
| 6,120,503 A | 9/2000 | Michelson | |
| 6,132,386 A | 10/2000 | Gozani et al. | 600/554 |
| 6,132,387 A | 10/2000 | Gozani et al. | 600/554 |
| 6,135,965 A | 10/2000 | Tumer et al. | 600/476 |
| 6,139,493 A | 10/2000 | Koros et al. | |
| 6,146,335 A | 11/2000 | Gozani | 600/554 |
| 6,161,047 A | 12/2000 | King et al. | 607/62 |
| 6,206,826 B1 | 3/2001 | Mathews et al. | |
| 6,224,549 B1 | 5/2001 | Drongelen | 600/300 |
| 6,259,945 B1 | 7/2001 | Epstein et al. | 600/547 |
| 6,266,558 B1 | 7/2001 | Gozani et al. | 600/547 |
| 6,273,905 B1 | 8/2001 | Streeter | |
| 6,292,701 B1 | 9/2001 | Prass et al. | 607/116 |
| 6,306,100 B1 | 10/2001 | Prass | |
| 6,312,392 B1 | 11/2001 | Herzon | 600/554 |
| 6,325,764 B1 | 12/2001 | Griffith et al. | |
| 6,334,068 B1 | 12/2001 | Hacker | |
| 6,425,859 B1* | 7/2002 | Foley et al. | 600/204 |
| 6,425,901 B1 | 7/2002 | Zhu et al. | |
| 6,451,015 B1 | 9/2002 | Rittman, III et al. | |
| 6,466,817 B1 | 10/2002 | Kaula et al. | 600/546 |
| 6,500,128 B2 | 12/2002 | Marino | 600/554 |
| 6,564,078 B1 | 5/2003 | Marino et al. | 600/373 |
| 6,760,616 B2 | 7/2004 | Hoey et al. | |
| 6,819,956 B2 | 11/2004 | DiLorenzo | |
| 6,902,569 B2 | 6/2005 | Parmer et al. | |
| 6,926,728 B2* | 8/2005 | Zucherman et al. | 606/190 |
| 6,929,606 B2 | 8/2005 | Ritland | |
| 7,079,883 B2 | 7/2006 | Marino et al. | |
| 7,089,059 B1 | 8/2006 | Pless | |
| 7,177,677 B2 | 2/2007 | Kaula et al. | |
| 7,207,949 B2 | 4/2007 | Miles et al. | |
| 2001/0039949 A1* | 11/2001 | Loubser | 128/200.26 |
| 2001/0056280 A1 | 12/2001 | Underwood et al. | |
| 2002/0007129 A1 | 1/2002 | Marino | 600/546 |
| 2002/0072686 A1 | 6/2002 | Hoey et al. | 600/547 |
| 2002/0161415 A1 | 10/2002 | Cohen et al. | |
| 2002/0193843 A1 | 12/2002 | Hill et al. | |
| 2003/0032966 A1 | 2/2003 | Foley et al. | |
| 2005/0004593 A1 | 1/2005 | Simonson | |
| 2005/0004623 A1 | 1/2005 | Miles et al. | |
| 2005/0182454 A1 | 8/2005 | Gharib et al. | |
| 2006/0025703 A1 | 2/2006 | Miles et al. | |
| 2006/0069315 A1 | 3/2006 | Miles et al. | |
| 2007/0016097 A1 | 1/2007 | Farquhar et al. | |

2007/0198062 A1 8/2007 Miles et al.

FOREIGN PATENT DOCUMENTS

| WO | WO-0038574 A1 | 7/2000 |
| WO | WO-0137728 A1 | 5/2001 |
| WO | WO-2005013805 A3 | 2/2005 |

OTHER PUBLICATIONS

"Nerve Proximity and Status Detection System and Method", *International Search Report*, International Application No. PCT/US01/18606,(Oct. 18, 2001), 6 pages.

"Relative Nerve Movement and Status Detection System and Method", *International Search Report*, International Application No. PCT/US01/18579,(Jan. 15, 2002), 6 pages.

"System and Method for Determining Nerve Proximity, Direction, and Pathology During Surgery", *International Search Report*, International Application No. PCT/US02/22247,(Mar. 27, 2003), 4 pages.

"System and Methods for Determining Nerve Direction to a Surgical Instrument", *International Search Report*, International Application No. PCT/US03/02056,(Aug. 12, 2003), 5 pages.

"Systems and Methods for Performing Percutaneous Pedicle Integrity Assessments", *International Search Report*, International Application No. PCT/US02/35047,(Aug. 11, 2003), 5 pages.

"Systems and Methods for Performing Surgery Procedures and Assessments", *International Search Report*, International Application No. PCT/US02/30617,(Jun. 5, 2003), 4 pages.

Calancie, et al., "Stimulus-Evoked EMG Monitoring During Transpedicular Lumbosacral Spine Instrumentation", *Spine*, 19(24), (1994), pp. 2780-2786.

Clements, et al., "Evoked and Spontaneous Electromyography to Evaluate Lumbosacral Pedicle Screw Placement", *Spine*, 21(5), (1996),pp. 600-604.

Ford, et al., "Electrical Characteristics of Peripheral Nerve Stimulators Implications for Nerve Localization", *Regional Anesthesia*, 9, (1984), pp. 73-77.

Glassman, et al., "A Prospective Analysis of Intraoperative Electromyographic Monitoring of Pedicle Screw Placement With Computed Tomographic Scan Confirmation", *Spine* , 20(12), (1995), pp. 1375-1379.

Greenblatt, et al., "Needle Nerve Stimulator-Locator: Nerve Blocks with a New Instrument for Locating Nerves", *Anesthesia & Analgesia*, 41(5), (1962), pp. 599-602.

Holland, N. , "Intraoperative Electromyography During Thoracolumbar Spinal Surgery", *Spine*, 23(17), (1998), pp. 1915-1922.

Lenke, et al., "Triggered Electromyographic Threshold for Accuracy of Pedicle Screw Placement", *Spine*, 20 (14), (1995), 1585-1591.

Maguire, et al., "Evaluation of Intrapedicular Screw Position Using Intraoperative Evoked Electromyography", *Spine*, 20(9), (1995), pp. 1068-1074.

Martin, et al., "Initiation of Erection and Semen Release by Rectal Probe Electrostimulation (RPE)", *The Williams & Wilkins Co.*, (1983), pp. 637-642.

Pither, et al., ""The Use of Peripheral Nerve Stimulators for Regional Anesthesia: Review of Experimental Characteristics, Technique, and Clinical Applications"", *Regional Anesthesia*, (1985), pp. 10:47-53.

Raj, et al., "Infraclavicular Brachial Plexus Block—A New Approach", *Anesthesia and Analgesia*, (52)6, (1973), pp. 897-904.

Raj, et al., "The Use of Peripheral Nerve Stimulators For Regional Anesthesia", *Clinical Issues In Regional Anesthesia*, 1 (4), (1985), pp. 1-6.

Raj, et al., "Use of The nerve Stimulator of Peripheral Blocks", *Regional Anesthesia*, (Apr.-Jun. 1980), pp. 14-21.

Raymond, et al., "The Nerve Seeker: A System for Automated Nerve Localization", *Regional Anesthesia*, 17(3), (1992), pp. 151-162.

Shafik, "Cavernous Nerve Simulation through an Extrapelvic Subpubic Approach: Role in Pencil Erection", *Eur. Urol*, 26, (1994), pp. 98-102.

Toleikis, et al., "The Usefulness of Electrical Stimulation for Assessing Pedicle Screw Replacements", *Journal of Spinal Disorder*, 13(4), (2000), pp. 283-289.

Anderson, D. G., et al., "Pedicle screws with high electrical resistance: a potential source of error with stimulus-evoked EMG", *Spine*. 27(14):, Department of Orthopaedic Surgery, University of Virginia,(Jul. 15, 2002), 1577-1581.

Danesh-Clough, T. , et al., "The use of evoked EMG in detecting misplaced thoracolumbar pedicle screws", *Spine*. 26(12), Orthopaedic Department, Dunedin Hospital,(Jun. 15, 2001), 1313-1316.

Darden, B. V., et al., "A comparison of impedance and electromyogram measurements in detecting the presence of pedicle wall breakthrough", *Spine*. 23(2), Charlotte Spine Center, North Carolina,(Jan. 1998),256-262.

Ebraheim, N. A., et al., "Anatomic relations between the lumbar pedicle and the adjacent neural structures", *Spine*. 22(20), Department of Orthopaedic Surgery, Medical College of Ohio,(Oct. 15, 1997),2338-2341.

Haig, A. J., et al., "The relation among spinal geometry on MRI, paraspinal electromyographic abnormalities, and age in persons referred for electrodiagnostic testing of low back symptoms", *Spine*. 27(17), Department of Physical Medicine and Rehabilitation, University of Michigan,(Sep. 1, 2002), 1918-1925.

Holland, N. R., et al., "Higher electrical stimulus intensities are required to activate chronically compressed nerve roots. Implications for intraoperative electromyographic pedicle screw testing", *Spine*. 23(2), Department of Neurology, Johns Hopkins University School of Medicine,(Jan. 15, 1998),224-227.

Minahan, R. E., et al., "The effect of neuromuscular blockade on pedicle screw stimulation thresholds", *Spine*. 25(19), Department of Neurology, Johns Hopkins University, School of Medicine,(Oct. 1, 2000),2526-2530.

"Brackmann II EMG System", *Medical Electronics*, 1999, 4 pages.

"Neurovision SE Nerve Locator/Monitor", *RLN Systems, Inc. Operators Manual*, 1999, 22 pages.

"The Brackmann II EMG Monitoring System", *Medical Electronics Co. Operator's Manual Version 1.1*, 1995, 50 pages.

"The Nicolet Viking IV", *Nicolet Biomedical Products*, 1999, 6 pages.

Journee, H. L. et al., "System for Intra-Operative Monitoring of the Cortical Integrity of the Pedicle During Screw Placement in Low-Back Surgery: Design and Clinical Results", *Sensory and neuromuscular diagnostic instrumentation and data analysis, 18th Annual International Conference on Engineering in Medicine and Biology Society*, 1(31), Oct. 1996, 144-145.

\* cited by examiner

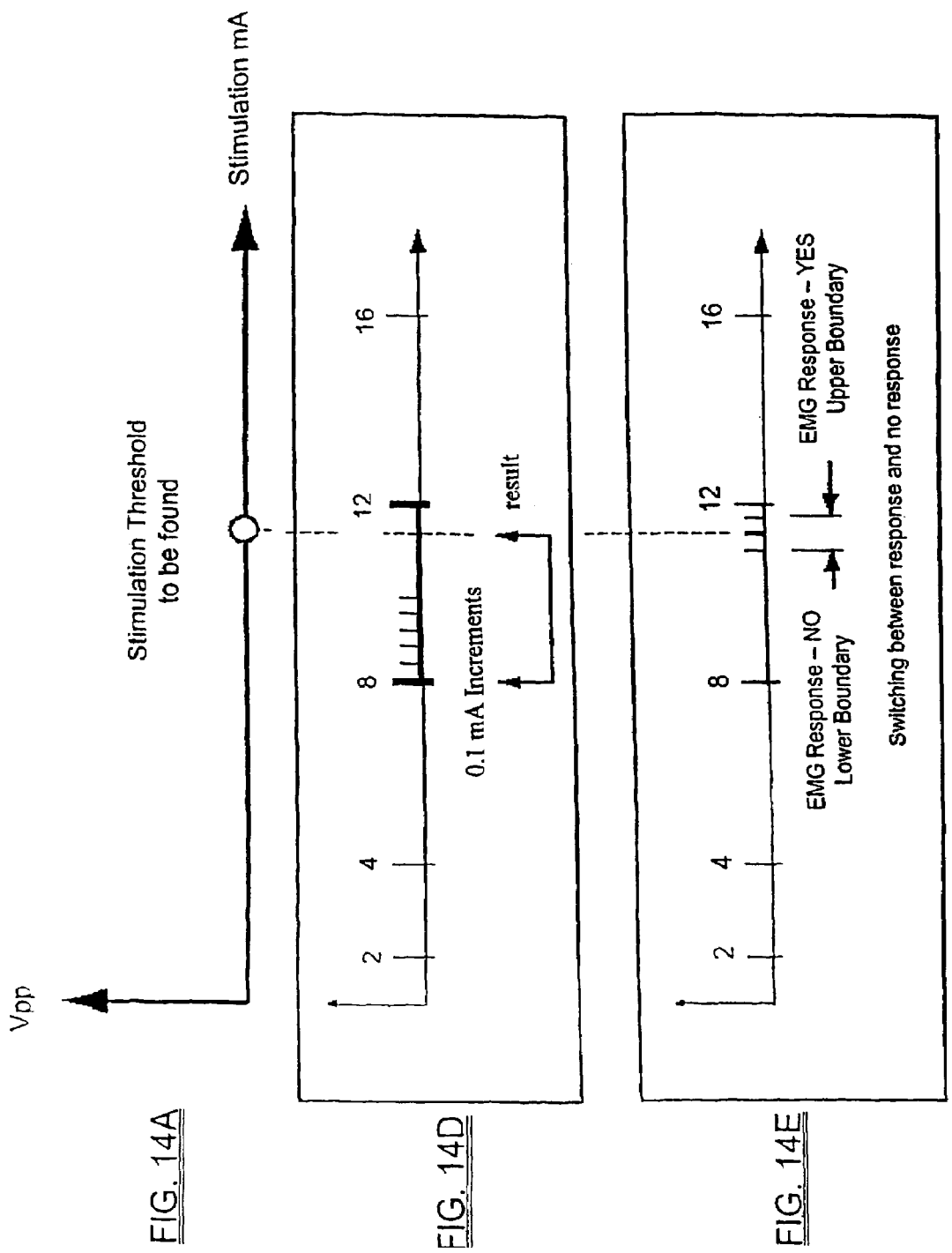

US 7,522,953 B2

SYSTEM AND METHODS FOR PERFORMING SURGICAL PROCEDURES AND ASSESSMENTS

CROSS-REFERENCES TO RELATED APPLICATIONS

This application is a continuation under 35 U.S.C. 111(a) of PCT Patent Application Ser. No. PCT/US02/30617, filed Sep. 25, 2002 and published on Apr. 3, 2003 as WO 03/026482 which is incorporated herein by reference and which claims the benefit of priority under 35 U.S.C. § 119(e) from U.S. Provisional Application Serial No. 60/325,424, filed Sep. 25, 2001.

BACKGROUND OF THE INVENTION

I. Field of the Invention

The present invention relates to a system and methods generally aimed at surgery. More particularly, the present invention is directed at a system and related methods for performing surgical procedures and assessments involving the use of neurophysiology.

II. Description of Related Art

A variety of surgeries involve establishing a working channel to gain access to a surgical target site. Oftentimes, based on the anatomical location of the surgical target site (as well as the approach thereto), the instruments required to form or create or maintain the working channel may have to pass near or close to nerve structures which, if contacted or disturbed, may be problematic to the patient. Examples of such "nerve sensitive" procedures may include, but are not necessarily limited to, spine surgery and prostrate or urology-related surgery.

Systems and methods exist for monitoring nerves and nerve muscles. One such system determines when a needle is approaching a nerve. The system applies a current to the needle to evoke a muscular response. The muscular response is visually monitored, typically as a shake or "twitch." When such a muscular response is observed by the user, the needle is considered to be near the nerve coupled to the responsive muscle. These systems require the user to observe the muscular response (to determine that the needle has approached the nerve). This may be difficult depending on the competing tasks of the user. In addition, when general anesthesia is used during a procedure, muscular response may be suppressed, limiting the ability of a user to detect the response.

While generally effective (although crude) in determining nerve proximity, such existing systems are incapable of determining the direction of the nerve to the needle or instrument passing through tissue or passing by the nerves. This can be disadvantageous in that, while the surgeon may appreciate that a nerve is in the general proximity of the instrument, the inability to determine the direction of the nerve relative to the instrument can lead to guess work by the surgeon in advancing the instrument and thereby raise the specter of inadvertent contact with, and possible damage to, the nerve.

Another nerve-related issue in existing surgical applications involves the use of nerve retractors. A typical nerve retractor serves to pull or otherwise maintain the nerve outside the area of surgery, thereby protecting the nerve from inadvertent damage or contact by the "active" instrumentation used to perform the actual surgery. While generally advantageous in protecting the nerve, it has been observed that such retraction can cause nerve function to become impaired or otherwise pathologic over time due to the retraction. In certain surgical applications, such as spinal surgery, it is not possible to determine if such retraction is hurting or damaging the retracted nerve until after the surgery (generally referred to as a change in "nerve health" or "nerve status"). There are also no known techniques or systems for assessing whether a given procedure is having a beneficial effect on a nerve or nerve root known to be pathologic (that is, impaired or otherwise unhealthy).

In spinal surgery, and specifically in spinal fusion procedures, a still further nerve-related issue exists with regard to assessing the placement of pedicle screws. More specifically, it has been found desirable to detect whether the medial wall of a pedicle has been breached (due to the formation of the hole designed to receive a pedicle screw or due to the placement of the pedicle screw into the hole) while attempting to effect posterior fixation for spinal fusion through the use of pedicle screws. Various attempts have been undertaken at assessing the placement of pedicle screws. X-ray and other imaging systems have been employed, but these are typically quite expensive and are oftentimes limited in terms of resolution (such that pedicle breaches may fail to be detected).

Still other attempts involve capitalizing on the insulating characteristics of bone (specifically, that of the medial wall of the pedicle) and the conductivity of the exiting nerve roots themselves. That is, if the medial wall of the pedicle is breached, a stimulation signal (voltage or current) applied to the pedicle screw and/or the pre-formed hole (prior to screw introduction) will cause the various muscle groups coupled to the exiting nerve roots to twitch. If the pedicle wall has not been breached, the insulating nature of the medial wall will prevent the stimulation signal from innervating the given nerve roots such that the muscle groups will not twitch.

To overcome this obviously crude technique (relying on visible muscles twitches), it has been proposed to employ electromyographic (EMG) monitoring to assess whether the muscle groups in the leg are innervating in response to the application of a stimulation signal to the pedicle screw and/or the pre-formed hole. This is advantageous in that it detects such evoked muscle action potentials (EMAPs) in the leg muscles as much lower levels than that via the "visual inspection" technique described above. However, the traditional EMG systems employed to date suffer from various drawbacks. First, traditional EMG systems used for pedicle screw testing are typically quite expensive. More importantly, they produce multiple waveforms that must be interpreted by a neurophysiologist. Even though performed by specialists, interpreting such multiple EMG waveforms in this fashion is nonetheless disadvantageously prone to human error and can be disadvantageously time consuming, adding to the duration of the operation and translating into increased health care costs. Even more costly is the fact that the neurophysiologist is required in addition to the actual surgeon performing the spinal operation.

The present invention is directed at eliminating, or at least reducing the effects of, the above-described problems with the prior art.

SUMMARY OF THE INVENTION

The present invention includes a system and related methods for performing surgical procedures and assessments, including the use of neurophysiology-based monitoring to: (a) determine nerve proximity and nerve direction to surgical instruments employed in accessing a surgical target site; (b) assess the pathology (health or status) of a nerve or nerve root before, during, or after a surgical procedure; and/or (c) assess pedicle integrity before, during or after pedicle screw placement, all in an automated, easy to use, and easy to interpret fashion so as to provide a surgeon-driven system.

The present invention accomplishes this by combining neurophysiology monitoring with any of a variety of instruments used in or in preparation for surgery (referred to herein as "surgical accessories"). By way of example only, such surgical accessories may include, but are not necessarily limited to, any number of devices or components for creating an operative corridor to a surgical target site (such as K-wires, sequentially dilating cannula systems, distractor systems, and/or retractor systems), devices or components for assessing pedicle integrity (such as a pedicle testing probe), and/or devices or components for retracting or otherwise protecting a nerve root before, during and/or after surgery (such as a nerve root retractor). Although described herein largely in terms of use in spinal surgery, it is to be readily appreciated that the teachings of the method and apparatus of the present invention are suitable for use in any number of additional surgical procedures wherein tissue having significant neural structures must be passed through (or near) in order to establish an operative corridor to a surgical target site, wherein neural structures are located adjacent bony structures, and/or wherein neural structures are retracted or otherwise contacted during surgery.

The fundamental method steps according to the present invention include: (a) stimulating one or more electrodes provided on a surgical accessory; (b) measuring the response of nerves innervated by the stimulation of step (a); (c) determining a relationship between the surgical accessory and the nerve based upon the response measured in step (b); and communicating this relationship to the surgeon in an easy-to-interpret fashion.

The step of stimulating may be accomplished by applying any of a variety of suitable stimulation signals to the electrode(s) on the surgical accessory, including voltage and/or current pulses of varying magnitude and/or frequency. The stimulating step may be performed at different times depending upon the particular surgical accessory in question. For example, when employed with a surgical access system, stimulation may be performed during and/or after the process of creating an operative corridor to the surgical target site. When used for pedicle integrity assessments, stimulation may be performed before, during and/or after the formation of the hole established to receive a pedicle screw, as well as before, during and/or after the pedicle screw is introduced into the hole. With regard to neural pathology monitoring, stimulation may be performed before, during and/or after retraction of the nerve root.

The step of measuring the response of nerves innervated by the stimulation step may be performed in any number of suitable fashions, including but not limited to the use of evoked muscle action potential (EMAP) monitoring techniques (that is, measuring the EMG responses of muscle groups associated with a particular nerve). According to one aspect of the present invention, the measuring step is preferably accomplished via monitoring or measuring the EMG responses of the muscles innervated by the nerve(s) stimulated in step for each of the preferred functions of the present invention: surgical access, pedicle integrity assessments, and neural pathology monitoring.

The step of determining a relationship between the surgical accessory and the nerve based upon the measurement step may be performed in any number of suitable fashions depending upon the manner of measuring the response, and may define the relationship in any of a variety of fashions (based on any number of suitable parameters and/or characteristics). By way of example only, the step of determining a relationship, within the context of a surgical access system, may involve identifying when (and preferably the degree to which) the surgical accessory comes into close proximity with a given nerve ("nerve proximity") and/or identifying the relative direction between the surgical accessory and the nerve ("nerve direction"). For a pedicle integrity assessment, the relationship between the surgical accessory (screw test probe) and the nerve is whether electrical communication is established therebetween. If electrical communication is established, this indicates that the medial wall of the pedicle has been cracked, stressed, or otherwise breached during the steps of hole formation and/or screw introduction. If not, this indicates that the integrity of the medial wall of the pedicle has remained intact during hole formation and/or screw introduction. This characteristic is based on the insulating properties of bone. For neural pathology assessments according to the present invention, the relationship may be, by way of example only, whether the neurophysiologic response of the nerve has changed over time. Such neurophysiologic responses may include, but are not necessarily limited to, the onset stimulation threshold for the nerve in question, the slope of the response vs. the stimulation signal for the nerve in question and/or the saturation level of the nerve in question. Changes in these parameters will indicate if the health or status of the nerve is improving or deteriorating, such as may result during surgery.

The step of communicating this relationship to the surgeon in an easy-to-interpret fashion may be accomplished in any number of suitable fashions, including but not limited to the use of visual indicia (such as alpha-numeric characters, light-emitting elements, and/or graphics) and audio communications (such as a speaker element). By way of example only, with regard to surgical access systems, this step of communicating the relationship may include, but is not necessarily limited to, visually representing the stimulation threshold of the nerve (indicating relative distance or proximity to the nerve), providing color coded graphics to indicate general proximity ranges (i.e. "green" for a range of stimulation thresholds above a predetermined safe value, "red" for range of stimulation thresholds below a predetermined unsafe value, and "yellow" for the range of stimulation thresholds in between the predetermined safe and unsafe values—designating caution), as well as providing an arrow or other suitable symbol for designating the relative direction to the nerve. This is an important feature of the present invention in that, by providing such proximity and direction information, a user will be kept informed as to whether a nerve is too close to a given surgical accessory element during and/or after the operative corridor is established to the surgical target site. This is particularly advantageous during the process of accessing the surgical target site in that it allows the user to actively avoid nerves and redirect the surgical access components to successfully create the operative corridor without impinging or otherwise compromising the nerves. Based on these nerve proximity and direction features, then, the present invention is capable of passing through virtually any tissue with minimal (if any) risk of impinging or otherwise damaging associated neural structures within the tissue, thereby making the present invention suitable for a wide variety of surgical applications.

With regard to pedicle integrity assessments, the step of communicating the relationship may include, but is not necessarily limited to, visually representing the actual stimulation threshold of an exiting nerve root alone or in combination with the stimulation threshold of a bare nerve root (with or without the difference therebetween), as well as with providing color coded graphics to indicate general ranges of pedicle integrity (i.e. "green" for a range of stimulation thresholds above a predetermined safe value—indicating "breach unlikely", "red" for range of stimulation thresholds below a predetermined unsafe value—indicating "breach likely", and "yellow" for the range of stimulation thresholds between the predetermined safe and unsafe values—indicating "possible breach"). This is a significant feature, and advantage over the prior art, in that it provides a straightforward and easy to interpret representation as to whether a pedicle has been breached during and/or after the process of forming the hole and/or introducing the pedicle screw. Identifying such a potential breach is helpful in that it prevents or minimizes the chance that a misplaced pedicle screw (that is, one breaching the medial wall) will be missed until after the surgery. Instead, any such misplaced pedicle screws, when stimulated according to the present invention, will produce an EMG response at a myotome level associated with the nerve in close proximity to the pedicle screw that is breaching the pedicle wall. This will indicate to the surgeon that the pedicle screw needs to be repositioned. But for this system and technique, patients may be released and subsequently experience pain due to the contact between the exiting nerve root and the pedicle screw, which oftentimes requires another costly and painful surgery.

As for neural pathology monitoring, the step of communicating the relationship may include, but is not necessarily limited to, visually representing the changes over time in the onset stimulation threshold of the nerve, the slope of the response versus the stimulation threshold of the nerve and/or the saturation level of the nerve. Once again, these changes may indicate if the health or status of the nerve is improving or deteriorating, such as may result during surgery and/or retraction. This feature is important in that it may provide qualitative feedback on the effect of the particular surgery. If it appears the health or status (pathology) of the nerve is deteriorating over time, the user may be instructed to stop or lessen the degree of retraction to avoid such deterioration. If the pathology of the nerve improves over time, it may indicate the success of the surgery in restoring or improving nerve function, such as may be the case in decompressive spinal surgery.

The present invention also encompasses a variety of techniques, algorithms, and systems for accomplishing the steps of (a) stimulating one or more electrodes provided on a surgical accessory; (b) measuring the response of nerves innervated by the stimulation of step (a); (c) determining a relationship between the surgical accessory and the nerve based upon the response measured in step (b); and/or communicating this relationship to the surgeon in an easy-to-interpret fashion.

BRIEF DESCRIPTION OF THE DRAWINGS

FIGS. 14A-14E are graphs illustrating a current threshold-hunting algorithm according to one embodiment of the present invention;

DESCRIPTION OF THE SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

The present invention is capable of performing a variety of surgical procedures and assessments by combining neurophysiology monitoring with any of a variety of instruments used in or in preparation for surgery (referred to herein as "surgical accessories"). By way of example only, such surgical accessories may include, but are not necessarily limited to, any number of devices or components for creating an operative corridor to a surgical target site (such as K-wires, sequentially dilating cannula systems, distractor systems, and/or retractor systems), for retracting or otherwise protecting a nerve root before, during and/or after surgery (such as a nerve root retractor), and/or for assessing pedicle integrity (such as a pedicle screw test probe). Although described herein largely in terms of use in spinal surgery, it is to be readily appreciated that the teachings of the method and apparatus of the present invention are suitable for use in any number of additional surgical procedures wherein tissue having significant neural structures must be passed through (or near) in order to establish an operative corridor to a surgical target site, wherein neural structures are retracted, and/or wherein neural structures are located adjacent bony structures.

Figure 1:
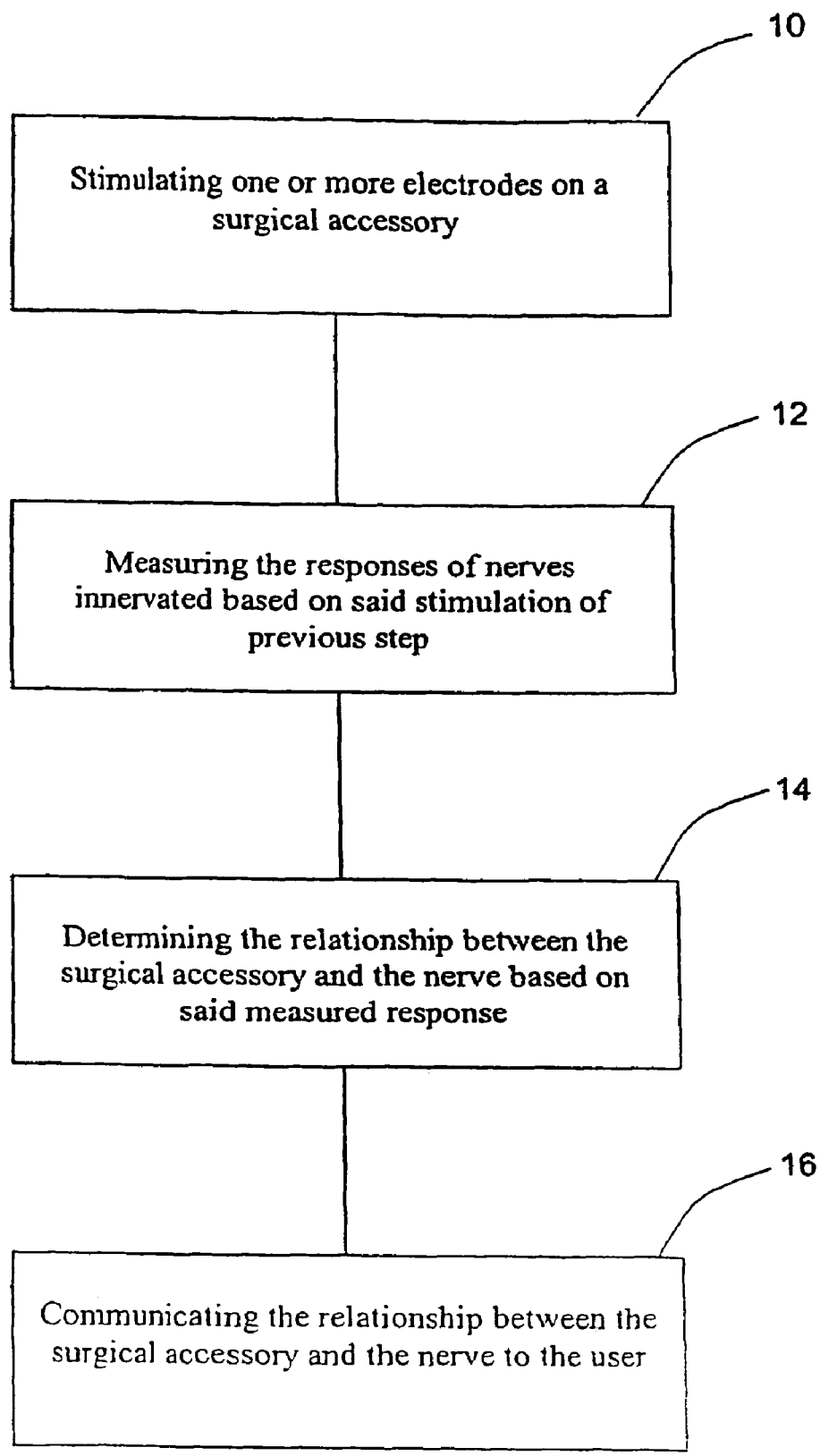
FIG. 1 is a flow chart illustrating the fundamental steps of the neurophysiology-based surgical system according to the present invention.

FIG. 1 illustrates the fundamental method steps according to the present invention, namely: (a) stimulating one or more electrodes provided on a surgical accessory; (b) measuring the response of nerves innervated by the stimulation of step (a); (c) determining a relationship between the surgical accessory and the nerve based upon the response measured in step (b); and (d) communicating this relationship to the surgeon in an easy-to-interpret fashion.

The step of stimulating may be accomplished by applying any of a variety of suitable stimulation signals to the electrode(s) on the surgical accessory, including voltage and/or current pulses of varying magnitude and/or frequency. The stimulating step may be performed at different times depending upon the particular surgical accessory in question. For example, when employed with a surgical access system, stimulation 10 may be performed during and/or after the process of creating an operative corridor to the surgical target site. When used for pedicle integrity assessments, stimulation 10 may be performed before, during and/or after the formation of the hole established to receive a pedicle screw, as well as before, during and/or after the pedicle screw is introduced into the hole. With regard to neural pathology monitoring, stimulation 10 may be performed before, during and/or after retraction of the nerve root.

The step of measuring the response of nerves innervated by the stimulation step 10 may be performed in any number of suitable fashions, including but not limited to the use of evoked muscle action potential (EMAP) monitoring techniques (that is, measuring the EMG responses of muscle groups associated with a particular nerve). According to one aspect of the present invention, the measuring step is preferably accomplished via monitoring or measuring the EMG responses of the muscles innervated by the nerve(s) stimulated in step (a) for each of the preferred functions of the present invention: surgical access, pedicle integrity assessments, and neural pathology monitoring.

The step of determining a relationship between the surgical accessory and the nerve based upon the measurement step (b) may be performed in any number of suitable fashions depending upon the manner of measuring the response of step (b), and may define the relationship in any of a variety of fashions (based on any number of suitable parameters and/or characteristics). By way of example only, step (c) of determining a relationship, within the context of a surgical access system, may involve identifying when (and preferably the degree to which) the surgical accessory comes into close proximity with a given nerve ("nerve proximity") and/or identifying the relative direction between the surgical accessory and the nerve ("nerve direction"). For a pedicle integrity assessment, the relationship between the surgical accessory (screw test probe) and the nerve is whether electrical communication is established therebetween. If electrical communication is established, this indicates that the medial wall of the pedicle has been cracked, stressed, or otherwise breached during the steps of hole formation and/or screw introduction. If not, this indicates that the integrity of the medial wall of the pedicle has remained intact during hole formation and/or screw introduction. This characteristic is based on the insulating properties of bone. For neural pathology assessments according to the present invention, the step (c) relationship may be, by way of example only, whether the neurophysiologic response of the nerve has changed over time. Such neurophysiologic responses may include, but are not necessarily limited to, the onset stimulation threshold for the nerve in question, the slope of the response vs. the stimulation signal for the nerve in question and/or the saturation level of the nerve in question. Changes in these parameters will indicate if the health or status of the nerve is improving or deteriorating, such as may result during surgery.

The step of communicating this relationship to the surgeon in an easy-to-interpret fashion may be accomplished in any number of suitable fashions, including but not limited to the use of visual indicia (such as alpha-numeric characters, light-emitting elements, and/or graphics) and audio communications (such as a speaker element). By way of example only, with regard to surgical access systems, step (d) of communicating the relationship may include, but is not necessarily limited to, visually representing the stimulation threshold of the nerve (indicating relative distance or proximity to the nerve), providing color coded graphics to indicate general proximity ranges (i.e. "green" for a range of stimulation thresholds above a predetermined safe value, "red" for range of stimulation thresholds below a predetermined unsafe value, and "yellow" for the range of stimulation thresholds in between the predetermined safe and unsafe values—designating caution), as well as providing an arrow or other suitable symbol for designating the relative direction to the nerve. This is an important feature of the present invention in that, by providing such proximity and direction information, a user will be kept informed as to whether a nerve is too close to a given surgical accessory element during and/or after the operative corridor is established to the surgical target site. This is particularly advantageous during the process of accessing the surgical target site in that it allows the user to actively avoid nerves and redirect the surgical access components to successfully create the operative corridor without impinging or otherwise compromising the nerves. Based on these nerve proximity and direction features, then, the present invention is capable of passing through virtually any tissue with minimal (if at all) risk of impinging or otherwise damaging associated neural structures within the tissue, thereby making the present invention suitable for a wide variety of surgical applications.

With regard to pedicle integrity assessments, step (d) of communicating the relationship may include, but is not necessarily limited to, visually representing the actual stimulation threshold of an exiting nerve root alone or in combination with the stimulation threshold of a bare nerve root (with or without the difference therebetween), as well as with providing color coded graphics to indicate general ranges of pedicle integrity (i.e. "green" for a range of stimulation thresholds above a predetermined safe value—indicating "breach unlikely", "red" for range of stimulation thresholds below a predetermined unsafe value—indicating "breach likely", and "yellow" for the range of stimulation thresholds between the predetermined safe and unsafe values—indicating "possible breach"). This is a significant feature, and advantage over the prior art, in that it provides a straightforward and easy to interpret representation as to whether a pedicle has been breached during and/or after the process of forming the hole and/or introducing the pedicle screw. Identifying such a potential breach is helpful in that it prevents or minimizes the chance that a misplaced pedicle screw (that is, one breaching a wall of the pedicle, such as, by way of example, the medial wall) will be missed until after the surgery. Instead, any such misplaced pedicle screws, when stimulated according to the present invention, will produce an EMG response at a myotome level associated with the nerve in close proximity to the pedicle screw that is breaching the pedicle wall. This will indicate to the surgeon that the pedicle screw needs to be repositioned. But for this system and technique, patients may be released and subsequently experience pain due to the contact between the exiting nerve root and the pedicle screw, which oftentimes requires another costly and painful surgery.

As for neural pathology monitoring, step (d) of communicating the relationship may include, but is not necessarily limited to, visually representing the changes over time in the onset stimulation threshold of the nerve, the slope of the response versus the stimulation threshold of the nerve and/or the saturation level of the nerve. Once again, these changes may indicate if the health or status of the nerve is improving or deteriorating, such as may result during surgery and/or retraction. This feature is important in that it may provide qualitative feedback on the effect of the particular surgery. If it appears the health or status (pathology) of the nerve is deteriorating over time, the user may be instructed to stop or lessen the degree of retraction to avoid such deterioration. If the pathology of the nerve improves over time, it may indicate the success of the surgery in restoring or improving nerve function, such as may be the case in decompressive spinal surgery.

Figure 2:
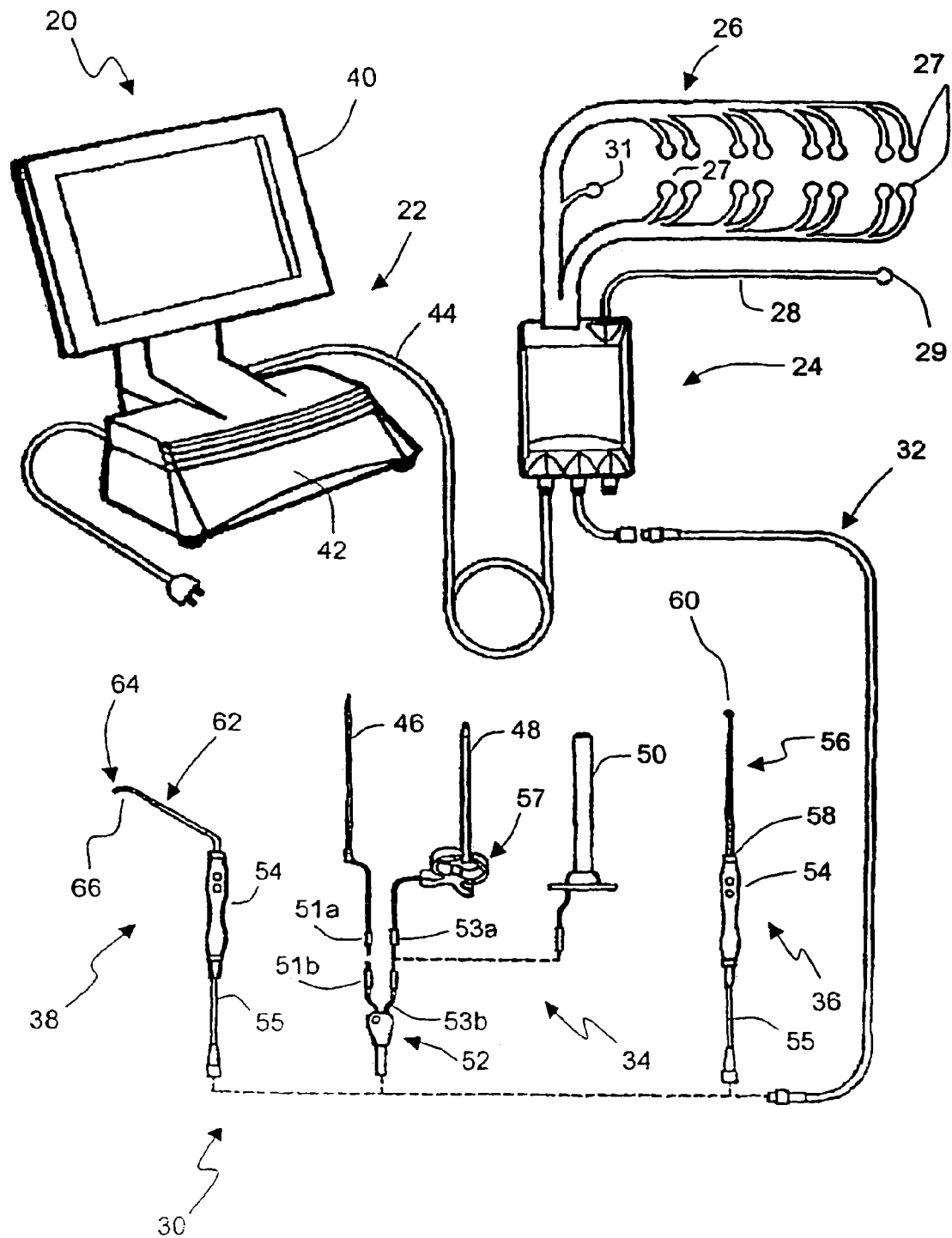
FIG. 2 is a perspective view of an exemplary surgical system 20 capable of determining nerve proximity and direction to surgical instruments employed in accessing a surgical target site, assessing pedicle integrity before, during or after pedicle screw placement, and/or assessing the pathology (health and/or status) of a nerve or nerve root before, during, or after a surgical procedure.
Figure 3:
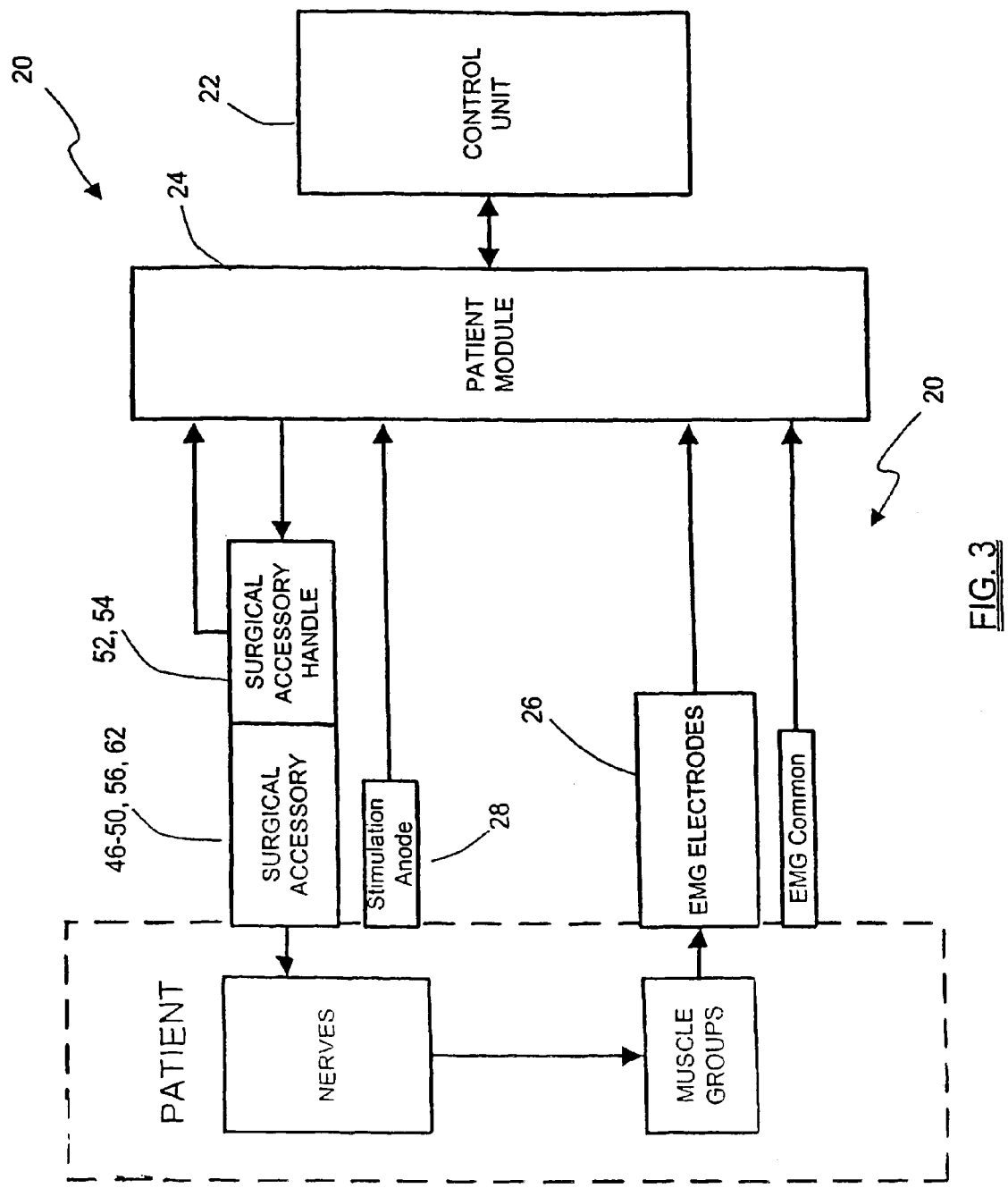
FIG. 3 is a block diagram of the surgical system 20 shown in FIG. 2.

FIGS. 2-3 illustrate, by way of example only, a surgical system 20 provided in accordance with a broad aspect of the present invention. The surgical system 20 includes a control unit 22, a patient module 24, an EMG harness 26 and return electrode 28 coupled to the patient module 24, and a host of surgical accessories 30 capable of being coupled to the patient module 24 via one or more accessory cables 32. In the embodiment shown, the surgical accessories 30 include (by way of example only) a sequential dilation access system 34, a pedicle testing assembly 36, and a nerve root retractor assembly 38. The control unit 22 includes a touch screen display 40 and a base 42, which collectively contain the essential processing capabilities for controlling the surgical system 20. The patient module 24 is connected to the control unit 22 via a data cable 44, which establishes the electrical connections and communications (digital and/or analog) between the control unit 22 and patient module 24. The main functions of the control unit 22 include receiving user commands via the touch screen display 40, activating stimulation in the requested mode (nerve proximity, nerve direction, screw test, and nerve pathology), processing signal data according to defined algorithms (described below), displaying received parameters and processed data, and monitoring system status and report fault conditions. The touch screen display 40 is preferably equipped with a graphical user interface (GUI) capable of communicating information to the user and receiving instructions from the user. The display 40 and/or base 42 may contain patient module interface circuitry that commands the stimulation sources, receives digitized signals and other information from the patient module 24, processes the EMG responses to extract characteristic information for each muscle group, and displays the processed data to the operator via the display 40.

As will be described in greater detail below, the surgical system 20 is capable of performing one or more of the following functions: (1) determination of nerve proximity and/or nerve direction relative to the sequential dilation access system 34 during and following the creation of an operative corridor to surgical target site; (2) assessment of pedicle integrity after hole formation and/or after pedicle screw placement via the pedicle testing assembly 36; and/or (3) assessment of nerve pathology (health or status) before, during, and/or after a surgical procedure via the nerve root retractor assembly 38. Surgical system 20 accomplishes this by having the control unit 22 and patient module 24 cooperate to send stimulation signals to one or more stimulation electrodes on the various surgical accessories 30. Depending upon the location of the surgical accessories within a patient, the stimulation signals may cause nerves adjacent to or in the general proximity of the surgical accessories 30 to innervate, which, in turn, can be monitored via the EMG harness 26. The nerve proximity and direction, pedicle integrity, and nerve pathology features of the present invention are based on assessing the evoked response of the various muscle myotomes monitored by the surgical system 20 via EMG harness 26.

The sequential dilation access system 34 comprises, by way of example only, a K-wire 46, one or more dilating cannula 48, and a working cannula 50. As will be explained in greater detail below, these components 46-50 are designed to bluntly dissect the tissue between the patient's skin and the surgical target site. In an important aspect of the present invention, the K-wire 46, dilating cannula 48 and/or working cannula 50 may be equipped with one or more stimulation electrodes to detect the presence and/or location of nerves in between the skin of the patient and the surgical target site. To facilitate this, a surgical hand-piece 52 is provided for electrically coupling the surgical accessories 46-50 to the patient module 24 (via accessory cable 32). In a preferred embodiment, the surgical hand piece 42 includes one or more buttons for selectively initiating the stimulation signal (preferably, a current signal) from the control unit 12 to a particular surgical access component 46-50. Stimulating the electrode(s) on these surgical access components 46-50 during passage through tissue in forming the operative corridor will cause nerves that come into close or relative proximity to the surgical access components 46-50 to depolarize, producing a response in the innervated myotome. By monitoring the myotomes associated with the nerves (via the EMG harness 26 and recording electrode 27) and assessing the resulting EMG responses (via the control unit 22), the sequential dilation access system 34 is capable of detecting the presence (and optionally direction to) such nerves, thereby providing the ability to actively negotiate around or past such nerves to safely and reproducibly form the operative corridor to a particular surgical target site. In one embodiment, the sequential dilation access system 34 is particularly suited for establishing an operative corridor to an intervertebral target site in a postero-lateral, trans-psoas fashion so as to avoid the bony posterior elements of the spinal column.

The pedicle testing assembly 36 includes a surgical accessory handle assembly 54 and a pedicle probe 56. The handle assembly 54 includes a cable 55 for establishing electrical communication with the patient module 24 (via the accessory cable 32). In a preferred embodiment, the pedicle probe 56 may be selectively removed from the handle assembly 54, such as by unscrewing a threaded cap 58 provided on the distal end of the handle assembly 54 (through which the proximal end of the pedicle probe 56 passes). The pedicle probe 56 includes a ball-tipped distal end 60 suitable for introduction into a pedicle hole (after hole formation but before screw insertion) and/or for placement on the head of a fully introduced pedicle screw. In both situations, the user may operate one or more buttons of the handle assembly 54 to selectively initiate a stimulation signal (preferably, a current signal) from the patient module 24 to the pedicle probe 56. With the pedicle probe 56 touching the inner wall of the pedicle hole and/or the fully introduced pedicle screw, applying a stimulation signal in this fashion serves to test the integrity of the medial wall of the pedicle. That is, a breach or compromise in the integrity of the pedicle will allow the stimulation signal to pass through the pedicle and innervate an adjacent nerve root. By monitoring the myotomes associated with the nerve roots (via the EMG harness 26 and recording electrode 27) and assessing the resulting EMG responses (via the control unit 22), the surgical system 20 can assess whether a pedicle breach occurred during hole formation and/or screw introduction. If a breach or potential breach is detected, the user may simply withdraw the misplaced pedicle screw and redirect to ensure proper placement.

The nerve root retractor assembly 38, in a preferred embodiment, comprises the same style surgical accessory handle assembly 54 as employed with in the pedicle testing assembly 36, with a selectively removable nerve root retractor 62. The nerve root retractor 62 has a generally angled orientation relative to the longitudinal axis of the handle assembly 54, and includes a curved distal end 64 having a generally arcuate nerve engagement surface 66 equipped with one or more stimulation electrodes (not shown). In use, the nerve root retractor 62 is introduced into or near a surgical target site in order to hook and retract a given nerve out of the way. According to the present invention, the nerve root may be stimulated (monopolar or bipolar) before, during, and/or after retraction in order to assess the degree to which such retraction impairs or otherwise degrades nerve function over time. To do so, the user may operate one or more buttons of the handle assembly 54 to selectively transmit a stimulation signal (preferably, a current signal) from the patient module 24 to the electrode(s) on the engagement surface 66 of the nerve root retractor 62. By monitoring the myotome associated with the nerve root being retracted (via the EMG harness 26) and assessing the resulting EMG responses (via the control unit 22), the surgical system 20 can assess whether (and the degree to which) such retraction impairs or adversely affects nerve function over time. With this information, a user may wish to periodically release the nerve root from retraction to allow nerve function to recover, thereby preventing or minimizing the risk of long-term or irreversible nerve impairment. As will be described in greater detail below, a similar neural pathology assessment can be undertaken, whereby an unhealthy nerve may be monitored to determine if nerve function improves due to a particular surgical procedure, such as spinal nerve decompression surgery.

A discussion of the algorithms and principles behind the neurophysiology for accomplishing these functions will now be undertaken, followed by a detailed description of the various implementations of these principles according to the present invention.

Figure 5:
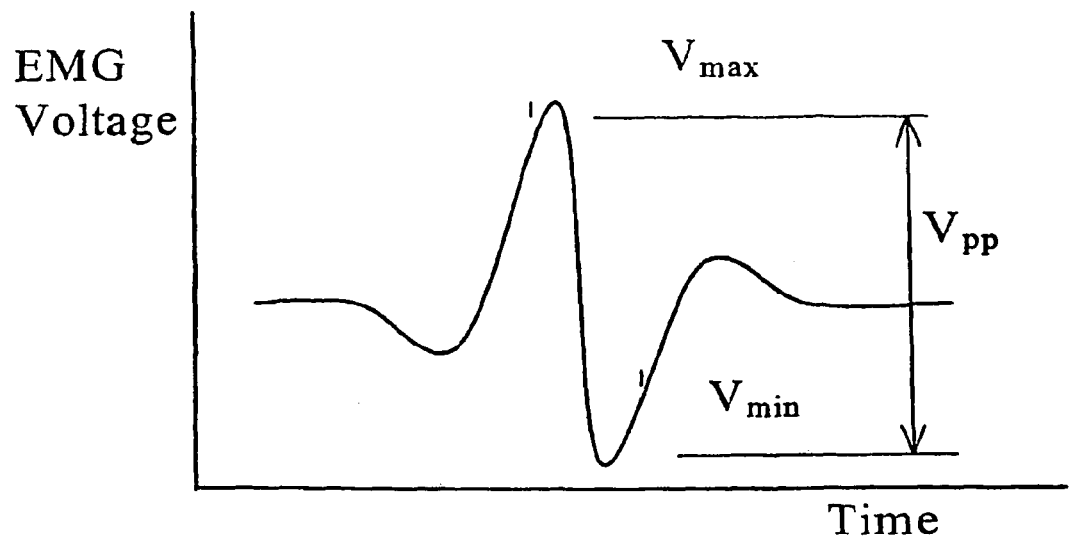
FIG. 5 is a graph illustrating a plot of the neuromuscular response (EMG) of a given myotome over time based on a current stimulation pulse (such as shown in FIG. 4) applied to a nerve bundle coupled to the given myotome.
Figure 4:
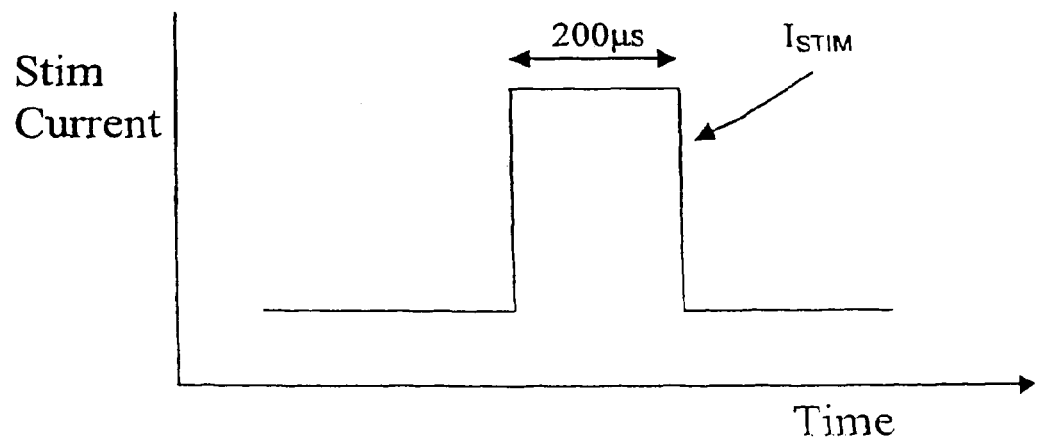
FIG. 4 is a graph illustrating a plot of a stimulation current pulse capable of producing a neuromuscular response (EMG) of the type shown in FIG. 3.

FIGS. 4 and 5 illustrate a fundamental aspect of the present invention: a stimulation signal (FIG. 4) and a resulting evoked response (FIG. 5). By way of example only, the stimulation signal is preferably a stimulation current signal ($I_{Stim}$) having rectangular monophasic pulses with a frequency and amplitude adjusted by system software. In a still further preferred embodiment, the stimulation current ($I_{Stim}$) may be coupled in any suitable fashion (i.e. AC or DC) and comprises rectangular monophasic pulses of 200 microsecond duration. The amplitude of the current pulses may be fixed, but will preferably sweep from current amplitudes of any suitable range, such as from 2 to 100 mA. For each nerve and myotome there is a characteristic delay from the stimulation current pulse to the EMG response (typically between 5 to 20 ms). To account for this, the frequency of the current pulses is set at a suitable level such as, in a preferred embodiment, 4 Hz to 10 Hz (and most preferably 4.5 Hz), so as to prevent stimulating the nerve before it has a chance to recover from depolarization. The EMG response shown in FIG. 5 can be characterized by a peak-to-peak voltage of $V_{pp}=V_{max}-V_{min}$.

Figure 6:
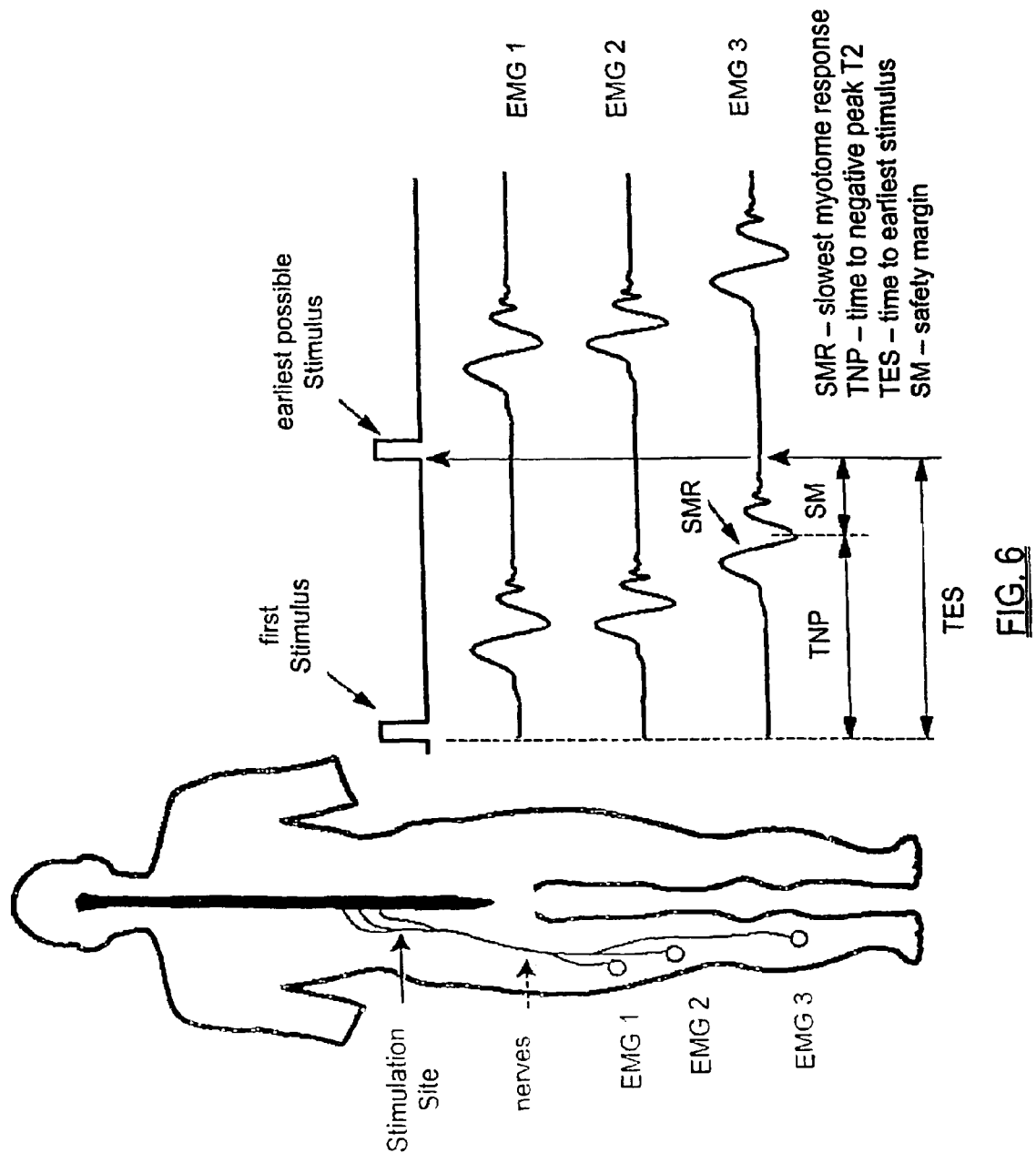
FIG. 6 is an illustrating (graphical and schematic) of a method of automatically determining the maximum frequency ($F_{Max}$) of the stimulation current pulses according to one embodiment of the present invention.

FIG. 6 illustrates an alternate manner of setting the maximum stimulation frequency, to the extent it is desired to do so rather than simply selecting a fixed maximum stimulation frequency (such as 4.5 Hz) as described above. According to this embodiment, the maximum frequency of the stimulation pulses is automatically adjusted. After each stimulation, Fmax will be computed as: $Fmax=1/(T2+T_{Safety\ Margin})$ for the largest value of T2 from each of the active EMG channels. In one embodiment, the Safety Margin is 5 ms, although it is contemplated that this could be varied according to any number of suitable durations. Before the specified number of stimulations, the stimulations will be performed at intervals of 100-120 ms during the bracketing state, intervals of 200-240 ms during the bisection state, and intervals of 400-480 ms during the monitoring state. After the specified number of stimulations, the stimulations will be performed at the fastest interval practical (but no faster than Fmax) during the bracketing state, the fastest interval practical (but no faster than Fmax/2) during the bisection state, and the fastest interval practical (but no faster than Fmax/4) during the monitoring state. The maximum frequency used until $F_{max}$ is calculated is preferably 10 Hz, although slower stimulation frequencies may be used during some acquisition algorithms. The value of $F_{max}$ used is periodically updated to ensure that it is still appropriate. For physiological reasons, the maximum frequency for stimulation will be set on a per-patient basis. Readings will be taken from all myotomes and the one with the slowest frequency (highest T2) will be recorded.

Figure 7:
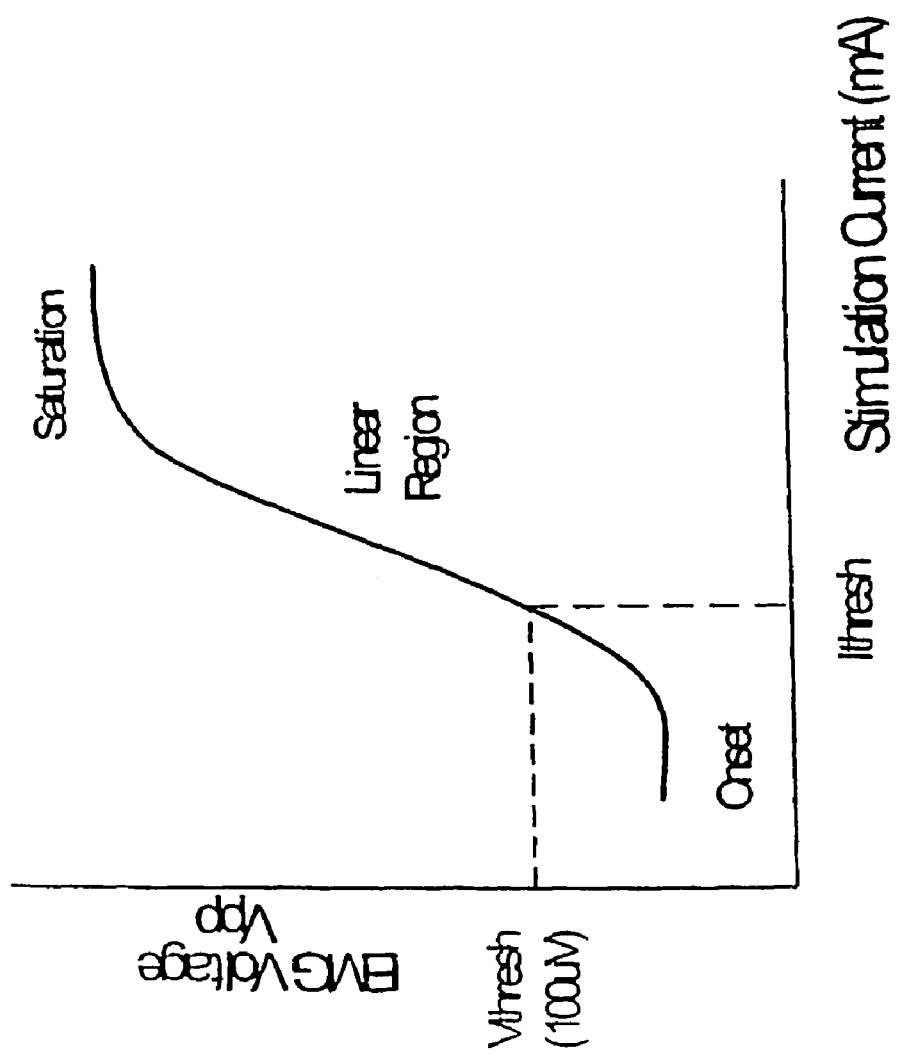
FIG. 7 is a graph illustrating a plot of EMG response peak-to-peak voltage (Vpp) for each given stimulation current level ($I_{Stim}$) forming a stimulation current pulse according to the present invention (otherwise known as a "recruitment curve")

A basic premise behind the neurophysiology employed in the present invention is that each nerve has a characteristic threshold current level ($I_{Thresh}$) at which it will depolarize. Below this threshold, current stimulation will not evoke a significant EMG response ($V_{pp}$). Once the stimulation threshold ($I_{Thresh}$) is reached, the evoked response is reproducible and increases with increasing stimulation until saturation is reached. This relationship between stimulation current and EMG response may be represented graphically via a so-called "recruitment curve," such as shown in FIG. 7, which includes an onset region, a linear region, and a saturation region. By way of example only, the present invention defines a significant EMG response to have a Vpp of approximately 100 uV. In a preferred embodiment, the lowest stimulation current that evokes this threshold voltage ($V_{Thresh}$) is called $I_{Thresh}$. As will be described in greater detail below, changes in the current threshold ($I_{Thresh}$) over time may indicate that the relative distance between the nerve and the stimulation electrode is changing (indicating nerve migration towards the surgical accessory having the stimulation electrode and/or movement of the surgical accessory towards the nerve). This is useful in performing proximity assessments between the electrode and the nerve according to an aspect of the present invention. Changes in the current threshold ($I_{Thresh}$) may also be indicative of a change in the degree of electrical communication between a stimulation electrode and a nerve. This may be helpful, by way of example, in assessing if a screw or similar instrument has inadvertently breached the medial wall of a pedicle. More specifically, where an initial determination of ($I_{Thresh}$), such as by applying a stimulation current to the interior of a hole created to receive a pedicle screw, is greater than a later determination of ($I_{Thresh}$), such as by applying a stimulation current to the tip of the pedicle screw after insertion, the decrease in $I_{Thresh}$, if large enough, may indicate electrical communication between the pedicle screw and the nerve. Based on the insulation properties of bone, such electrical communication would indicate a breach of the pedicle. As will also be in greater detail below, changes in the current threshold ($I_{Thresh}$), the slope of the linear region, and the saturation level over time are indicative of changes in the pathology (that is, health or status) of a given nerve. This is useful in assessing the effects of surgery on an unhealthy nerve (such as decompression surgery) as well as assessing the effects of nerve retraction on a healthy nerve (so as to prevent or minimize the risk of damage due to retraction).

Figure 8:
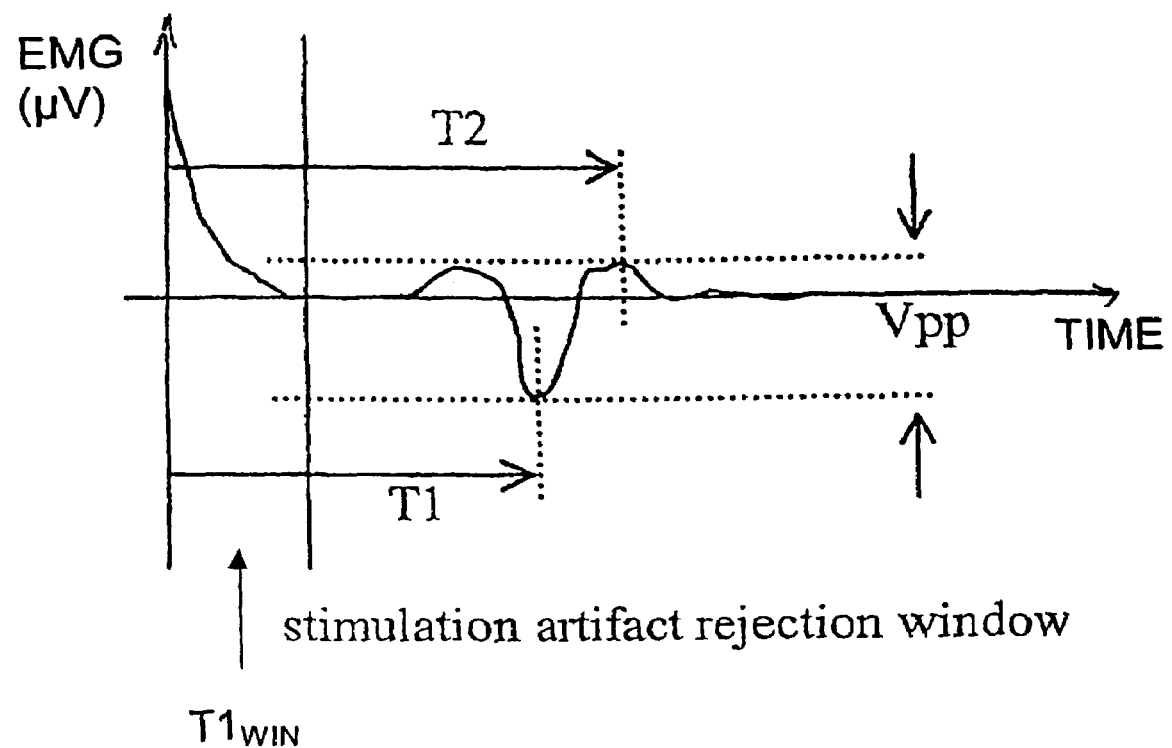
FIG. 8 is a graph illustrating a traditional stimulation artifact rejection technique as may be employed in obtaining each peak-to-peak voltage (Vpp) EMG response according to the present invention.
Figure 9:
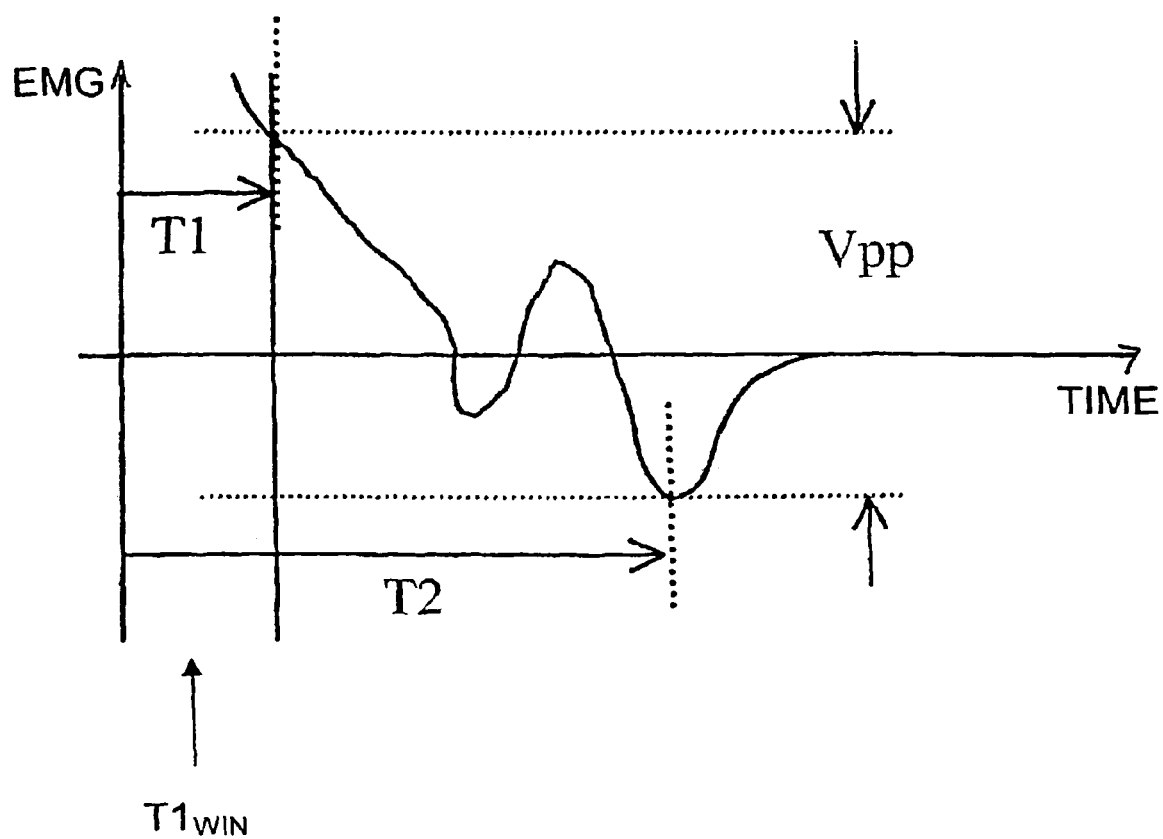
FIG. 9 is a graph illustrating the traditional stimulation artifact rejection technique of FIG. 8, wherein a large artifact rejection causes the EMG response to become compromised.

In order to obtain this useful information, the present invention must first identify the peak-to-peak voltage (Vpp) of each EMG response corresponding a given stimulation current ($I_{Stim}$). The existence stimulation and/or noise artifacts, however, can conspire to create an erroneous Vpp measurement of the electrically evoked EMG response. To overcome this challenge, the surgical system 20 of the present invention may employ any number of suitable artifact rejection techniques, including the traditional stimulation artifact rejection technique shown in FIG. 8. Under this technique, stimulation artifact rejection is undertaken by providing a simple artifact rejection window T1$_{WIN}$ at the beginning of the EMG waveform. During this T1 window, the EMG waveform is ignored and Vpp is calculated based on the max and min values outside this window. (T1 is the time of the first extremum (min or max) and T2 is the time of the second extremum.) In one embodiment, the artifact rejection window T1$_{WIN}$ may be set to about 7.3 msec. While generally suitable, there are situations where this stimulation artifact rejection technique of FIG. 8 is not optimum, such as in the presence of a large stimulation artifact (see FIG. 9). The presence of a large stimulation artifact causes the stimulation artifact to cross over the window T1$_{WIN}$ and blend in with the EMG. Making the stimulation artifact window larger is not effective, since there is no clear separation between EMG and stimulation artifact.

Figure 10:
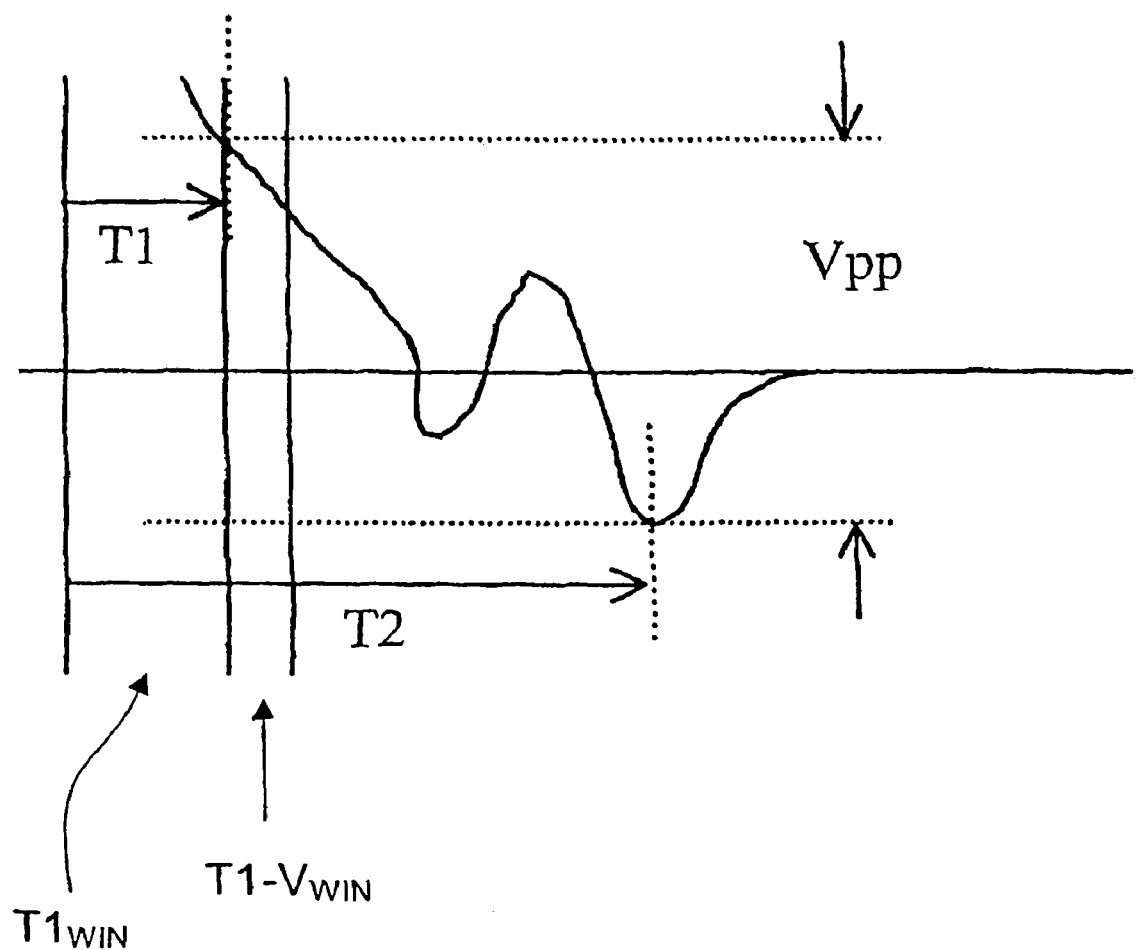
FIG. 10 is a graph illustrating an improved stimulation artifact rejection technique according to the present invention.

FIG. 10 illustrates a stimulation artifact rejection technique according to the present invention, which solves the above-identified problem with traditional stimulation artifact rejection. Under this technique, a T1 validation window (T1–V$_{WIN}$) is defined immediately following the T1 window (T1$_{WIN}$). If the determined Vpp exceeds the threshold for recruiting, but T1 falls within this T1 validation window, then the stimulation artifact is considered to be substantial and the EMG is considered to have not recruited. An operator may be alerted, based on the substantial nature of the stimulation artifact. This method of stimulation artifact rejection is thus able to identify situations where the stimulation artifact is large enough to cause the Vpp to exceed the recruit threshold. To account for noise, the T1 validation window (T1–V$_{WIN}$) should be within the range of 0.1 ms to 1 ms wide (preferably about 0.5 ms). The T1 validation window (T1–V$_{WIN}$) should not be so large that the T1 from an actual EMG waveform could fall within.

Figure 11:
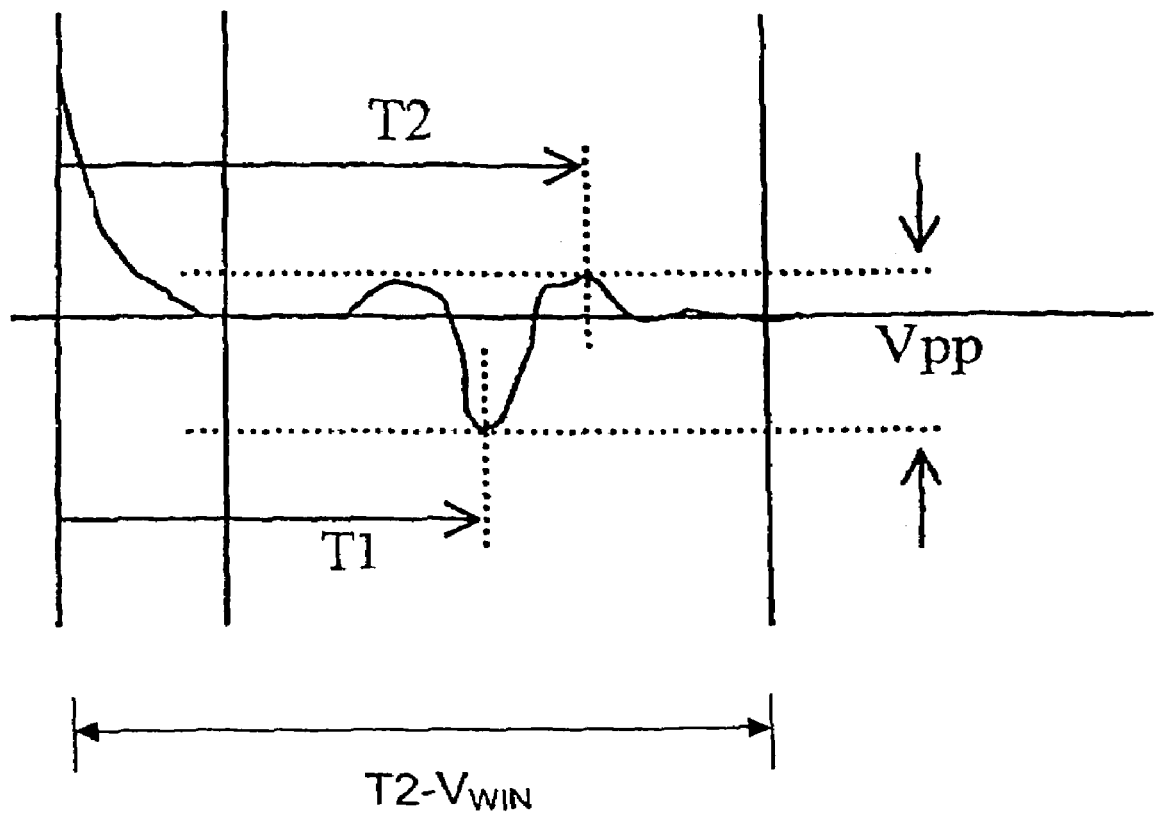
FIG. 11 is a graph illustrating an improved noise artifact rejection technique according to the present invention.

FIG. 11 illustrates a noise artifact rejection technique according to the present invention. When noise artifacts fall in the time window where an EMG response is expected, their presence can be difficult to identify. Artifacts outside the expected response window, however, are relatively easy to identify. The present invention capitalizes on this and defines a T2 validation window (T2–V$_{WIN}$) analogous to the T1 validation window (T1–V$_{WIN}$) described above with reference to FIG. 10. As shown, T2 must occur prior to a defined limit, which, according to one embodiment of the present invention, may be set having a range of between 40 ms to 50 ms (preferably about 47 ms). If the Vpp of the EMG response exceeds the threshold for recruiting, but T2 falls beyond the T2 validation window (T2–V$_{WIN}$), then the noise artifact is considered to be substantial and the EMG is considered to have not recruited. An operator may be alerted, based on the substantial nature of the noise artifact.

Figure 12:
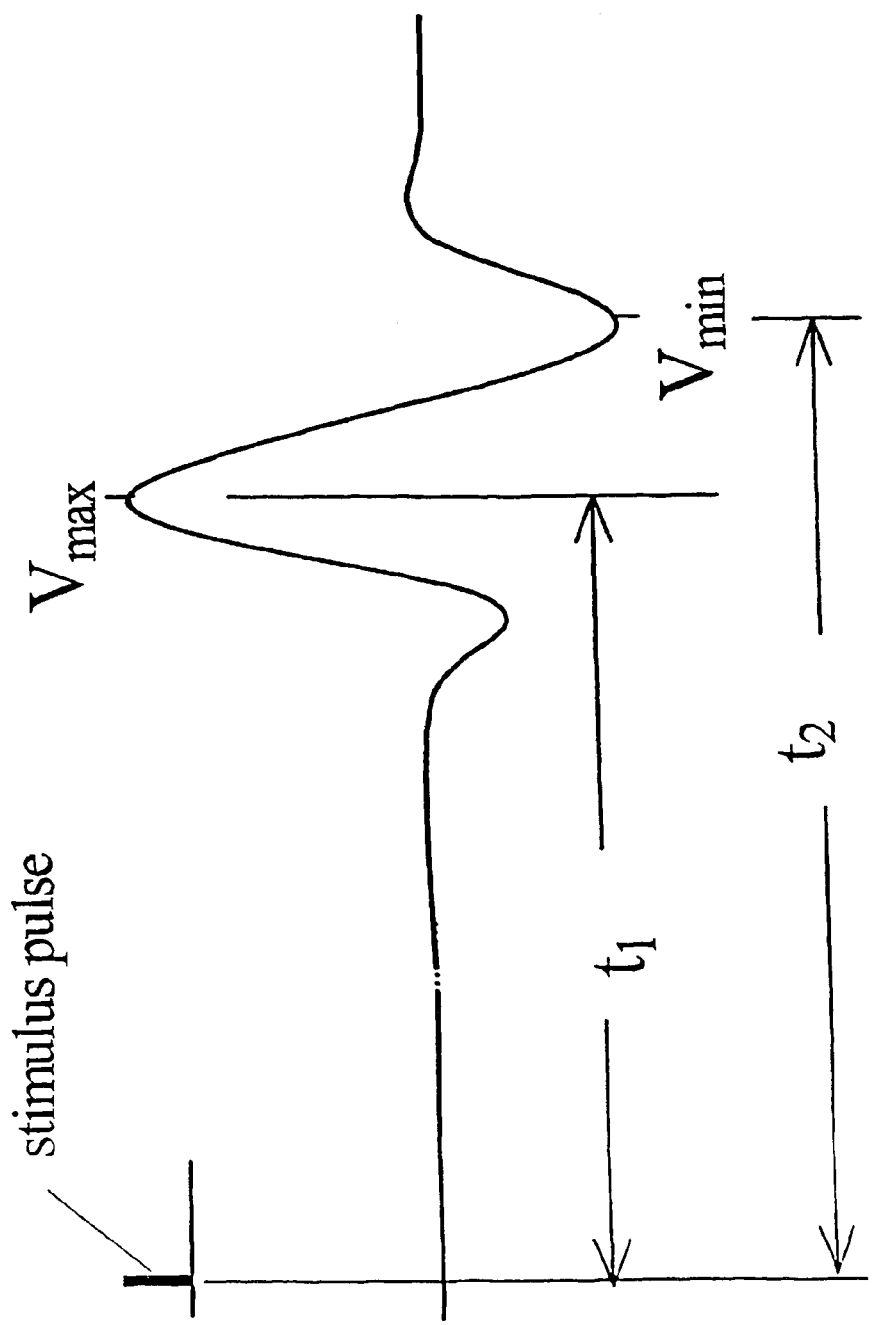
FIG. 12 is a graph illustrating a plot of a neuromuscular response (EMG) over time (in response to a stimulus current pulse) showing the manner in which voltage extrema ($V_{Max\ or\ Min}$), ($V_{Min\ or\ Max}$) occur at times T1 and T2, respectively.
Figure 13:
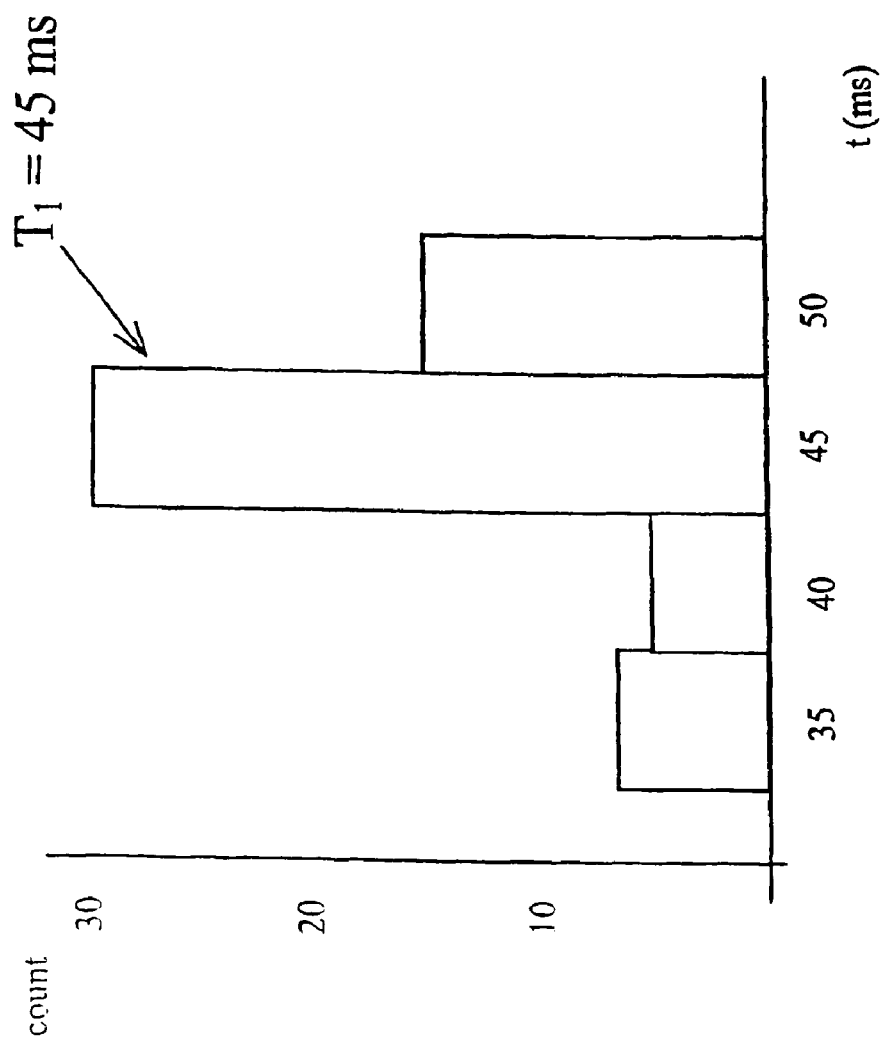
FIG. 13 is a graph illustrating a histogram as may be employed as part of a T1, T2 artifact rejection technique according to an alternate embodiment of the present invention.

FIG. 12 illustrates a still further manner of performing stimulation artifact rejection according to an alternate embodiment of the present invention. This artifact rejection is premised on the characteristic delay from the stimulation current pulse to the EMG response. For each stimulation current pulse, the time from the current pulse to the first extremum (max or min) is $T_1$ and to the second extremum (max or min) is $T_2$. As will be described below, the values of $T_1$, $T_2$ are each compiled into a histogram period (see FIG.

13). New values of $T_1$, $T_2$ are acquired for each stimulation and the histograms are continuously updated. The value of $T_1$, and $T_2$ used is the center value of the largest bin in the histogram. The values of $T_1$, $T_2$ are continuously updated as the histograms change. Initially Vpp is acquired using a window that contains the entire EMG response. After 20 samples, the use of $T_1$, $T_2$ windows is phased in over a period of 200 samples. Vmax and Vmin are then acquired only during windows centered around $T_1$, $T_2$ with widths of, by way of example only, 5 msec. This method of acquiring $V_{pp}$ automatically rejects the artifact if $T_1$, or $T_2$ fall outside of their respective windows.

Having measured each Vpp EMG response (as facilitated by the stimulation and/or noise artifact rejection techniques described above), this Vpp information is then analyzed relative to the stimulation current in order to determine a relationship between the nerve and the given surgical accessory transmitting the stimulation current. More specifically, the present invention determines these relationships (between nerve and surgical accessory) by identifying the minimum stimulation current ($I_{Thresh}$) capable of resulting in a predetermined Vpp EMG response. According to the present invention, the determination of $I_{Thresh}$ may be accomplished via any of a variety of suitable algorithms or techniques.

FIGS. 14A-14E illustrate, by way of example only, a threshold-hunting algorithm for quickly finding the threshold current ($I_{Thresh}$) for each nerve being stimulated by a given stimulation current ($I_{Stim}$). Threshold current ($I_{Thresh}$), once again, is the minimum stimulation current ($I_{Stim}$) that results in a Vpp that is greater than a known threshold voltage ($V_{Thresh}$). The value of is adjusted by a bracketing method as follows. The first bracket is 0.2 mA and 0.3 mA. If the Vpp corresponding to both of these stimulation currents is lower than Vthresh, then the bracket size is doubled to 0.2 mA and 0.4 mA. This doubling of the bracket size continues until the upper end of the bracket results in a Vpp that is above Vthresh. The size of the brackets is then reduced by a bisection method. A current stimulation value at the midpoint of the bracket is used and if this results in a Vpp that is above Vthresh, then the lower half becomes the new bracket. Likewise, if the midpoint Vpp is below Vthresh then the upper half becomes the new bracket. This bisection method is used until the bracket size has been reduced to $I_{Thresh}$ mA. $I_{Thresh}$ may be selected as a value falling within the bracket, but is preferably defined as the midpoint of the bracket.

The threshold-hunting algorithm of this embodiment will support three states: bracketing, bisection, and monitoring. A stimulation current bracket is a range of stimulation currents that bracket the stimulation current threshold $I_{Thresh}$. The width of a bracket is the upper boundary value minus the lower boundary value. If the stimulation current threshold $I_{Thresh}$ of a channel exceeds the maximum stimulation current, that threshold is considered out-of-range. During the bracketing state, threshold hunting will employ the method below to select stimulation currents and identify stimulation current brackets for each EMG channel in range.

The method for finding the minimum stimulation current uses the methods of bracketing and bisection. The "root" is identified for a function that has the value −1 for stimulation currents that do not evoke adequate response; the function has the value +1 for stimulation currents that evoke a response. The root occurs when the function jumps from −1 to +1 as stimulation current is increased: the function never has the value of precisely zero. The root will not be known exactly, but only with a level of precision related to the minimum bracket width. The root is found by identifying a range that must contain the root. The upper bound of this range is the lowest stimulation current $I_{Thresh}$ where the function returns the value +1, i.e. the minimum stimulation current that evokes response. The lower bound of this range is the highest stimulation current $I_{Thresh}$ where the function returns the value −1, i.e. the maximum stimulation current that does not evoke a response.

Figures 14A, 14B, 14C:
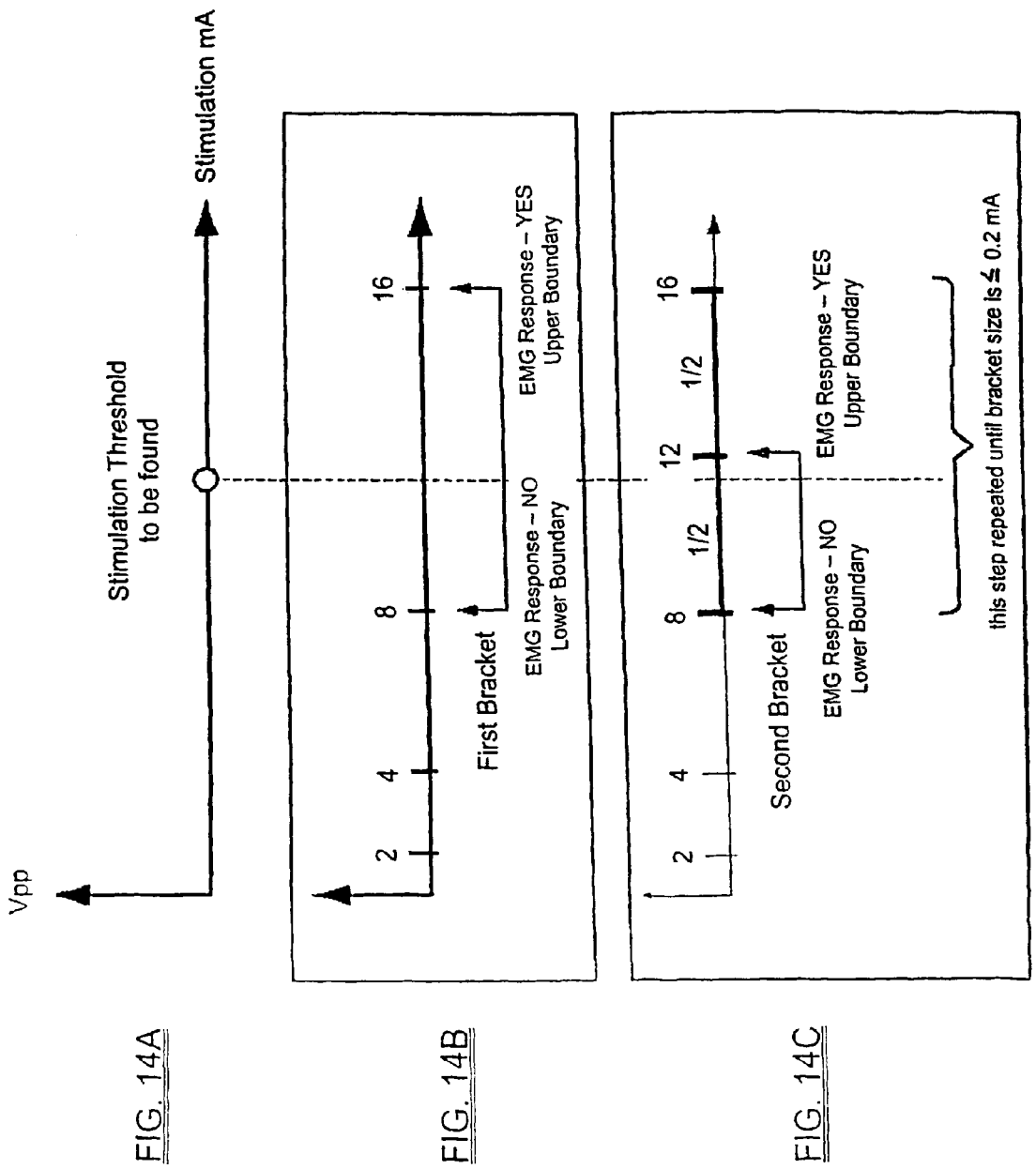

The proximity function begins by adjusting the stimulation current until the root is bracketed (FIG. 14B). The initial bracketing range may be provided in any number of suitable ranges. In one embodiment, the initial bracketing range is 0.2 to 0.3 mA. If the upper stimulation current does not evoke a response, the upper end of the range should be increased. The range scale factor is 2. The stimulation current should preferably not be increased by more than 10 mA in one iteration. The stimulation current should preferably never exceed the programmed maximum stimulation current. For each stimulation, the algorithm will examine the response of each active channel to determine whether it falls within that bracket. Once the stimulation current threshold of each channel has been bracketed, the algorithm transitions to the bisection state.

During the bisection state (FIGS. 14C and 14D), threshold hunting will employ the method described below to select stimulation currents and narrow the bracket to a selected width (for example, 0.1 mA) for each EMG channel with an in-range threshold. After the minimum stimulation current has been bracketed (FIG. 14B), the range containing the root is refined until the root is known with a specified accuracy. The bisection method is used to refine the range containing the root. In one embodiment, the root should be found to a precision of 0.1 mA. During the bisection method, the stimulation current at the midpoint of the bracket is used. If the stimulation evokes a response, the bracket shrinks to the lower half of the previous range. If the stimulation fails to evoke a response, the bracket shrinks to the upper half of the previous range. The proximity algorithm is locked on the electrode position when the response threshold is bracketed by stimulation currents separated by the selected width (i.e. 0.1 mA). The process is repeated for each of the active channels until all thresholds are precisely known. At that time, the algorithm enters the monitoring state.

During the monitoring state (FIG. 14E), threshold hunting will employ the method described below to select stimulation currents and identify whether stimulation current thresholds are changing. In the monitoring state, the stimulation current level is decremented or incremented by 0.1 mA, depending on the response of a specific channel. If the threshold has not changed then the lower end of the bracket should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm may transition back to the bracketing state in order to reestablish the bracket.

Figure 15:
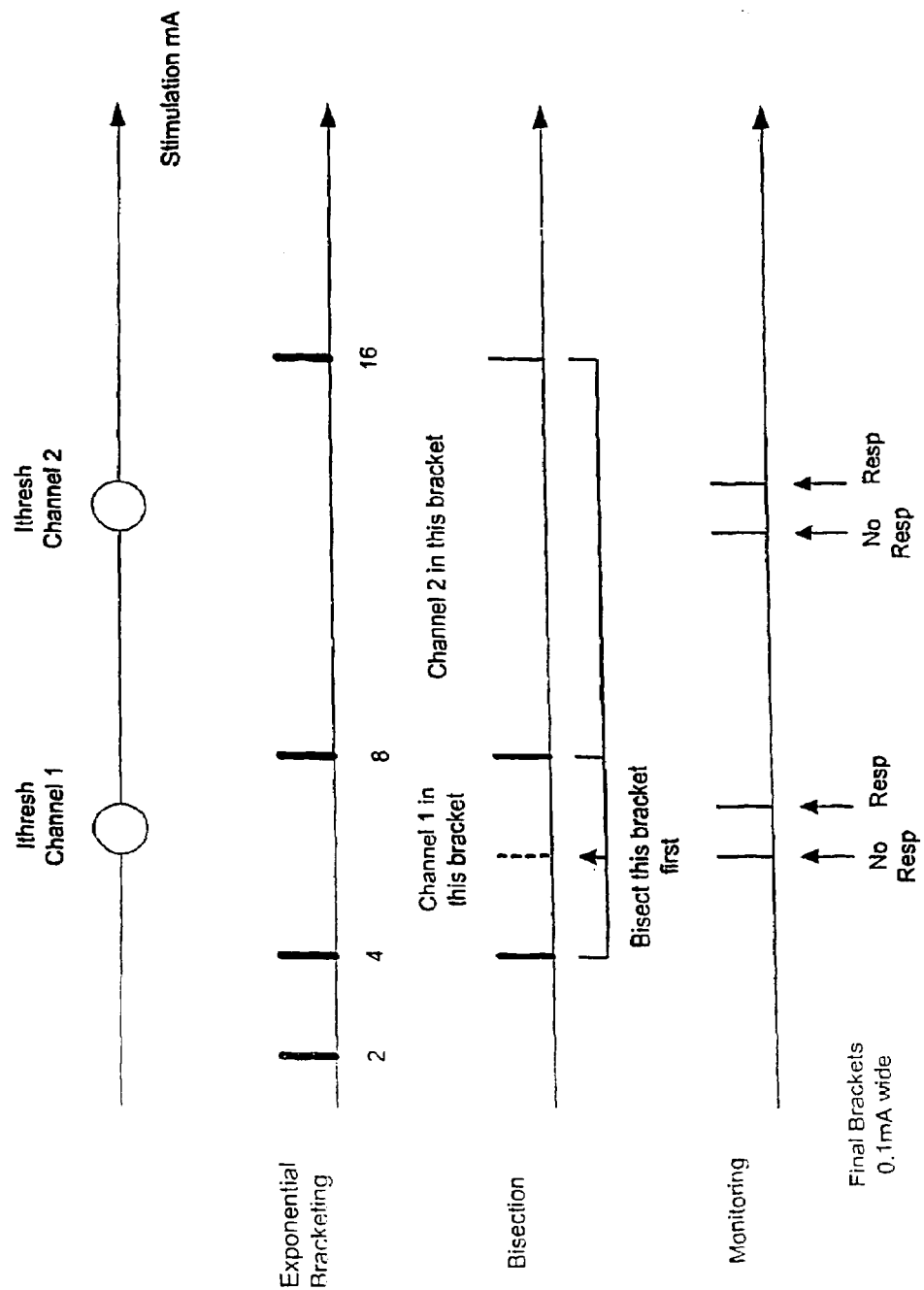
FIG. 15 is a series of graphs illustrating a multi-channel current threshold-hunting algorithm according to one embodiment of the present invention.

When it is necessary to determine the stimulation current thresholds ($I_{Thresh}$) for more than one channel, they will be obtained by time-multiplexing the threshold-hunting algorithm as shown in FIG. 15. During the bracketing state, the algorithm will start with a stimulation current bracket of 0.2 mA and increase the size of the bracket. With each bracket, the algorithm will measure the Vpp of all channels to determine which bracket they fall into. After this first pass, the algorithm will determine which bracket contains the $I_{Thresh}$ for each channel. Next, during the bisection state, the algorithm will start with the lowest bracket that contains an $I_{Thresh}$ and bisect it until $I_{Thresh}$ is found within 0.1 mA. If there are more than one $I_{Thresh}$ within a bracket, they will be separated out during the bisection process, and the one with the lowest value will be found first. During the monitoring state, the algorithm will monitor the upper and lower boundaries of the brackets for each $I_{Thresh}$, starting with the lowest. If the $I_{Thresh}$ for one or more channels is not found in it's bracket, then the algorithm goes back to the bracketing state to re-establish the bracket for those channels.

A still further manner of performing multi-channel threshold hunting is described as follows, with reference to FIGS. 14-15. This technique monitors multiple channels but reports the result for a single channel. The user chooses one of two channel selection modes: auto or manual. In the manual channel selection mode, the system will track the stimulation threshold $I_{Thresh}$ for a single EMG channel, as shown in FIG. 14. In the auto channel selection mode, the system will monitor responses on a set of channels and track to the lowest responding channel. The auto mode permits the user to select the set of channels to track. Individual channels can be added or subtracted from the set at any time. Tracking to the lowest responding channel is performed in this fashion. First, after stimulation, if no channels in the selected set respond, then the stimulation current is below the lowest responding channel. If any channels respond, then the stimulation current is above the lowest responding channel. Coupling this logic with the bracketing, bisection, and monitoring technique described above allows the system to track to the lowest responding channel, and do so in a quick and accurate fashion.

If during monitoring, the tracked channel falls out of the bracket, or if any channel responds at the low end of the bracket, then the bracket will be expanded again, as before, until the lowest responding channel is bracketed again. However, unlike the embodiments shown in FIGS. 14 and 15, the bracket is expanded in situ rather than beginning again from the start. For example, a bracket of 4.5 to 4.6 mA that fails to recruit at both levels is expanded to higher currents. First, the bracket width is doubled from 0.1 mA to 0.2 mA, resulting in stimulation current at 4.7 mA. If this fails to recruit, the bracket is again doubled to 0.4 mA, with stimulation current at 4.9 mA. The pattern continues with stimulations at 5.3, 6.1, and 9.3 mA, corresponding to bracket sizes of 0.8, 1.6, and 3.2 mA, until the threshold is bracketed. If a response is evoked at both ends of the original bracket, the same bracket-doubling technique is used moving toward lower stimulation currents.

The reason for doubling the bracket size each time is to identify the threshold current with as few stimulations as practical. The reason for starting the bracket doubling in situ rather than starting over from zero is twofold: (1) to take advantage of threshold information that is already known, and (2) it is more likely that the current threshold has not moved far from where it was previously bracketed. The advantage of tracking only to the lowest channel is that it provides the most relevant nerve proximity information with fewer stimulation pulses than multi-channel detection as with that shown in FIG. 15. This is an advantage because fewer stimulation pulses means a faster responding system, with the goal being to be able to track movement of the stimulation electrode in real time.

After identifying the threshold current $I_{Thresh}$, this information may be employed to determine any of a variety of relationships between the surgical accessory and the nerve. For example, as will be described in greater detail below, determining the current threshold $I_{Thresh}$ of a nerve while using a surgical access system (such as the sequential dilation system 34 of FIG. 2) may involve determining when (and preferably the degree to which) the surgical accessory comes into close proximity with a given nerve ("nerve proximity") and/or identifying the relative direction between the surgical accessory and the nerve ("nerve direction"). For a pedicle integrity assessment, the relationship between the pedicle testing assembly 36 and the nerve is whether electrical communication is established therebetween. If electrical communication is established, this indicates that the medial wall of the pedicle has been cracked, stressed, or otherwise breached during the steps of hole formation and/or screw introduction. If not, this indicates that the integrity of the medial wall of the pedicle has remained intact during hole formation and/or screw introduction. This characteristic is based on the insulating properties of bone. For neural pathology assessments according to the present invention, the relationship may be, by way of example only, whether the neurophysiologic response of the nerve has changed over time. Such neurophysiologic responses may include, but are not necessarily limited to, the onset stimulation threshold for the nerve in question, the slope of the response vs. the stimulation signal for the nerve in question and/or the saturation level of the nerve in question. Changes in these parameters will indicate if the health or status of the nerve is improving or deteriorating, such as may result during surgery or nerve retraction.

In a significant aspect of the present invention, the relationships determined above based on the current threshold determination may be communicated to the user in an easy to use format, including but not limited to, alpha-numeric and/or graphical information regarding mode of operation, nerve proximity, nerve direction, nerve pathology, pedicle integrity assessments, stimulation level, EMG responses, advance or hold instructions, instrument in use, set-up, and related instructions for the user. This advantageously provides the ability to present simplified yet meaningful data to the user, as opposed to the actual EMG waveforms that are displayed to the users in traditional EMG systems. Due to the complexity in interpreting EMG waveforms, such prior art systems typically require an additional person specifically trained in such matters which, in turn, can be disadvantageous in that it translates into extra expense (having yet another highly trained person in attendance) and oftentimes presents scheduling challenges because most hospitals do not retain such personnel.

Having described the fundamental aspects of the neurophysiology principles and algorithms of the present invention, various implementations according to the present invention will now be described.

I. Surgical Access: Nerve Proximity and Direction

FIGS. 2-3 illustrate an exemplary embodiment of the surgical system 20 of the present invention, including the sequential dilation access system 34. The sequential dilation access system 34 of the present invention is capable of accomplishing safe and reproducible access to a surgical target site. It does so by detecting the existence of (and optionally the distance and/or direction to) neural structures before, during, and after the establishment of an operative corridor through (or near) any of a variety of tissues having such neural structures, which, if contacted or impinged, may otherwise result in neural impairment for the patient. The surgical system 20 does so by electrically stimulating nerves via one or more stimulation electrodes at the distal end of the surgical access components 46-50 while monitoring the EMG responses of the muscle groups innervated by the nerves.

In one embodiment, the surgical system 20 accomplishes this through the use of the surgical hand-piece 52, which may be electrically coupled to the K-wire 46 via a first cable connector 51a, 51b and to either the dilating cannula 48 or the working cannula 50 via a second cable connector 53a, 53b.

For the K-wire 46 and working cannula 50, cables are directly connected between these accessories and the respective cable connectors 51a, 53a for establishing electrical connection to the stimulation electrode(s). In one embodiment, a pincher or clamp-type device 57 is provided to selectively establish electrical communication between the surgical hand-piece 52 and the stimulation electrode(s) on the distal end of the cannula 48. This is accomplished by providing electrical contacts on the inner surface of the opposing arms forming the clamp-type device 57, wherein the contacts are dimensioned to be engaged with electrical contacts (preferably in a male-female engagement scenario) provided on the dilating cannula 48 and working cannula 50. The surgical hand-piece 52 includes one or more buttons such that a user may selectively direct a stimulation current signal from the control unit 22 to the electrode(s) on the distal ends of the surgical access components 46-50. In an important aspect, each surgical access component 46-50 is insulated along its entire length, with the exception of the electrode(s) at their distal end (and, in the case of the dilating cannula 48 and working cannula 50, the electrical contacts at their proximal ends for engagement with the clamp 57). The EMG responses corresponding to such stimulation may be monitored and assessed according to the present invention in order to provide nerve proximity and/or nerve direction information to the user.

When employed in spinal procedures, for example, such EMG monitoring would preferably be accomplished by connecting the EMG harness 26 to the myotomes in the patient's legs corresponding to the exiting nerve roots associated with the particular spinal operation level. In a preferred embodiment, this is accomplished via 8 pairs of EMG electrodes 27 placed on the skin over the major muscle groups on the legs (four per side), an anode electrode 29 providing a return path for the stimulation current, and a common electrode 31 providing a ground reference to pre-amplifiers in the patient module 24. Although not shown, it will be appreciated that any of a variety of electrodes can be employed, including but not limited to needle electrodes. The EMG responses measured via the EMG harness 26 provide a quantitative measure of the nerve depolarization caused by the electrical stimulus. By way of example, the placement of EMG electrodes 27 may be undertaken according to the manner shown in Table 1 below for spinal surgery:

TABLE 1

| Color | Channel ID | Myotome | Spinal Level |
| --- | --- | --- | --- |
| Blue | Right 1 | Right Vastus Medialis | L2, L3, L4 |
| Violet | Right 2 | Right Tibialis Anterior | L4, L5 |
| Grey | Right 3 | Right Biceps Femoris | L5, S1, S2 |
| White | Right 4 | Right Gastroc. Medial | S1, S2 |
| Red | Left 1 | Left Vastus Medialis | L2, L3, L4 |
| Orange | Left 2 | Left Tibialis Anterior | L4, L5 |
| Yellow | Left 3 | Left Biceps Femoris | L5, S1, S2 |
| Green | Left 4 | Left Gastroc. Medial | S1, S2 |

Figure 16:
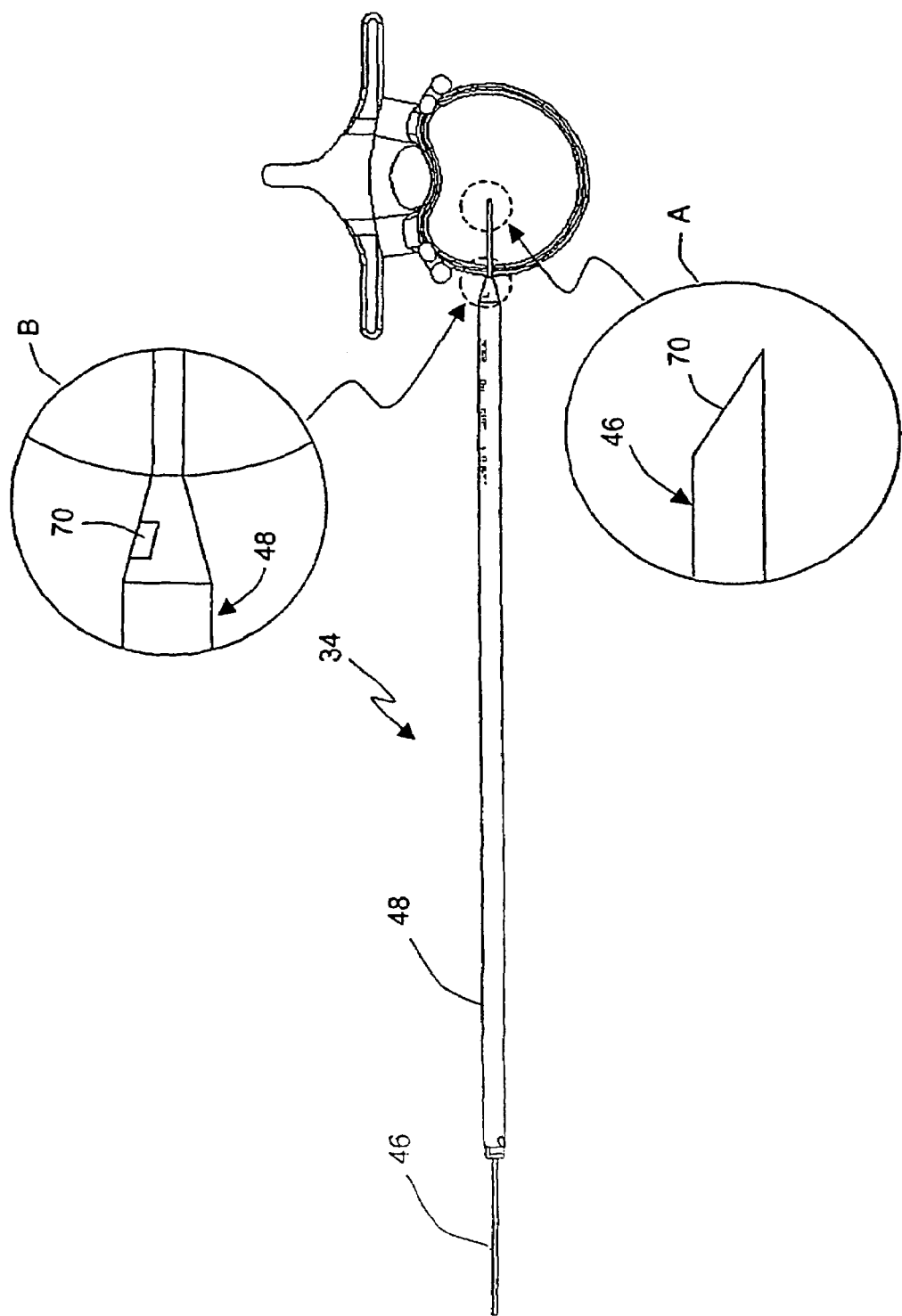
FIGS. 16-19 are top views of a neurophysiology-based surgical access system according to one embodiment of the present invention in use accessing a surgical target site in the spine.

FIGS. 16-19 illustrate the sequential dilation access system 34 of the present invention in use creating an operative corridor to an intervertebral disk. As shown in FIG. 16, an initial dilating cannula 48 is advanced towards the target site with the K-wire 46 disposed within an inner lumen within the dilating cannula 48. This may be facilitated by first aligning the K-wire 46 and initial dilating cannula 48 using any number of commercially available surgical guide frames. In one embodiment, as best shown in the expanded insets A and B, the K-wire 46 and initial dilating cannula 48 are each equipped with a single stimulation electrode 70 to detect the presence and/or location of nerves in between the skin of the patient and the surgical target site. More specifically, each electrode 70 is positioned at an angle relative to the longitudinal axis of the K-wire 46 and dilator 48 (and working cannula 50). In one embodiment, this angle may range from 5 to 85 degrees from the longitudinal axis of these surgical access components 46-50. By providing each stimulation electrode 70 in this fashion, the stimulation current will be directed angularly from the distal tip of the respective accessory 46, 48. This electrode configuration is advantageous in determining proximity, as well as direction, according to the present invention in that a user may simply rotate the K-wire 46 and/or dilating cannula 48 while stimulating the electrode 70. This may be done continuously or step-wise, and preferably while in a fixed axial position. In either case, the user will be able to determine the location of nerves by viewing the proximity information on the display screen 40 and observing changes as the electrode 70 is rotated. This may be facilitated by placing a reference mark (not shown) on the K-wire 46 and/or dilator 48 (or a control element coupled thereto), indicating the orientation of the electrode 70 to the user.

Figure 17:
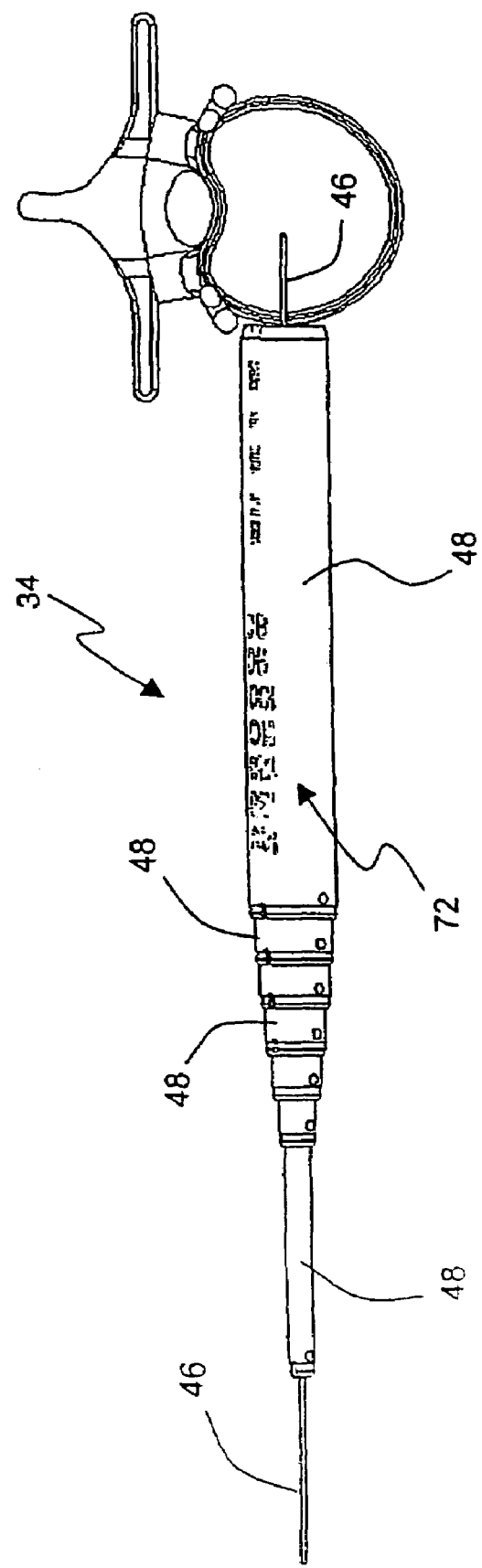
Figure 18:
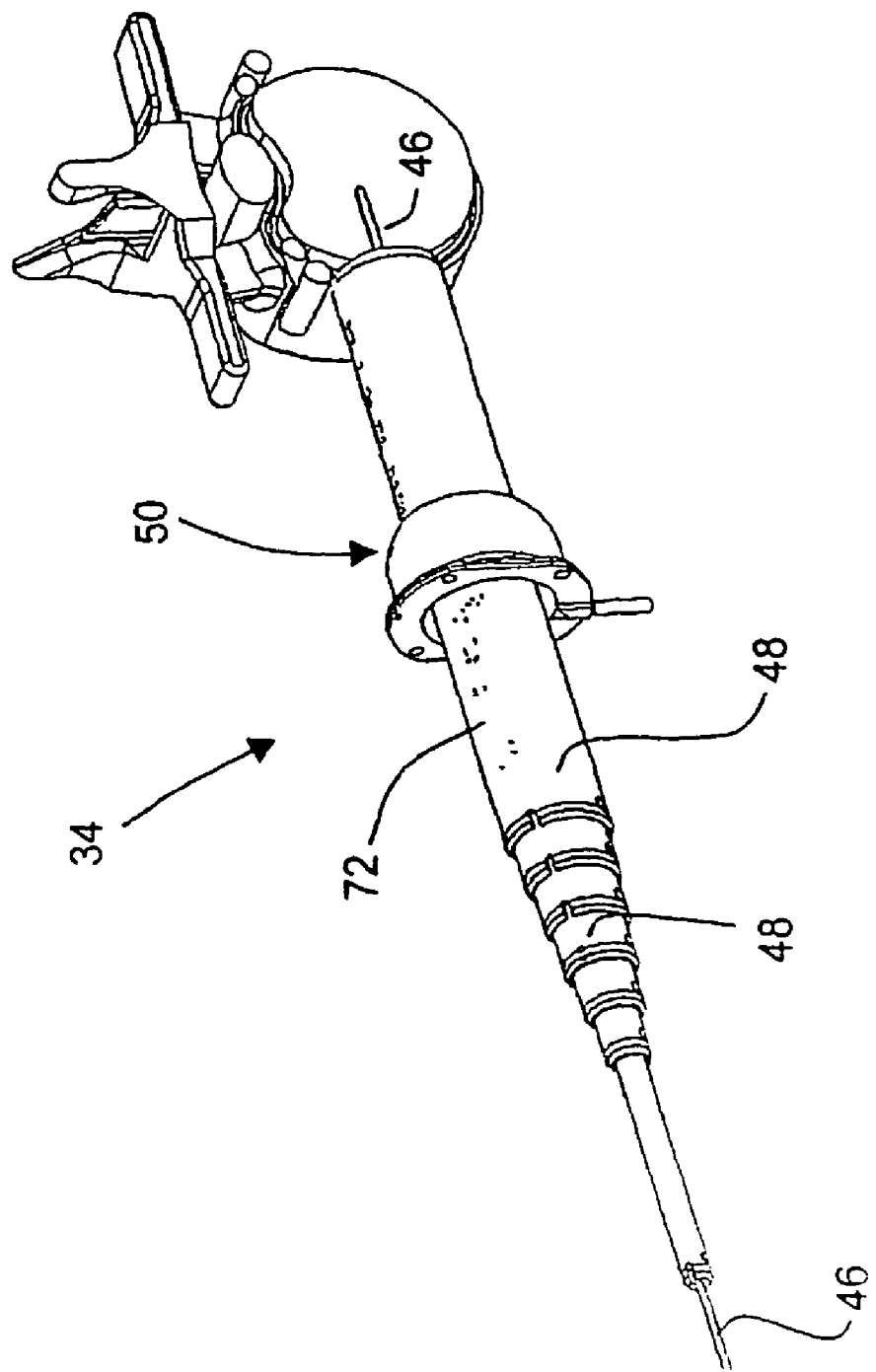
Figure 19:
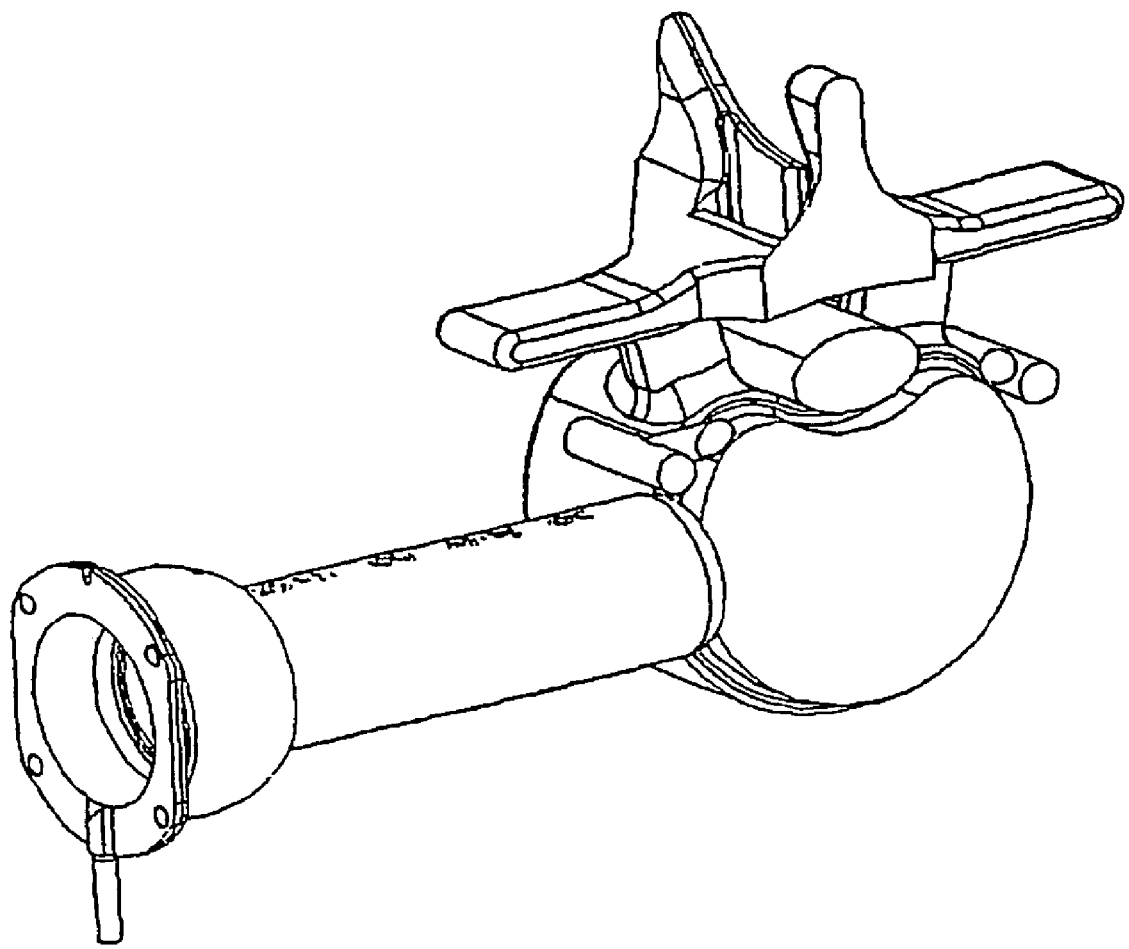

In the embodiment shown, the trajectory of the K-wire 46 and initial dilator 48 is such that they progress towards an intervertebral target site in a postero-lateral, trans-psoas fashion so as to avoid the bony posterior elements of the spinal column. Once the K-wire 46 is docked against the annulus of the particular intervertebral disk, cannulae of increasing diameter may then be guided over the previously installed cannula 48 until a desired lumen diameter is installed, as shown in FIG. 17. By way of example only, the dilating cannulae 26 may range in diameter from 6 mm to 30 mm, with length generally decreasing with increasing diameter size. Depth indicia 72 may be optionally provided along the length of each dilating cannula 48 to aid the user in gauging the depth between the skin of the patient and the surgical target site. As shown in FIG. 18, the working cannula 50 may be slideably advanced over the last dilating cannula 48 after a desired level of tissue dilation has been achieved. As shown in FIG. 19, the last dilating cannula 48 and then all the dilating cannulae 26 may then be removed from inside the inner lumen of the working cannula 50 to establish the operative corridor therethrough.

Figure 20:
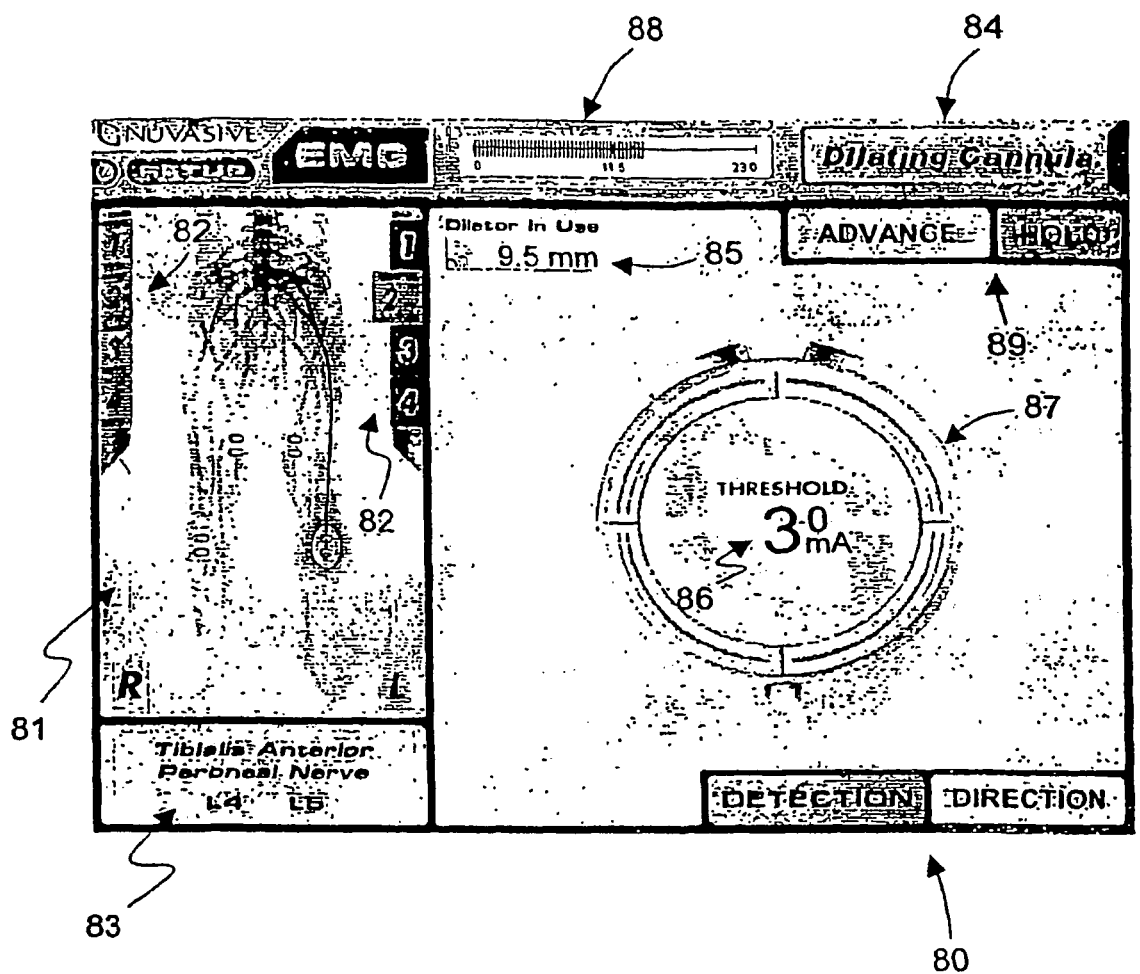
FIG. 20 is an exemplary screen display illustrating one embodiment of the nerve proximity or detection feature of the surgical access system of the present invention.

During the advancement of the K-wire 46, each dilating cannula 48, and the working cannula 50, the surgical system 20 will perform (under the direction of a user) the nerve proximity and optionally nerve direction assessments according to the present invention. By way of example, this may be explained with reference to FIGS. 20 and 21, which illustrate exemplary graphic user interface (GUI) screens provided on the screen display 40 for the purpose of allowing the user to control the surgical system 20 to access a surgical target site according to the present invention. In one embodiment, the surgical system 20 initially operates in a "DETECTION" mode, as shown in FIG. 20, wherein a mode label 80 will preferably show the word "DETECTION" highlighted to denote the nerve proximity function of the present invention. A spine image 81 will preferably be provided showing electrode placement on the body, with labeled EMG channel number tabs 82 on each side (1-4 on left and right) capable of being highlighted or colored depending on the specific function being performed. A myotome label 83 is provided indicating the myotome associated with each EMG channel tab 81, including (optionally) the corresponding spinal level(s) associated with the channel of interest. A surgical accessory label 84 is provided indicating the particular surgical accessory 30 being employed at any given time (i.e. "Dilating Cannula" to denote use of the sequential dilation access system 34), as well as a "Dilator in Use" display 85 showing (graphically and numerically) the particular diameter of the dilating cannula 48 in use. A threshold label 86 is also provided indicating the stimulation threshold required to elicit a measurable EMG response for a given myotome. In one embodiment, this is situated, by way of example only, within a cannula graphic 87 denoting a cross-section of the dilating cannula in use). A horizontal bar-chart 88 may also be provided indicating the stimulation level being emitted from the particular surgical accessory in use.

Any number of the above-identified indicia (such as the threshold label 86 and EMG channel tabs 82) may be color-coded to indicate general proximity ranges (i.e. "green" for a range of stimulation thresholds above a predetermined safe value, "red" for range of stimulation thresholds below a predetermined unsafe value, and "yellow" for the range of stimulation thresholds in between the predetermined safe and unsafe values—designating caution). In one embodiment, "green" denotes a stimulation threshold range of 9 milliamps (mA) or greater, "yellow" denotes a stimulation threshold range of 6-8 mA, and "red" denotes a stimulation threshold range of 6 mA or below. An "Advance-or-Hold" display 89 may also be provided to aid the user in progressing safely through the tissue required to create the operative corridor. ADVANCE may be highlighted indicating it is safe to advance the cannula (such as where the stimulation threshold is within the safe or "green" range). HOLD may be highlighted indicating to the user that the particular surgical accessory may be too close to a nerve (such as where the stimulation threshold is within the "yellow" or "red" ranges) and/or that the surgical system 20 is in the process of determining proximity and/or direction. In one embodiment, ADVANCE may be omitted, leaving it to the discretion of the user to advance the dilating cannula as soon as the HOLD is no longer illuminated or highlighted.

Insertion and advancement of the access instruments 46-50 should be performed at a rate sufficiently slow to allow the surgical system 20 to provide real-time indication of the presence of nerves that may lie in the path of the tip. To facilitate this, the threshold current $I_{Thresh}$ may be displayed such that it will indicate when the computation is finished and the data is accurate. For example, when the DETECTION information is up to date and the instrument such that it is now ready to be advanced by the surgeon, it is contemplated to have the color display show up as saturated to communicate this fact to the surgeon. During advancement of the instrument, if an EMG channel's color range changes from green to yellow, advancement should proceed more slowly, with careful observation of the detection level. If the channel color stays yellow or turns green after further advancement, it is a possible indication that the instrument tip has passed, and is moving farther away from the nerve. If after further advancement, however, the channel color turns red, then it is a possible indication that the instrument tip has moved closer to a nerve. At this point the display will show the value of the stimulation current threshold in mA. Further advancement should be attempted only with extreme caution, while observing the threshold values, and only if the clinician deems it safe. If the clinician decides to advance the instrument tip further, an increase in threshold value (e.g. from 3 mA to 4 mA) may indicate the Instrument tip has safely passed the nerve. It may also be an indication that the instrument tip has encountered and is compressing the nerve. The latter may be detected by listening for sporadic outbursts, or "pops", of nerve activity on a free running EMG audio output forming part of the surgical system 20.

Figure 21:
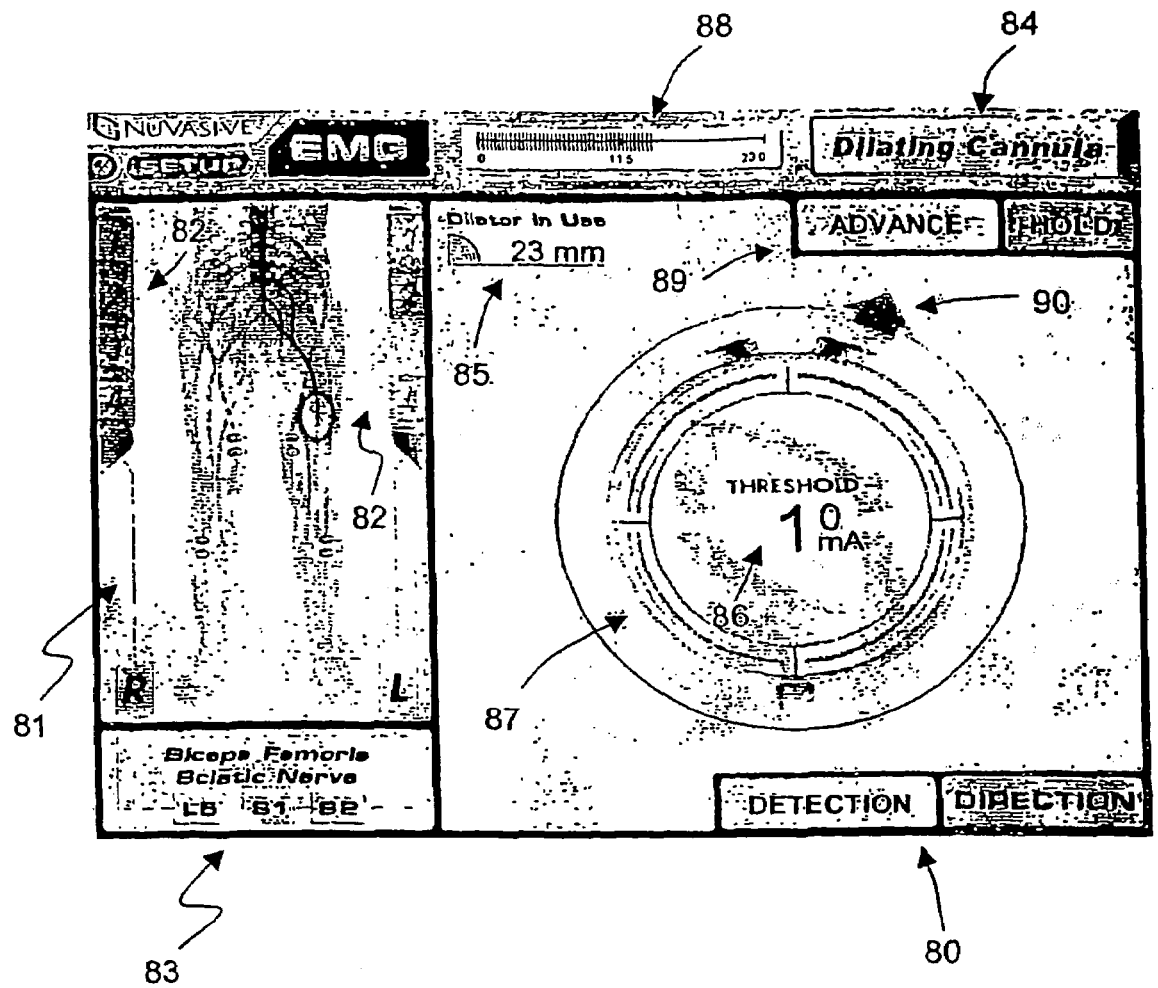
FIG. 21 is an exemplary screen display illustrating one embodiment of the nerve detection feature of the surgical access system of the present invention.
Figure 22:
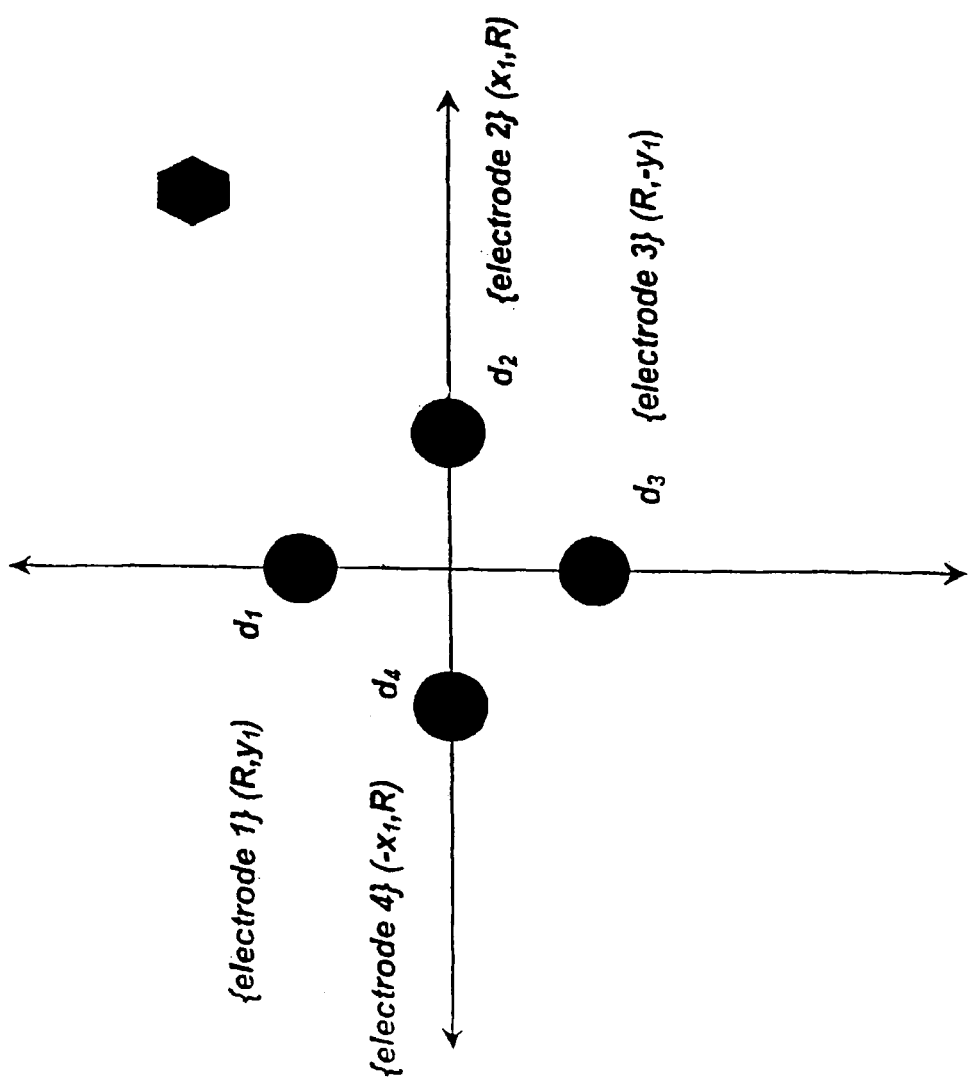
FIG. 22 is a graph illustrating a method of determining the direction of a nerve (denoted as an "octagon") relative to an instrument having four (4) orthogonally disposed stimulation electrodes (denoted by the "circles") according to one embodiment of the present invention.

Once a nerve is detected using the K-wire 46, dilating cannula 48, or the working cannula 50, the surgeon may select the DIRECTION function to determine the angular direction to the nerve relative to a reference mark on the access components 46-50, as shown in FIG. 21. In one embodiment, a directional arrow 90 is provided, by way of example only, disposed around the cannula graphic 87 for the purpose of graphically indicating to the user what direction the nerve is relative to the access components 46-50. This information helps the surgeon avoid the nerve as he or she advances the cannula. In one embodiment, this directional capability is accomplished by equipping the dilators 48 and working cannula 50 with four (4) stimulation electrodes disposed orthogonally on their distal tip. These electrodes are preferably scanned in a monopolar configuration (that is, using each of the 4 electrodes as the stimulation source). The threshold current $(I_{Thresh})$ is found for each of the electrodes by measuring the muscle evoked potential response Vpp and comparing it to a known threshold Vthresh. From this information, the direction from a stimulation electrode to a nerve may be determined according to the algorithm and technique set forth below and with immediate reference to FIG. 22. The four (4) electrodes are placed on the x and y axes of a two dimensional coordinate system at radius R from the origin. A vector is drawn from the origin along the axis corresponding to each electrode that has a length equal to $I_{Thresh}$ for that electrode. The vector from the origin to a direction pointing toward the nerve is then computed. Using the geometry shown, the (x,y) coordinates of the nerve, taken as a single point, can be determined as a function of the distance from the nerve to each of four electrodes. This can be expressly mathematically as follows:

Where the "circles" denote the position of the electrode respective to the origin or center of the cannula and the "octagon" denotes the position of a nerve, and $d_1, d_2, d_3,$ and $d_4$ denote the distance between the nerve and electrodes 1-4 respectively, it can be shown that:

$$x = \frac{d_1^2 - d_3^2}{-4R} \text{ and } y = \frac{d_2^2 - d_4^2}{-4R}$$

Where R is the cannula radius, standardized to 1, since angles and not absolute values are measured.

After conversion from (x,y) to polar coordinates (r,θ), then θ is the angular direction to the nerve. This angular direction may then be displayed to the user, by way of example only, as the arrow 91 shown in FIG. 21 pointing towards the nerve. In this fashion, the surgeon can actively avoid the nerve, thereby increasing patient safety while accessing the surgical target site. The surgeon may select any one of the 4 channels available to perform the Direction Function. The surgeon should preferably not move or rotate the instrument while using the Direction Function, but rather should return to the Detection Function to continue advancing the instrument.

After establishing an operative corridor to a surgical target site via the surgical access system 34 of the present invention, any number of suitable instruments and/or implants may be introduced into the surgical target site depending upon the particular type of surgery and surgical need. By way of example only, in spinal applications, any number of implants and/or instruments may be introduced through the working cannula 50, including but not limited to spinal fusion constructs (such as allograft implants, ceramic implants, cages, mesh, etc . . . ), fixation devices (such as pedicle and/or facet screws and related tension bands or rod systems), and any number of motion-preserving devices (including but not limited to total disc replacement systems).

II. Pedicle Integrity Assessment

With reference again to FIGS. 2-3, the surgical system 20 can also be employed to perform pedicle integrity assessments via the use of pedicle testing assembly 36. More specifically, The pedicle testing assembly 36 of the present invention is used to test the integrity of pedicle holes (after formation) and/or screws (after introduction). The pedicle testing assembly 36 includes a handle assembly 54 and a probe member 56 having a generally ball-tipped end 60. The handle 54 may be equipped with a mechanism (via hardware and/or software) to identify itself to the surgical system 20 when it is attached. In one embodiment, the probe member 56 is disposable and the handle 54 is reusable and sterilizable. The handle 54 may be equipped with one or more buttons for selectively applying the electrical stimulation to the ball-tipped end 60 at the end of the probe member 56. In use, the ball tip 60 of the probe member 56 is placed in the screw hole prior to screw insertion or placed on the installed screw head and then stimulated to initiate the pedicle integrity assessment function of the present invention. As will be explained in greater detail below, it may also applied directly to a nerve to obtain a baseline current threshold level before testing either the screw hole or screw. If the pedicle wall has been breached by the screw or tap or other device employed to form the screw hole, the stimulation current will pass through the bone to the adjacent nerve roots such that they will depolarize at a lower stimulation current.

Figure 23:
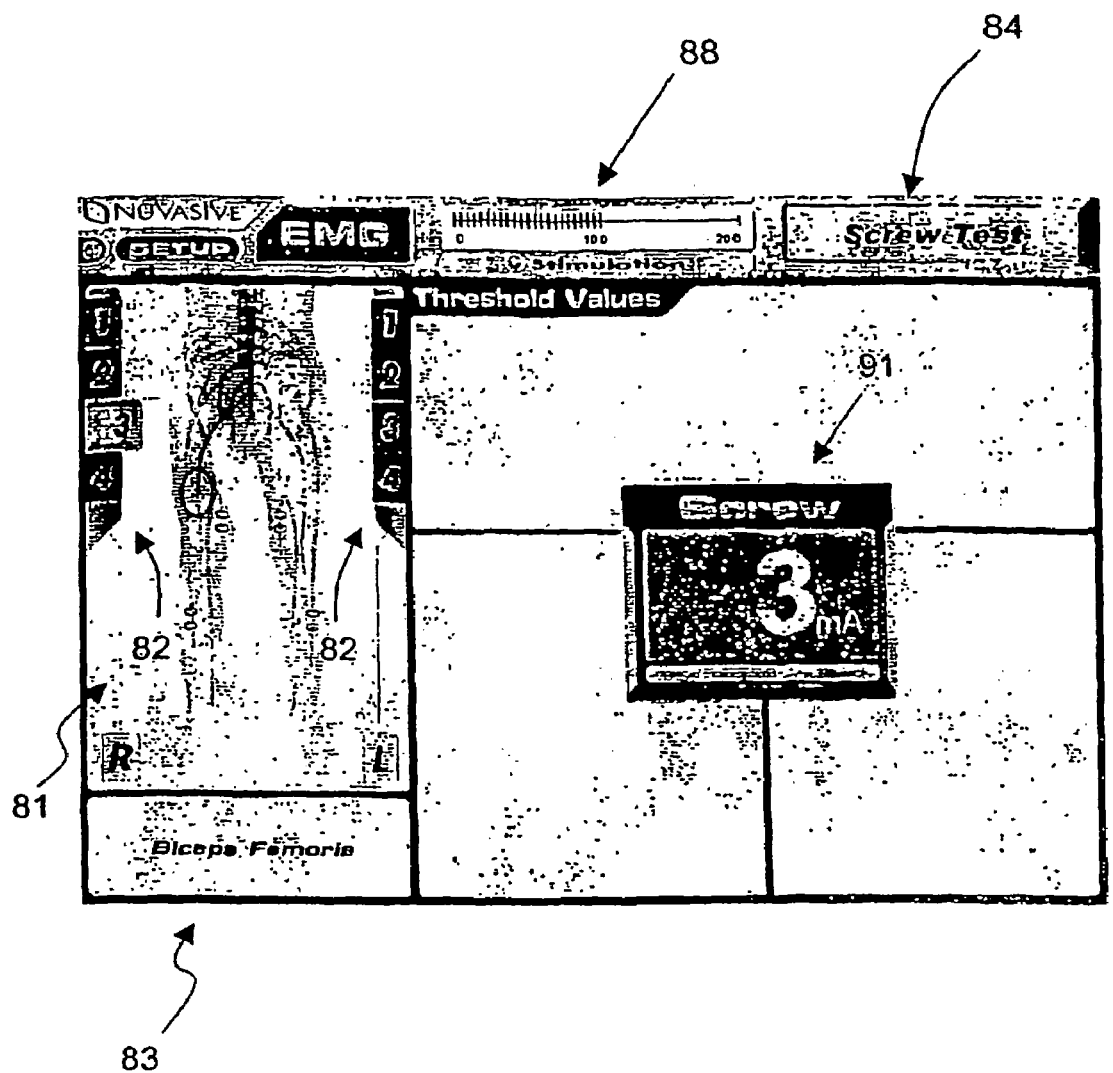
FIGS. 23-24 are exemplary screen displays illustrating one embodiment of the pedicle integrity assessment feature of the present invention.
Figure 24:
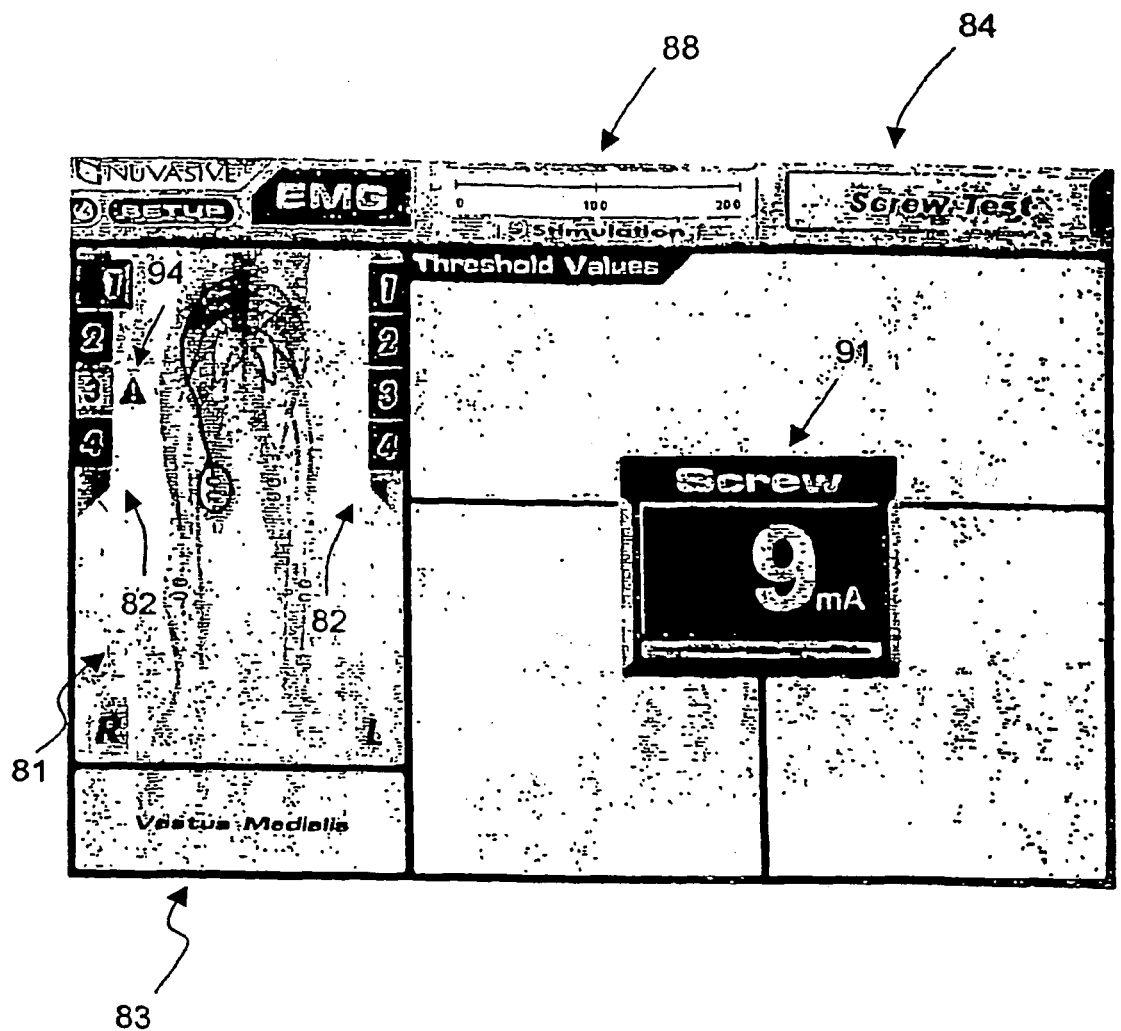
Figure 25:
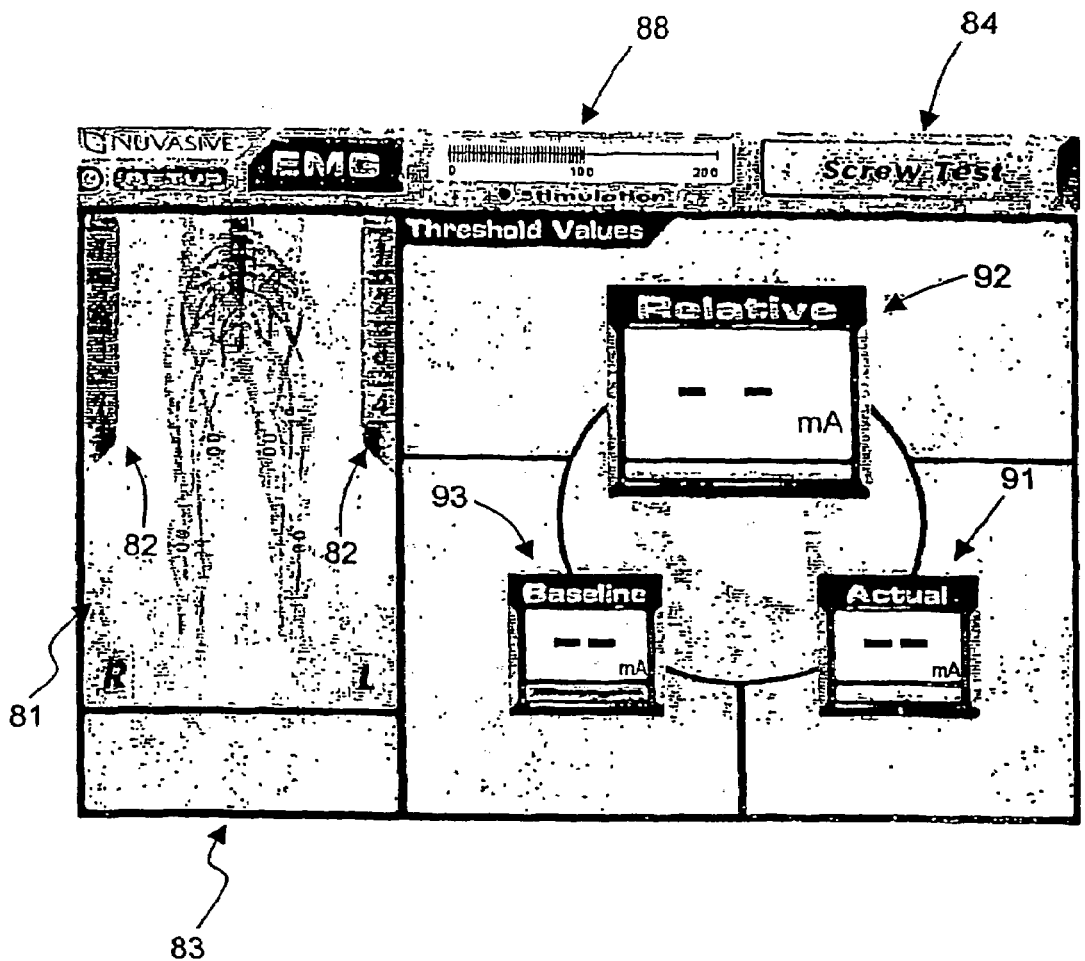
FIGS. 25-27 are exemplary screen displays illustrating another embodiment of the pedicle integrity assessment feature of the present invention.
Figure 26:
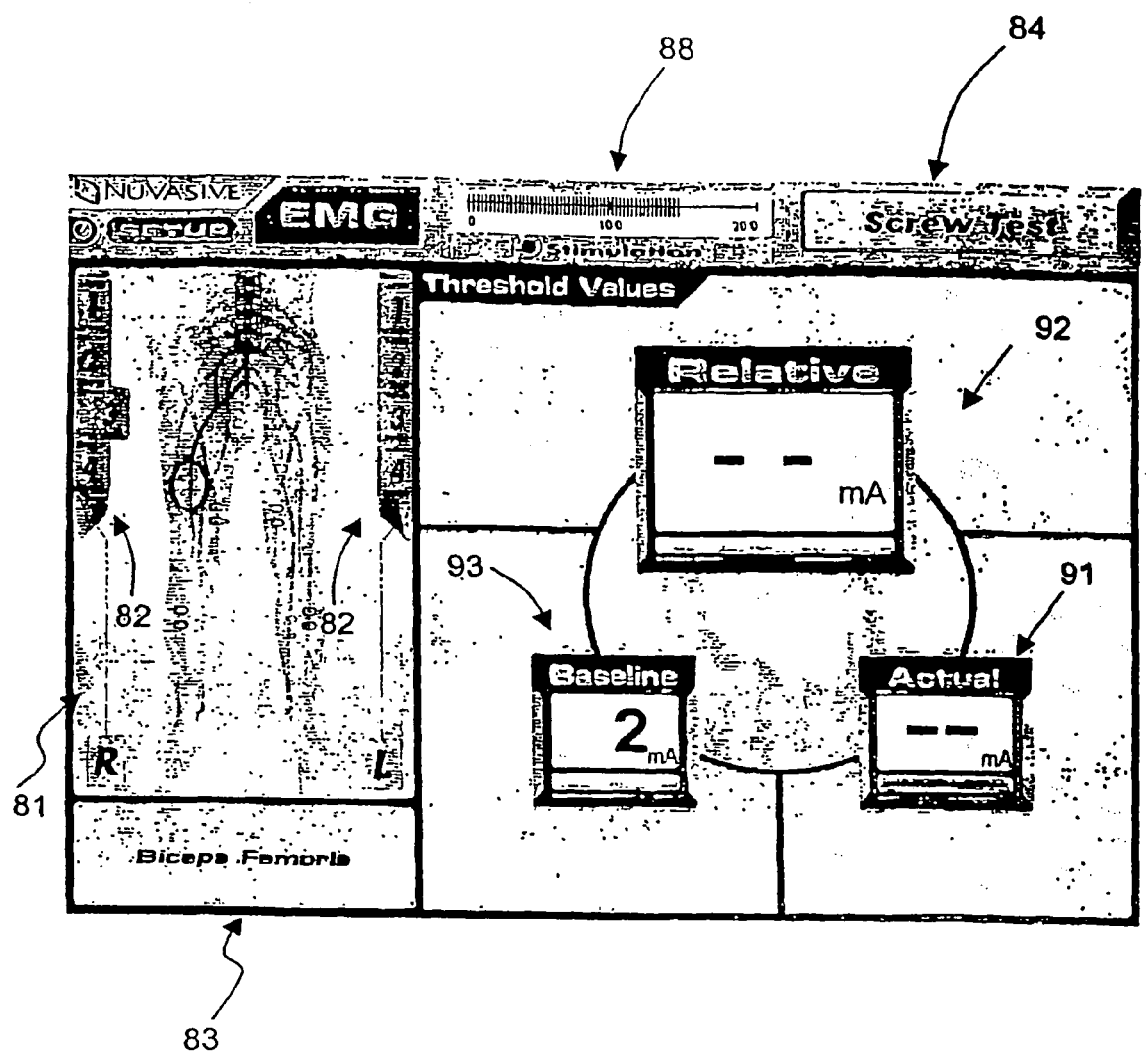
Figure 27:
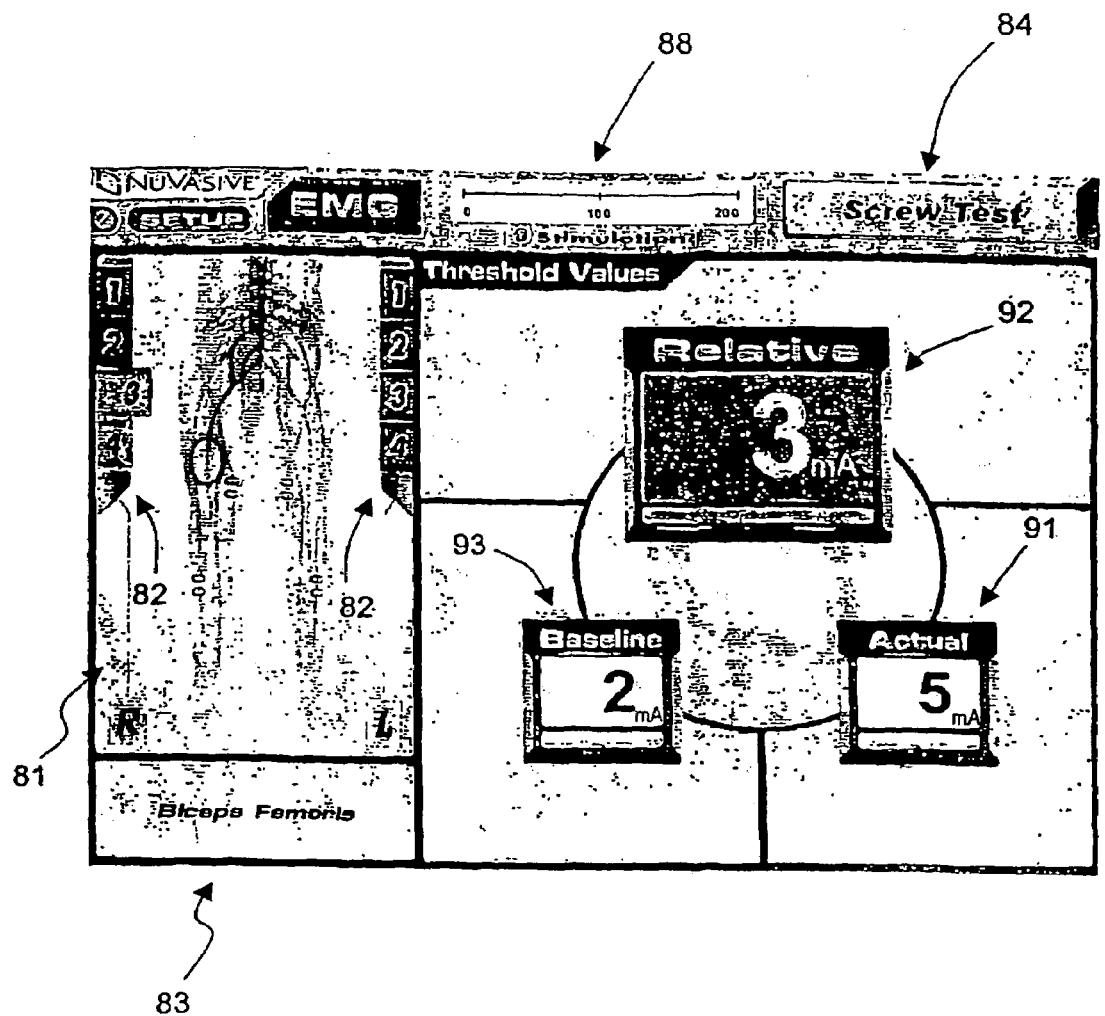

Upon pressing the button on the screw test handle 54, the software will execute a testing algorithm to apply a stimulation current to the particular target (i.e. screw hole, inserted pedicle screw, or bare nerve), setting in motion the pedicle integrity assessment function of the present invention. The pedicle integrity assessment features of the present invention may include, by way of example only, an "Actual" mode (FIGS. 23-24) for displaying the actual stimulation threshold 91 measured for a given myotome, as well as a "Relative" mode (FIGS. 25-27) for displaying the difference 92 between a baseline stimulation threshold assessment 93 of a bare nerve root and an actual stimulation threshold assessment 91 for a given myotome. In either case, the surgical accessory label 84 displays the word "SCREW TEST" to denote use of the pedicle testing assembly 36 for performing pedicle integrity assessments. The screw test algorithm according to the present invention preferably determines the depolarization (threshold) current for all responding EMG channels. In one embodiment, the EMG channel tabs 82 may be configured such that the EMG channel having the lowest stimulation threshold will be automatically enlarged and/or highlighted and/or colored (EMG channel tab R3 as shown in FIG. 23) to clearly indicate this fact to the user. As shown in FIG. 24, this feature may be overridden by manually selecting another EMG channel tab (such as EMG channel tab R1 in FIG. 24) by touching the particular EMG channel tab 82 on the touch screen display 40. In this instance, a warning symbol 94 may be provided next to the EMG channel tab having the lowest stimulation threshold (once again, EMG channel tab R3 in FIG. 23) to inform the user that the stimulation threshold 91 is not the lowest stimulation threshold.

Any number of the above-identified indicia (such as the baseline stimulation 93, actual stimulation 91, difference 92, and EMG channel tabs 82) may be color-coded to indicate general safety ranges (i.e. "green" for a range of stimulation thresholds above a predetermined safe value, "red" for range of stimulation thresholds below a predetermined unsafe value, and "yellow" for the range of stimulation thresholds in between the predetermined safe and unsafe values—designating caution). In one embodiment, "green" denotes a stimulation threshold range of 9 milliamps (mA) or greater, "yellow" denotes a stimulation threshold range of 6-8 mA, and "red" denotes a stimulation threshold range of 6 mA or below. By providing this information graphically, a surgeon may quickly and easily test to determine if the integrity of a pedicle has been breached or otherwise compromised, such as may result due to the formation of a pedicle screw hole and/or introduction of a pedicle screw. More specifically, if after stimulating the screw hole and/or pedicle screw itself the stimulation threshold is: (a) at or below 6 mA, the threshold display 40 will illuminate "red" and thus indicate to the surgeon that a breach is likely; (b) between 6 and 8 mA, the threshold display 40 will illuminate "yellow" and thus indicate to the surgeon that a breach is possible; and/or (c) at or above 8 mA, the threshold display 40 will illuminate "green" and thus indicate to the surgeon that a breach is unlikely. If a breach is possible or likely (that is, "yellow" or "red"), the surgeon may choose to withdraw the pedicle screw and redirect it along a different trajectory to ensure the pedicle screw no longer breaches (or comes close to breaching) the medial wall of the pedicle.

III. Neural Pathology Monitoring

The surgical system 20 may also be employed to perform neural pathology monitoring. As used herein, "neural pathology monitoring" is defined to include monitoring the effect of nerve retraction over time ("nerve retraction monitoring"), as well as monitoring the effect of a surgery on a particular unhealthy nerve ("surgical effect monitoring"). The former—nerve retraction monitoring—is advantageous in that it informs the surgeon if, and the extent to which, such retraction is degrading or damaging an otherwise healthy nerve under retraction. The latter—surgical effect monitoring—is advantageous in that it informs the surgeon if, and the extent to which, the given surgical procedure is improving or aiding a previously unhealthy nerve. In both cases, the qualitative assessment of improvement or degradation of nerve function may be defined, by way of example, based on one or more of the stimulation threshold ($I_{Thresh}$), the slope of the EMG response (uV) versus the corresponding stimulation threshold ($I_{Thresh}$), and/or the saturation or maximum EMG response (Vpp) for a given nerve root being monitored.

Figure 28:
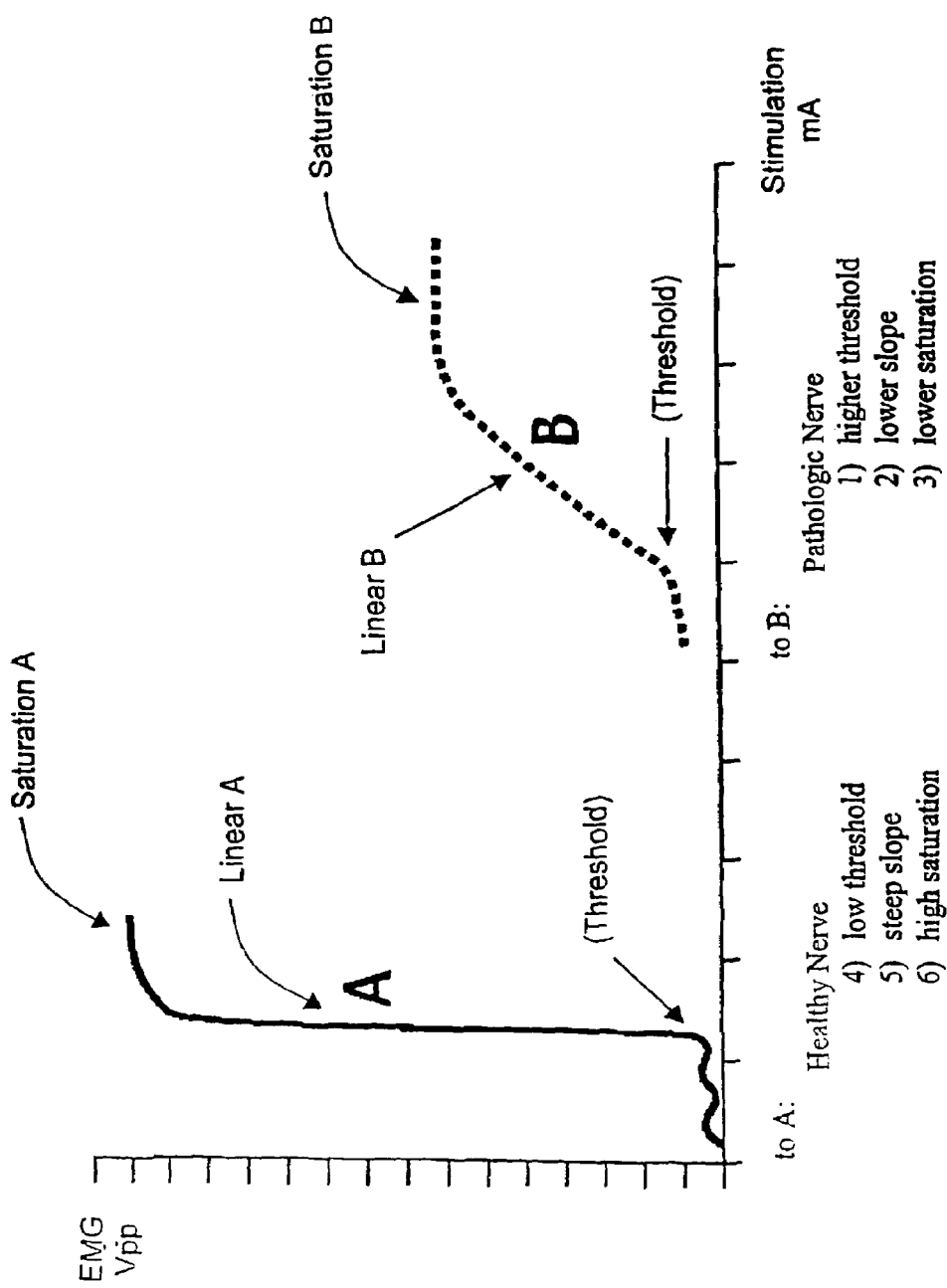
FIG. 28 is a graph illustrating recruitment curves for a generally healthy nerve (denoted "A") and a generally unhealthy nerve (denoted "B") according to the nerve pathology monitoring feature of the present invention.
Figure 29:
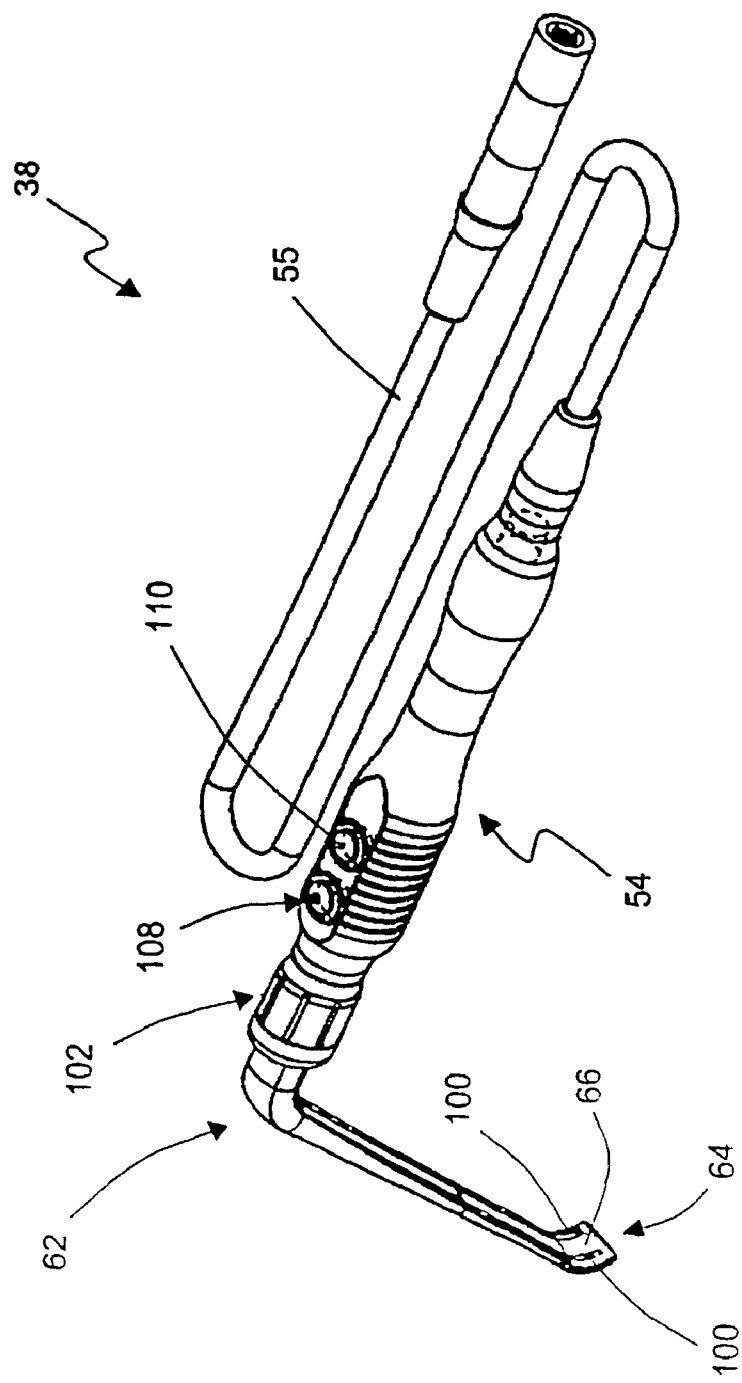
FIGS. 29-30 are perspective and side views, respectively, of an exemplary nerve root retractor assembly according to one embodiment of the present invention.
Figure 30:
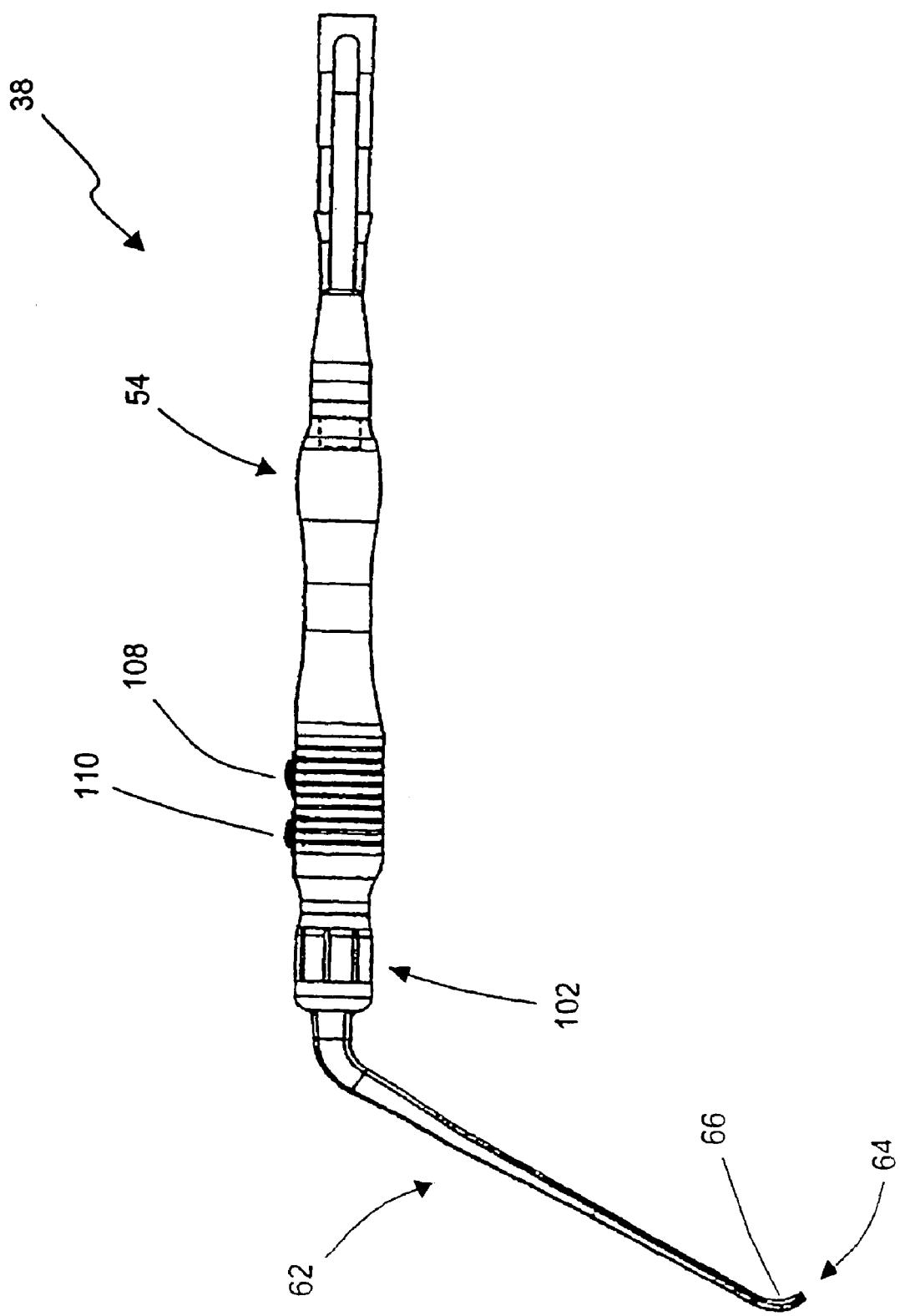

FIG. 28 illustrates this important aspect of the present invention, noting the differences between a healthy nerve (A) and an unhealthy nerve (B). The inventors have found through experimentation that information regarding nerve pathology (or "health" or "status") can be extracted from recruitment curves generated according to the present invention. In particular, it has been found that a healthy nerve or nerve bundle will produce a recruitment curve having a generally low current threshold ($I_{Thresh}$), a linear region having a relatively steep slope, and a relatively high saturation region (similar to those shown on recruitment curve "A" in FIG. 28). On the contrary, a nerve or nerve bundle that is unhealthy or whose function is otherwise compromised or impaired (such as being impinged by spinal structures or by prolonged retraction) will produce recruitment curve having a generally higher threshold, a linear region of reduced slope, and a relatively low saturation region (similar to those shown on recruitment curve "B" in FIG. 28). By recognizing these characteristics, one can monitor a nerve root being retracted during a procedure to determine if its pathology or health is affected (i.e. negatively) by such retraction. Moreover, one can monitor a nerve root that has already been deemed pathologic or unhealthy before the procedure (such as may be caused by being impinged by bony structures or a bulging annulus) to determine if its pathology or health is affected (i.e. positively) by the procedure.

Figure 31:
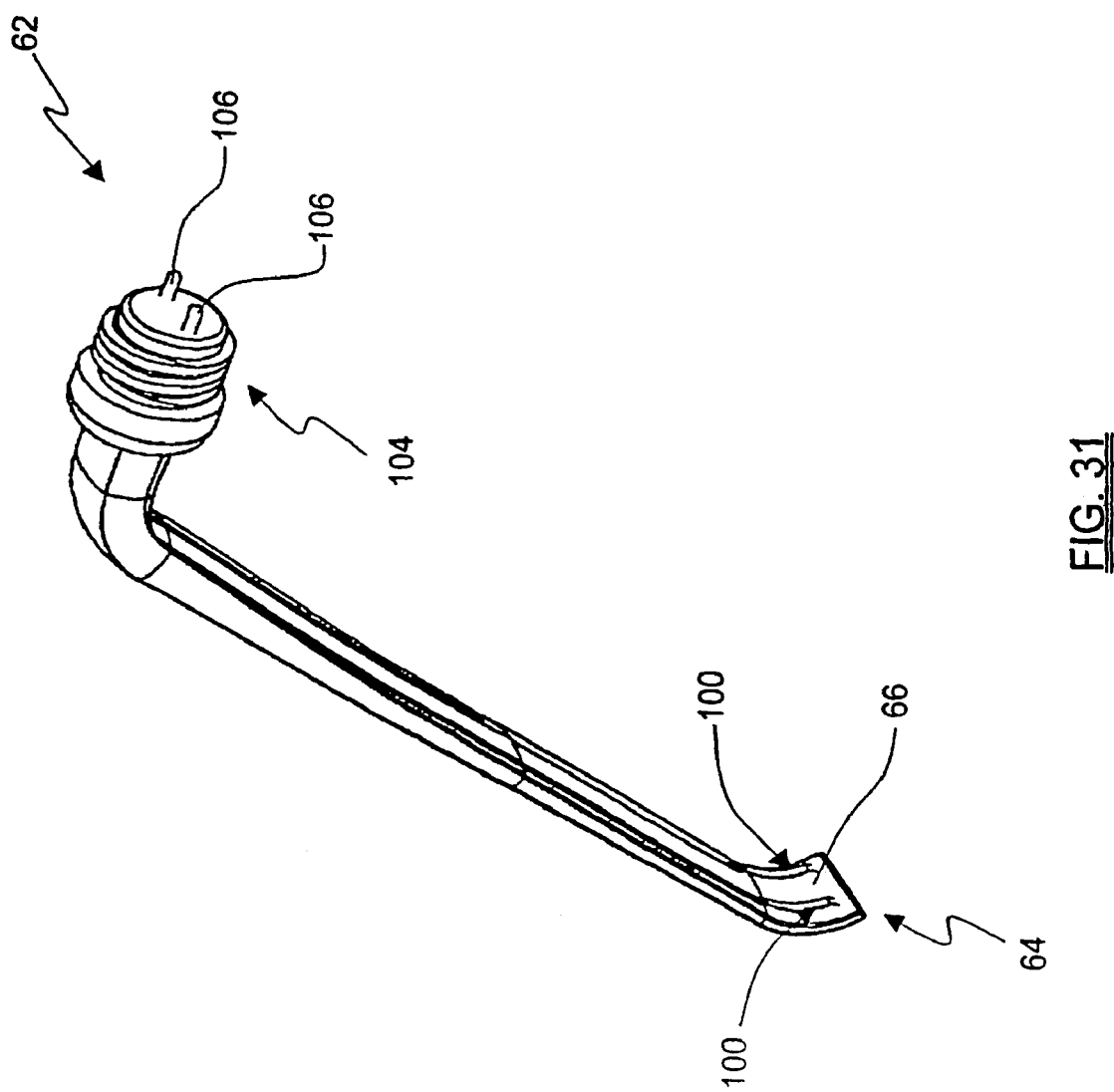
FIG. 31 is a perspective view of an exemplary nerve root retractor according to one embodiment of the present invention.

The nerve root retractor assembly 38 shown in FIG. 2 is capable of performing both types of neural pathology monitoring. However, based on its particular shape and configuration (being bent and suitably shaped to hook and thereafter move a nerve root out of a surgical target site), it is better suited to perform "nerve retraction monitoring." With combined reference to FIGS. 2 and 29-31, the nerve root retractor assembly 38 includes the same style surgical accessory handle assembly 54 as employed with in the pedicle testing assembly 36. The nerve root retractor 62 has a generally angled orientation relative to the longitudinal axis of the handle assembly 54. The distal end 64 is generally curved and includes an arcuate nerve engagement surface 66 equipped with, by way of example only, two stimulation electrodes 100. As best shown in FIG. 31, the nerve root retractor 62 is preferably removable from the handle assembly 36. To accomplish this, the handle assembly 54 includes a detachable cap member 102. Threads 104 are provided on the proximal end of the nerve root retractor 62 to allow a threaded coupling engagement between the handle assembly 54 and the nerve root retractor 62. During such engagement, electrical contacts 106 on the nerve root retractor 62 becomes electrically coupled to the handle assembly 54 such that, upon activation of one or more of the buttons 108, 110, a stimulation current signal will be transmitted from the control unit 22 and/or patient module 24 and delivered to the stimulation electrodes 100 on the nerve root retractor 62 for the purpose of performing neural pathology monitoring according to the present invention. The nerve root retractor 62 is preferably disposable and, as described above, the handle assembly 54 is reusable and sterilizable.

In use, the nerve root retractor 62 is introduced into or near a surgical target site in order to hook and retract a given nerve out of the way. According to the present invention, the nerve root may be stimulated (monopolar or bipolar) before, during, and/or after retraction in order to assess the degree to which such retraction impairs or otherwise degrades nerve function over time. To do so, the user may operate one or more buttons 108, 110 of the handle assembly 54 to selectively transmit a stimulation signal (preferably, a current signal) from the patient module 24 to the electrode(s) on the engagement surface 66 of the nerve root retractor 62. By monitoring the myotome associated with the nerve root being retracted (via the EMG harness 26) and assessing the resulting EMG responses (via the control unit 22), the surgical system 20 can assess whether (and the degree to which) such retraction impairs or adversely affects nerve function over time. With this information, a user may wish to periodically release the nerve root from retraction to allow nerve function to recover, thereby preventing or minimizing the risk of long-term or irreversible nerve impairment. As will be described in greater detail below, a similar neural pathology assessment can be undertaken, whereby an unhealthy nerve may be monitored to determine if nerve function improves due to a particular surgical procedure, such as spinal nerve decompression surgery.

Figure 32:
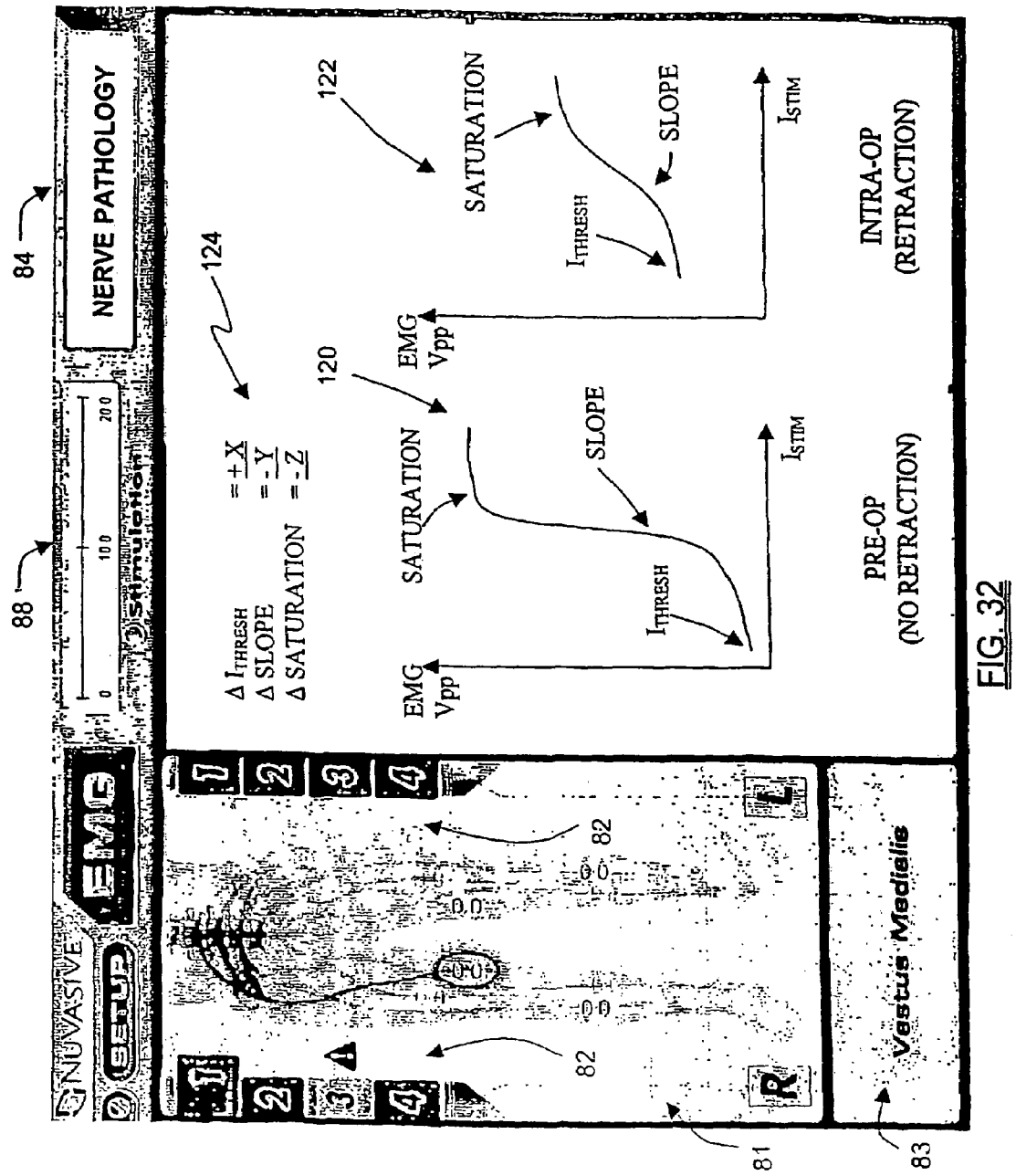
FIG. 32 is an exemplary screen display illustrating one embodiment of the neural pathology monitoring feature of the present invention, specifically for monitoring change in nerve function of a healthy nerve due to nerve retraction.
Figure 33:
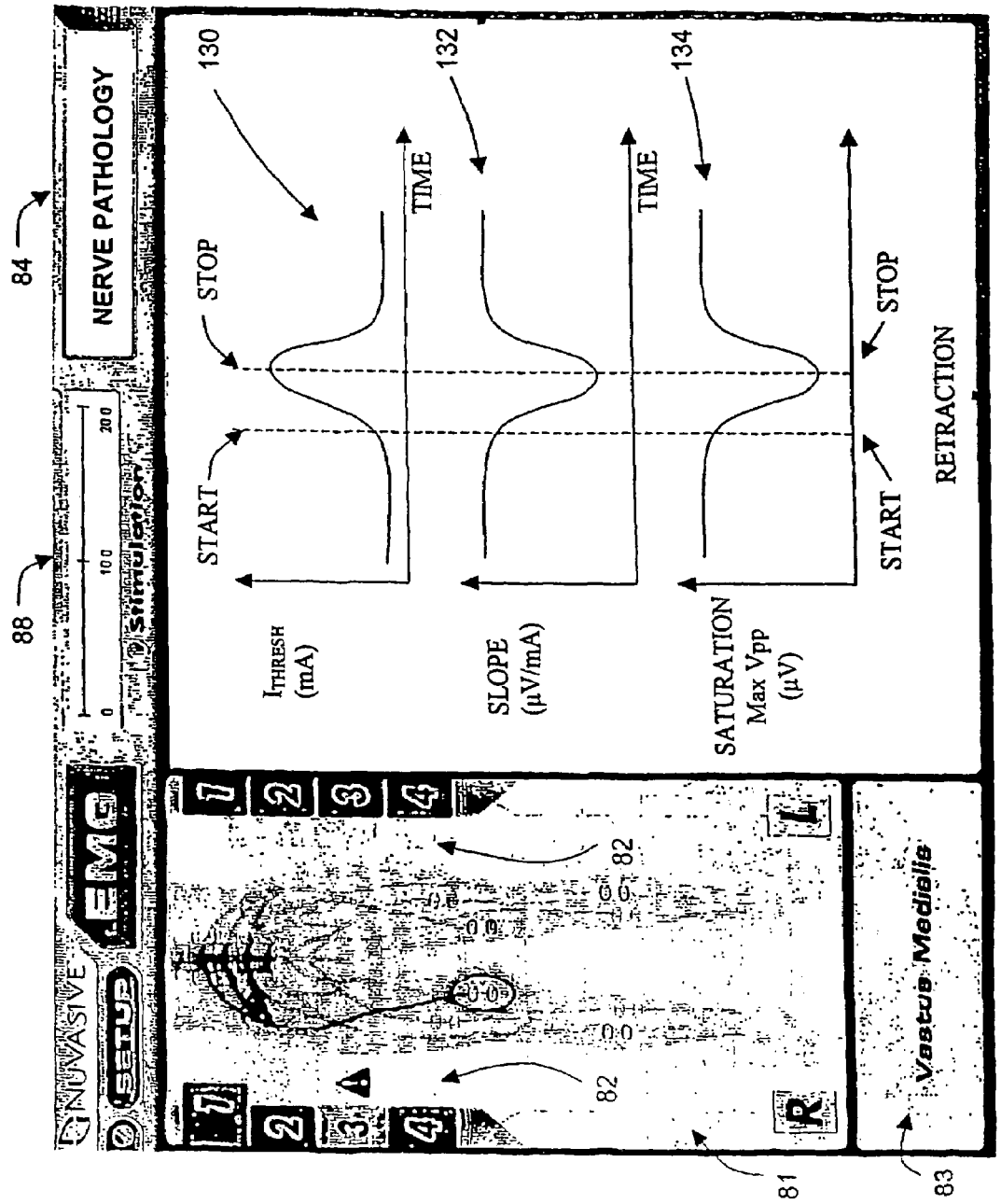
FIG. 33 is an exemplary screen display illustrating another embodiment of the neural pathology monitoring feature of the present invention, specifically for monitoring change in nerve function of a healthy nerve due to nerve retraction.

The nerve retraction monitoring feature of the present invention is best viewed with regard to FIGS. 32 and 33. The neural pathology screen display 40 may include any of a variety of indicia capable of communicating parameters associated with the nerve retraction monitoring feature of the present invention to a surgeon, including but not limited to (in FIG. 32) a pre-operative recruitment curve graph 120, an intra-operative recruitment curve graph 122, and a differential display 124 indicating the relative difference between the stimulation threshold, slope, and saturation before the surgery and during the surgery. In this manner, the surgeon may intra-operatively assess if the retracted nerve is being damaged or otherwise compromised (such as due to a prolonged surgery), such that it can be temporarily released to allow it to recover before returning to retraction to continue with the surgery. It's believed that releasing the nerve root in this fashion will prevent or reduce the adverse effects (nerve function compromise) that may otherwise result from prolonged retraction.

FIG. 33 shows an alternate screen display including a stimulation threshold vs. time graph 130, slope vs. time graph 132, and saturation vs. time graph 134 for a given healthy nerve (as measured at a particular myotome) during nerve retraction monitoring. As will be appreciated, the start of nerve retraction initiates a progressive increase in stimulation threshold 130 and a concomitant progressive decrease in slope 132 and saturation 134, all of which cease and reverse at or close to the point the retraction is stopped. By monitoring this information, a surgeon can effectively determine when the nerve is in need of being released and, after that point, when it is generally safe to resume retraction.

Figure 34:
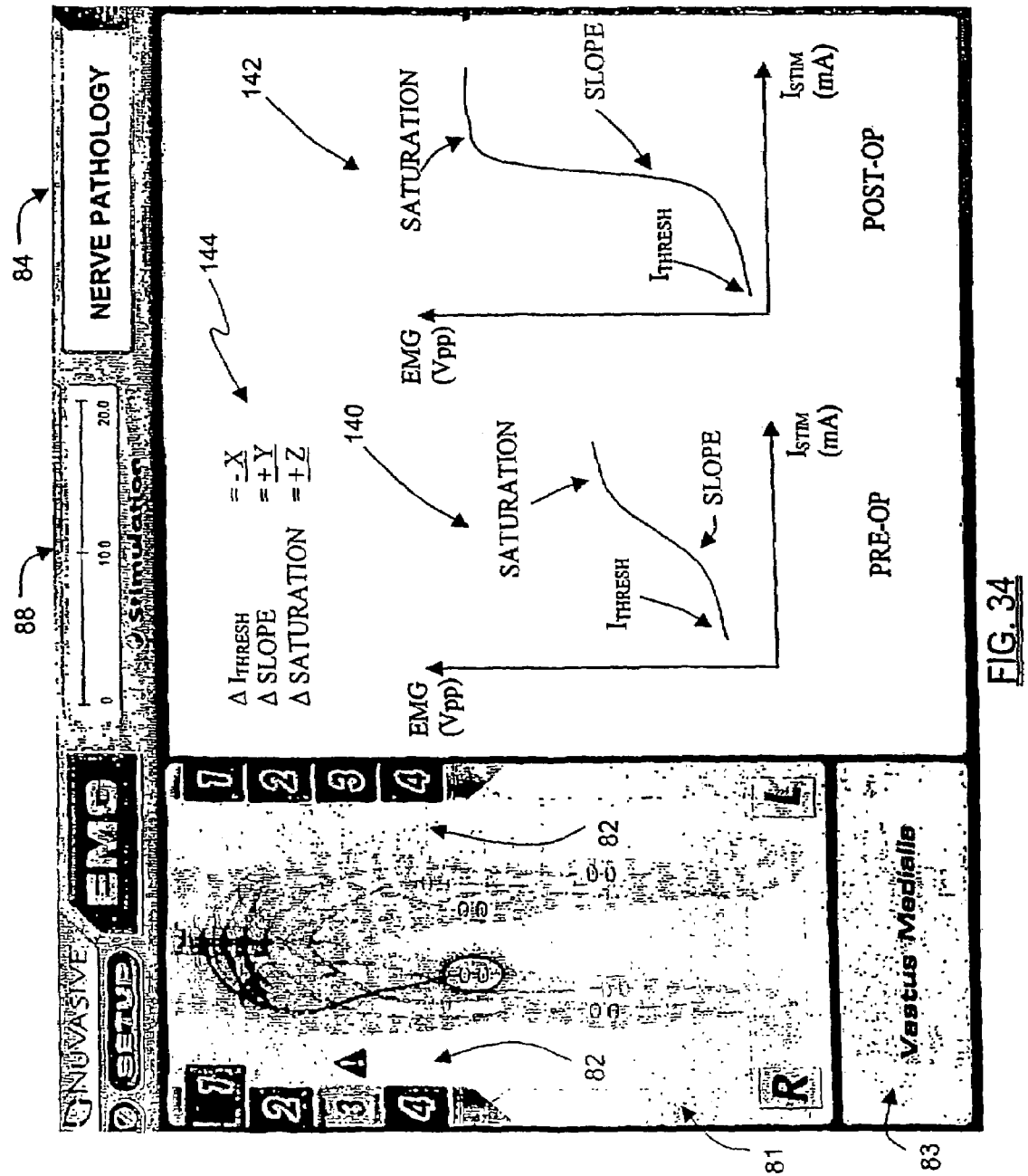
FIG. 34 is an exemplary screen display illustrating one embodiment of the neural pathology monitoring feature of the present invention, specifically for monitoring change in nerve function of an unhealthy nerve due to the performance of a surgical procedure.
Figure 35:
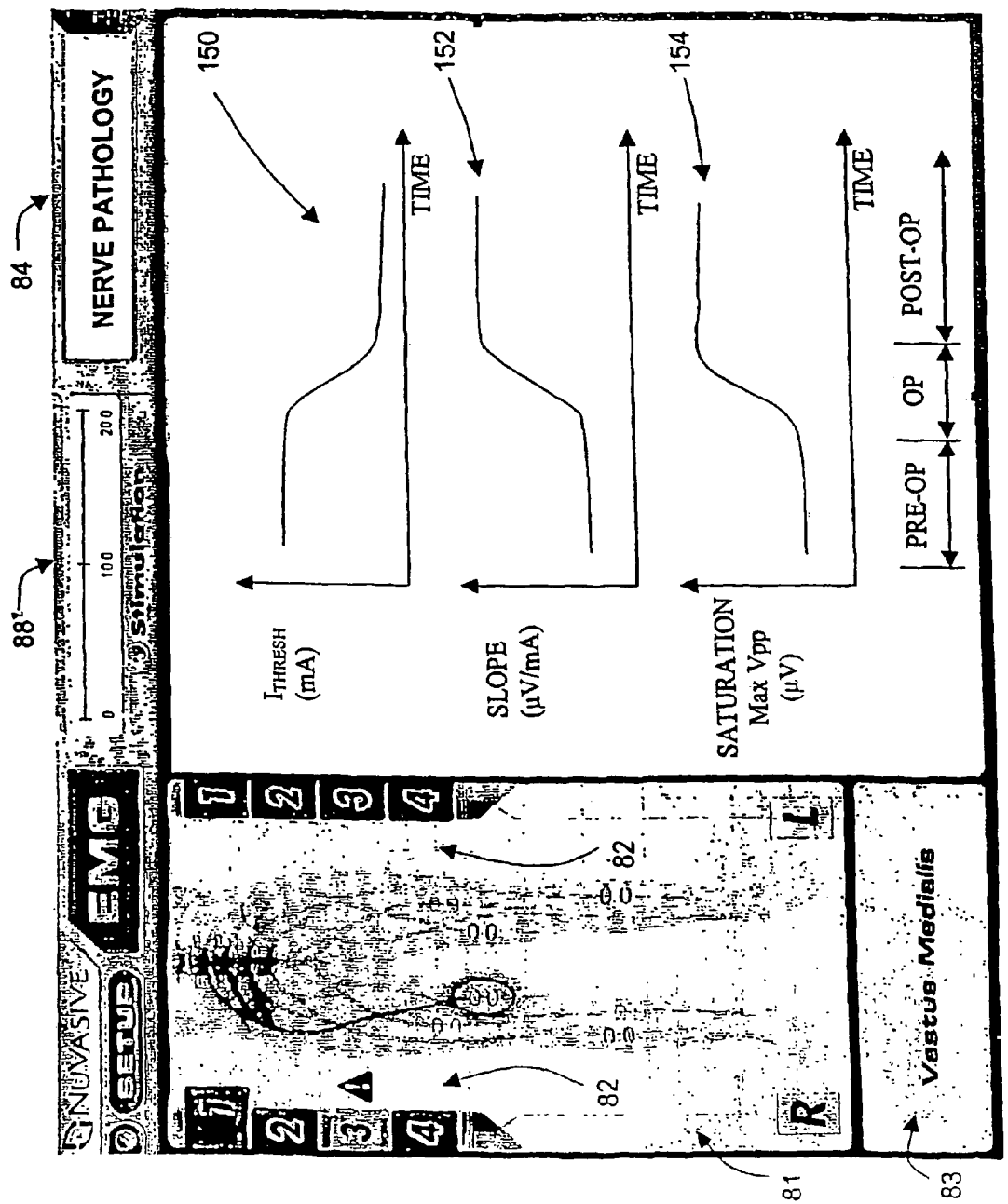
FIG. 35 is an exemplary screen display illustrating another embodiment of the neural pathology monitoring feature of the present invention, specifically for monitoring change in nerve function of an unhealthy nerve due to the performance of a surgical procedure.

The surgical effect nerve monitoring of the present invention is best viewed with regard to FIGS. 34 and 35. The neural pathology screen display 40 may include any of a variety of indicia capable of communicating parameters associated with the surgical effect nerve monitoring feature of the present invention to a surgeon, including but not limited to (in FIG. 34) a pre-operative recruitment curve graph 140, a post-operative recruitment curve graph 142, and a differential display 144 indicating the relative difference between the stimulation threshold, slope, and saturation before the surgery and after the surgery. In this manner, the surgeon may determine whether a previously unhealthy nerve has been positively affected by the surgery. This is particularly advantageous in assessing the effectiveness of spinal decompression surgery, wherein the effectiveness of the decompression may be determined by identifying whether the health of the compressed nerve root improves as a result of the surgery. This determination may also be made, by way of example, by (see FIG. 35) displaying various graphs to the user, such as a stimulation threshold vs. time graph 150, a slope vs. time graph 152, and saturation vs. time graph 154 for a given unhealthy nerve (as measured at a particular myotome) before, during, and after surgery. As can be seen, an improvement in nerve function due to surgery will cause the stimulation threshold to decrease post-operatively and the slope and saturation to increase post-operatively.

Although not shown, it is to be readily appreciated that the nerve retraction monitoring and surgical effect nerve monitoring techniques described above (both of which form part of the neural pathology monitoring feature of the present invention), should preferably be performed on different myotomes in that the former technique is particularly suited for assessing a healthy nerve and the latter is particularly suited for assessing an unhealthy nerve. Moreover, although not shown in FIGS. 32-35, the various graphs may be formed based on a compilation of EMG responses from more than one myotome without departing from the scope of the present invention.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the scope of the appended claims.

What is claimed is:

1. A system for performing surgical procedures and assessments, comprising:
   a surgical accessory having at least one stimulation electrode; and
   a processing system having at least one of computer programming software, firmware and hardware pre-programmed to incorporate at least two pre-selected threshold ranges, and capable of stimulating said at least one stimulation electrode on a surgical accessory with an electrical stimulation signal, measuring the response of nerves depolarized by said stimulation signal, automatically determining a stimulation threshold of said nerves by automatically adjusting said stimulation signal by variable increments, and communicating to a user which range of said at least two pre-selected ranges that said stimulation threshold lies to indicate at least one of nerve proximity, and pedicle integrity.

2. The system set forth in claim 1 and further, wherein the response of said depolarized nerves is measured by monitoring the EMG waveforms of myotomes associated with said depolarized nerves.

3. The system set forth in claim 2 and further, wherein said surgical accessory comprises a system for establishing an operative corridor to a surgical target site.

4. The system set forth in claim 3 and further, wherein said system for establishing an operative corridor to a surgical site includes a series of sequential dilator cannulae, each having at least one stimulation electrode near a distal end.

5. The system of claim 3 and further, wherein said surgical target site is a spinal target site.

6. The system of claim 5 and further, wherein said operative corridor may be established via a lateral, trans-psoas approach.

7. The system set forth in claim 1 and further, wherein said surgical accessory comprises a pedicle testing device including a handle and a pedicle probe.

8. The system set forth in claim 7 and further wherein said pedicle testing device is capable of testing at least one of the interior of a hole formed in a pedicle and a pedicle screw after insertion into said hole.

9. The system set forth in claim 8 and further, wherein said handle includes at least one button for initiating the transmission of said stimulation signal from said processing system to said pedicle probe.

10. The system set forth in claim 1 and further, wherein said system includes a display for communicating said at least one of nerve proximity and pedicle integrity.

11. The system set forth in claim 10 and further, wherein said display is configured to show at least one of alphanumeric and graphic indicia related to said at least one of said nerve proximity and pedicle integrity.

12. The system set forth in claim 11 and further, wherein said display shows a color indicative of at least one of said nerve proximity and pedicle integrity.

13. The system set forth in claim 1 and further, wherein said system is configured to audibly communicate said at least one of nerve proximity and pedicle integrity.

14. The system set forth in claim 1 and further, wherein said at least two pre-selected threshold ranges comprise a safe range and an unsafe range.

15. The system set forth in claim 14 and further, wherein said system comprises three pre-selected threshold ranges.

16. The system set forth in claim 15 and further, comprising a cautionary range in-between said unsafe and safe ranges.

17. The system set forth in claim 16 and further, wherein one of the colors red, yellow, and green, are highlighted on a display to communicate the appropriate range of said determined stimulation threshold.

18. The system set forth in claim 17 and further, wherein the color red indicates said unsafe range, the color yellow indicates said cautionary range, and the color green indicates said safe range.

19. The system set forth in claim 1 and further, wherein automatically adjusting said stimulation signal by variable increments comprises doubling the amplitude of successive stimulation signals until a corresponding nerve response measures at least a preselected intensity level.

20. The system set forth in claim 19 and further, wherein automatically adjusting said stimulation signal by variable increments further comprises decreasing the amplitude of subsequent stimulation signals until a corresponding nerve response measures below said preselected intensity level.

21. The system set forth in claim 19 and further, wherein the amplitude of said first stimulation signal to evoke said corresponding nerve response of at least a preselected intensity level and the immediately preceding stimulation signal comprise an initial bracket.

22. The system set forth in claim 21 and further, wherein said initial bracket is bisected to a pre-selected width.

23. The system set forth in claim 1 and further, wherein said system is configured to automatically adjust said stimulation signal according to at least one of a bracketing method and a bisection method.

24. The system set forth in claim 23 and further, wherein said system is configured to first determine a bracket within which said stimulation threshold must lie and thereafter to bisect said bracket until said stimulation threshold is known to a specified accuracy.

25. The system set forth in claim 24 and further, wherein said system may determine whether said stimulation threshold has changed by stimulating said at least one stimulation electrode at a stimulation current just below said previously determined stimulation threshold and at least one of at and just above said previously determined stimulation threshold.

* * * * *

UNITED STATES PATENT AND TRADEMARK OFFICE
CERTIFICATE OF CORRECTION

| | |
|---|---|
| PATENT NO. | : 7,522,953 B2 |
| APPLICATION NO. | : 10/809280 |
| DATED | : April 21, 2009 |
| INVENTOR(S) | : Norbert F. Kaula |

It is certified that error appears in the above-identified patent and that said Letters Patent is hereby corrected as shown below:

Title Page, Inventors (75), please delete "Jeffrey J. Blewett, San Diego, CA (US); Goretti Medeiros, legal representative, Plantsville, CT (US);" and insert --Jeffrey J. Blewett, deceased, late of San Diego, CA (US); by Goretti Medeiros, legal representative, Plantsville, CT (US);-- therefor Signed and Sealed this
Sixth Day of December, 2011

David J. Kappos
*Director of the United States Patent and Trademark Office*